(12) United States Patent
Parmee et al.

(10) Patent No.: US 7,301,036 B2
(45) Date of Patent: Nov. 27, 2007

(54) CYCLIC GUANIDINES, COMPOSITIONS CONTAINING SUCH COMPOUNDS AND METHODS OF USE

(75) Inventors: Emma R. Parmee, Scotch Plains, NJ (US); Ronald M. Kim, Summit, NJ (US); Elizabeth A. Rouse, Edison, NJ (US); Darby R. Schmidt, Clark, NJ (US); Christopher Joseph Sinz, Cranford, NJ (US); Jiang Chang, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 40 days.

(21) Appl. No.: 10/580,183

(22) PCT Filed: Dec. 15, 2004

(86) PCT No.: PCT/US2004/042068

§ 371 (c)(1),
(2), (4) Date: May 22, 2006

(87) PCT Pub. No.: WO2005/065680

PCT Pub. Date: Jul. 21, 2005

(65) Prior Publication Data

US 2007/0105930 A1    May 10, 2007

Related U.S. Application Data

(60) Provisional application No. 60/531,213, filed on Dec. 19, 2003.

(51) Int. Cl.
    *C07D 235/30*    (2006.01)

(52) U.S. Cl. .................................................. 548/307.4
(58) Field of Classification Search ............. 548/307.4
    See application file for complete search history.

(56) References Cited

U.S. PATENT DOCUMENTS

| 5,719,173 A | 2/1998 | Nishikawa et al. |
| 5,776,954 A | 7/1998 | de Laszlo et al. |
| 6,218,431 B1 | 4/2001 | Schoen et al. |
| 6,503,949 B1 | 1/2003 | Lau et al. |
| 6,562,807 B2 | 5/2003 | Jorgensen et al. |
| 6,613,942 B1 | 9/2003 | Ling et al. |
| 6,762,318 B2 | 7/2004 | Kodra et al. |
| 2004/0242627 A1* | 12/2004 | Suzuki et al. ............. 514/303 |

FOREIGN PATENT DOCUMENTS

| WO | WO 97/16442 | 5/1997 |
| WO | WO 98/21957 | 5/1998 |
| WO | WO 98/22108 | 5/1998 |
| WO | WO 98/22109 | 5/1998 |
| WO | WO 99/32448 | 7/1999 |
| WO | WO 00/39088 | 7/2000 |
| WO | WO 02/40444 A1 | 5/2002 |

* cited by examiner

*Primary Examiner*—Rebecca Anderson
*Assistant Examiner*—Shawquia Young
(74) *Attorney, Agent, or Firm*—Richard C. Billups; Catherine D. Fitch

(57) ABSTRACT

The present invention relates to cyclic guanidines, compositions containing such compounds and methods of treatment. The compounds are glucagon receptor antagonists and thus are useful for treating, preventing or delaying the onset of type 2 diabetes mellitus.

20 Claims, No Drawings

CYCLIC GUANIDINES, COMPOSITIONS CONTAINING SUCH COMPOUNDS AND METHODS OF USE

CROSS REFERENCE TO RELATED APPLICATIONS

This application is the National Stage of International Application No. PCT/US2004/042068, filed 15 Dec. 2004, which claims the benefit under 35 U.S.C. 119(e) of U.S. Provisional Application No. 60/531,213, filed 19 Dec. 2003.

BACKGROUND OF THE INVENTION

The present invention relates to cyclic guanidine derivatives, compositions containing such compounds and methods of treating type 2 diabetes mellitus.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level $\geq 126$ mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure $\geq 130/80$ mmHg in a resting state), nephropathy, neuropathy and retinopathy.

Patients having type 2 diabetes mellitus characteristically exhibit elevated plasma insulin levels compared with non-diabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by α-cells in pancreatic islets in response to falling blood glucose levels. The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly.

In addition to elevated levels of circulating insulin, type II diabetics have elevated levels of plasma glucagon and increased rates of hepatic glucose production. Antagonists of glucagon are useful in improving insulin responsiveness in the liver, decreasing the rate of gluconeogenesis and lowering the rate of hepatic glucose output resulting in a decrease in the levels of plasma glucose.

SUMMARY OF THE INVENTION

The present invention is directed to a compound represented by formula I:

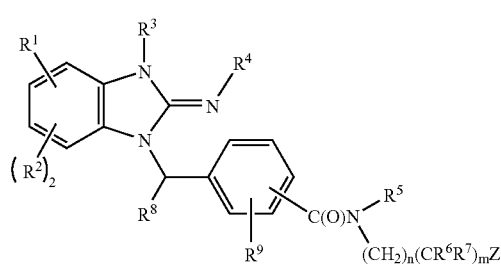

or a pharmaceutically acceptable salt or solvate thereof, wherein:

$R^1$ represents H or is independently selected from the group consisting of:

a) OH, halo, $CO_2R^a$, $C(O)NR^bR^c$, $NR^bR^c$, CN or $S(O)_pR^d$;

b) $C_{1-10}$alkyl, $C_{2-10}$alkenyl, $C_{2-10}$alkynyl, $OC_{1-10}$alkyl, $OC_{3-10}$ alkenyl and $OC_{3-10}$alkynyl, said groups being optionally substituted with:

(1) 1-5 halo groups up to a perhaloalkyl group;

(2) 1 oxo group;

(3) 1-2 OH groups;

(4) 1-2 $C_{1-10}$alkoxy groups, each optionally substituted with: up to five halo or a perhaloalkoxy, 1 OH or $CO^2R^a$ group;

(5) 1 $CO_2R^a$ or $S(O)_pR^d$;

(6) 1-2 Aryl, Hetcy or HAR groups, each optionally substituted as follows:

(a) 1-5 halo groups, (b) 1 OH, $CO_2R^a$, CN, $S(O)_pR^d$, $NO_2$ or $C(O)NR^bR^c$, (c) 1-2 $C_{1-10}$alkyl or alkoxy groups, each optionally substituted with: 1-5 halo, up to perhaloalkyl, and 1-2 OH or $CO_2R^a$ groups; and (d) 1-2 phenyl rings, each of which is optionally substituted as follows: 1-5 halo groups up to perhalo, 1-3 $C_{1-10}$alkyl or alkoxy groups, each being further optionally substituted with 1-5 halo up to perhalo, or 1-2 hydroxy or $CO_2R^a$ groups;

c) Aryl, HAR, Hetcy, —O-Aryl, —O-HAR and —O-Hetcy, each optionally substituted as set forth below:

(1) 1-3 $C_{1-10}$alkyl, $C_{2-10}$alkenyl or $C_{2-10}$alkynyl groups optionally substituted with 1-5 halo groups; 1-2 OH groups; phenyl optionally substituted with 1-3 halo, $C_{1-6}$alkyl or $C_{1-6}$ alkoxy groups, the alkyl and alkoxy groups being further optionally substituted with 1-3 halo groups; $CO_2R^a$; CN or $S(O)_pR^d$ groups; and (2) 1-3 $C_{1-10}$alkoxy groups, the alkyl portion of which is optionally substituted with 1-5 halo groups, 1-2 OH; phenyl optionally substituted with 1-3 halo, $C_{1-6}$alkyl or $C_{1-6}$ alkoxy groups, the alkyl and alkoxy groups being further optionally substituted with 1-3 halo groups;
$CO_2R^a$; CN or $S(O)_pR^d$ groups;

said Aryl, HAR, Hetcy —O-Aryl, —O-HAR and —O-Hetcy group c) being further optionally substituted on carbon by a group selected from the group consisting of:
  (3) 1-5 halo groups;
  (4) 1-2 OH groups;
  (5) 1 $S(O)_pR^d$, $NO_2$ or CN group;
  (6) 1-2 $CO_2R^a$;
  (7) —$C(O)NR^bR^c$;

each $R^2$ represents H or is independently selected from the group consisting of:
a) OH, halo, $CO_2R^a$, $C(O)NR^bR^c$, $NR^bR^c$, CN or $S(O)_pR^d$;
b) $C_{1-10}$alkyl, $C_{2-10}$alkenyl, $C_{2-10}$alkynyl, $OC_{1-10}$alkyl, $OC_{3-10}$ alkenyl and $OC_{3-10}$alkynyl, said groups being optionally substituted with:
  (1) 1-5 halo groups up to a perhaloalkyl group;
  (2) 1 oxo group;
  (3) 1 OH group;
  (4) 1 $C_{1-10}$alkoxy group, each optionally substituted with: up to five halo or a perh loalknxy, 1 OH or $CO_2R^a$ group;
  (5) 1 $CO_2R^a$ or $S(O)_pR^d$;
  (6) 1 Aryl, Hetcy or HAR group, each optionally substituted as follows:
    (a) 1-5 halo groups,
    (b) 1 OH, $CO_2R^a$, CN, $S(O)_pR^d$, $NO_2$ or $C(O)NR^bR^c$,
    (c) 1-2 $C_{1-10}$alkyl or alkoxy groups, each optionally substituted with: 1-5 halo, up to perhaloalkyl, and 1-2 OH or $CO_2R^a$ groups; and
    (d) 1-2 phenyl rings, each of which is optionally substituted as follows: 1-5 halo groups up to perhalo; 1-3 $C_{1-10}$alkyl or alkoxy groups, each being further optionally substituted with 1-5 halo up to perhalo; and 1-2 hydroxy or $CO_2R^a$ groups;
c) Aryl, HAR, Hetcy, —O-Aryl, —O-HAR and —O-Hetcy, each optionally substituted as set forth below:
  (1) 1-3 $C_{1-10}$alkyl, $C_{2-10}$alkenyl or $C_{2-10}$alkynyl groups optionally substituted with 1-5 halo groups, 1-2 OH, phenyl, $CO_2R^a$, CN or $S(O)_pR^d$ groups;
  (2) 1-3 $C_{1-10}$alkoxy groups, the alkyl portion of which is optionally substituted with 1-5 halo groups, 1-2 OH, phenyl, $CO_2R^a$, CN or $S(O)_pR^d$ groups;

said Aryl, HAR or Hetcy group c) being further optionally substituted on carbon by a group selected from the group consisting of:
  (3) 1-5 halo groups up to perhalo;
  (4) 1 OH group;
  (5) 1 $S(O)_pR^d$, $NO_2$ or CN group;
  (6) 1 $CO_2R^a$;

$R^3$ is selected from the group consisting of:
a) $C_{1-10}$alkyl or $C_{2-10}$alkenyl, each optionally substituted with
  1-5 halo groups up to perhalo;
  1-2 OH, $C_{1-3}$alkoxy or halo$C_{1-3}$alkoxy groups;
  1-2 $NR^cR^d$ groups; and
  1-2 Aryl, HAR or Hetcy groups, each optionally substituted with 1-3 halo groups and 1-2 groups selected from CN, $NO_2$, $C_{1-3}$alkyl, halo$C_{1-3}$alkyl, $C_{1-3}$alkoxy and halo$C_{1-3}$alkoxy groups,
b) Aryl, HAR or Hetcy, each optionally substituted with 1-3 halo groups and 1-2 groups selected from CN, $NO_2$, $C_{1-3}$alkyl, halo$C_{1-3}$alkyl, $C_{1-3}$alkoxy and halo$C_{1-3}$ alkoxy groups;

$R^4$ is independently selected from the group consisting of:
Aryl, HAR or Hetcy, each optionally substituted as set forth below:
  (1) 1-3 $C_{1-14}$alkyl, $C_{2-10}$alkenyl or $C_{2-10}$alkynyl groups optionally substituted with 1-5 halo groups, 1-2 OH, $CO_2R^a$, CN or $S(O)_pR^d$ groups or phenyl optionally substituted as follows: 1-5 halo groups up to perhalo; 1-3 $C_{1-10}$alkyl or alkoxy groups, each being further optionally substituted with 1-5 halo up to perhalo, or 1-2 hydroxy or $CO_2R^1$ groups;
  (2) 1-3 $C_{1-10}$alkoxy or $C_{3-10}$alkenyloxy groups, the alkyl portion of which is optionally substituted with 1-5 halo groups, 1-2 OH, $CO_2R^a$, CN, $S(O)_pR^d$, and phenyl optionally substituted as follows: 1-5 halo groups up to perhalo; 1-3 $C_{1-10}$alkyl or alkoxy groups, each being further optionally substituted with 1-5 halo up to perhalo, or 1-2 hydroxy or $CO_2R^a$ groups;
  (3) 1-2 Aryl, HAR or Hetcy, OAryl, OHAR or OHetcy groups, each optionally substituted as follows:
    (i) 1-3 halo groups;
    (ii) 1-2 $C_{1-10}$alkyl, $C_{2-10}$alkenyl or $C_{2-10}$alkynyl groups each optionally substituted with 1-5 halo groups, 1-2 OH, phenyl, $CO_2R^a$, CN or $S(O)_pR^d$ groups;
    (iii) 1-2 $C_{1-10}$alkoxy groups the alkyl portion of which being optionally substituted with 1-5 halo groups, 1-2 OH, phenyl, $CO_2R^a$, CN or $S(O)_pR^d$ groups; and
    (iv) 1-2 $CO_2R^a$, $S(O)_pR^d$, CN, $NR^bR^c$, $NO_2$ or OH groups;

said Aryl, HAR or Hetcy group $R^4$ being further optionally substituted on carbon by a group selected from the group consisting of:
  (4) 1-5 halo groups;
  (5) 1-2 OH groups;
  (6) 1 $S(O)_pR^d$, $NO_2$ or CN group;
  (7) 1-2 $CO_2R^a$;

$R^5$ represents H or $C_{1-6}$alkyl;
$R^6$ is selected from the group consisting of H, OH, F or $C_{1-3}$alkyl;
$R^7$ is H or F, or $R^6$ and $R^7$ are taken in combination and represent oxo;
R8 represents H or $C_{1-6}$alkyl, optionally substituted with OH and 1-5 halo groups up to perhalo;
$R^9$ represents H, halo, OH, $C_{1-6}$alkyl, optionally substituted with 1-5 halo groups up to perhalo, or $C_{1-6}$alkoxy, optionally substituted with 1-3 halo groups up to perhalo,
or when $R^9$ is ortho to the benzylic group, $R^8$ and $R^9$ can be taken together and represent a —$(CH_2)_{2-4}$— or a —O—$(CH_2)_{1-3}$— group;
$R^a$ is H or $C_{1-10}$alkyl, optionally substituted with phenyl, OH, $OC_{1-6}$alkyl, $CO_2H$, $CO_2C_{1-6}$alkyl and 1-3 halo groups;
$R^b$ is H or $C_{1-10}$alkyl;
$R^c$ is H or is independently selected from:
  (a) $C_{1-10}$alkyl, optionally substituted with OH, $OC_{1-6}$ alkyl, $CO_2H$, $CO_2C_{1-6}$alkyl, and 1-3 halo groups;
  (b) Aryl or Ar—$C_{1-6}$alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo;
  (c) Hetcy or Hetcy-$C_{1-6}$alkyl, optionally substituted with 1-5 halo groups and 1-3 groups selected from: oxo, $C_{1-10}$alkyl and $OC_{1-10}$alkyl, said alkyl and alkoxy being further optionally substituted with 1-5 halo groups up to perhalo; and (d) HAR or HAR-$C_{1-6}$alkyl, optionally substituted with 1-5 halo groups and 1-3 groups selected from: $C_{1-10}$alkyl and $OC_{1-10}$alkyl, said alkyl and alkoxy being further optionally substituted with 1-5 halo groups up to perhalo;

$R^d$ is $C_{1-10}$alkyl, Aryl or Ar—$C_{1-10}$alkyl;

m is an integer selected from 0, 1 and 2;

n is an integer selected from 0 to 6;

p is an integer selected from 0, 1 and 2, and when at least one of m and n is other than 0, Z is selected from $CO_2R^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl).

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Alkenyl" means carbon chains which contain at least one carbon-carbon double bond, and which may be linear or branched or combinations thereof. Examples of alkenyl include vinyl, alkyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Aryl" (Ar) means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Heterocyclyl" (Hetcy) means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils). Heterocyclyl-moreover includes such moieties in charged form, e.g., piperidinium.

"Halogen" (Halo) includes fluorine, chlorine, bromine and iodine.

In its broadest aspect, a compound represented by formula I:

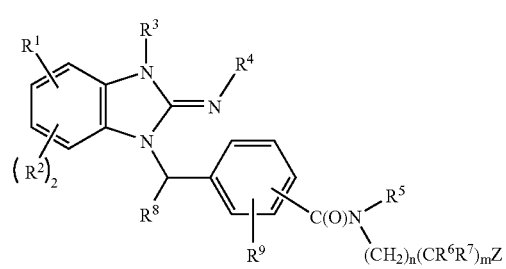

or a pharmaceutically acceptable salt or solvate thereof is disclosed, wherein:

$R^1$ represents H or is independently selected from the group consisting of:

a) OH, halo, $CO_2R^a$, $C(O)NR^bR^c$, $NR^bR^c$, CN or $S(O)_p R^d$;

b) $C_{1-10}$alkyl, $C_{2-10}$alkenyl, $C_{2-10}$alkynyl, $OC_{1-10}$alkyl, $OC_{3-10}$ alkenyl and $OC_{3-10}$alkynyl, said groups being optionally substituted with:

(1) 1-5 halo groups up to a perhaloalkyl group;

(2) 1 oxo group;

(3) 1-2 OH groups;

(4) 1-2 $C_{1-10}$alkoxy groups, each optionally substituted with: up to five halo or a perhaloalkoxy, 1 OH or $CO_2R^a$ group;

(5) 1 $CO_2R^a$ or $S(O)_p R^d$;

(6) 1-2 Aryl, Hetcy or HAR groups, each optionally substituted as follows:

(a) 1-5 halo groups, (b) 1 OH, $CO_2R^a$, CN, $S(O)_p R^d$, $NO_2$ or $C(O)NR^bR^c$, (c) 1-2 $C_{1-10}$alkyl or alkoxy groups, each optionally substituted with: 1-5 halo, up to perhaloalkyl, and 1-2 OH or $CO_2R^a$ groups; and (d) 1-2 phenyl rings, each of which is optionally substituted as follows: 1-5 halo groups up to perhalo, 1-3 $C_{1-10}$alkyl or alkoxy groups, each being further optionally substituted with 1-5 halo up to perhalo, or 1-2 hydroxy or $CO_2R^a$ groups;

c) Aryl, HAR, Hetcy, —O-Aryl, —O-HAR and —O-Hetcy, each optionally substituted as set forth below:

(1) 1-3 $C_{1-10}$alkyl, $C_{2-10}$alkenyl or $C_{2-10}$alkynyl groups optionally substituted with 1-5 halo groups; 1-2 OH groups; phenyl optionally substituted with 1-3 halo, $C_{1-6}$alkyl or $C_{1-6}$ alkoxy groups, the alkyl and alkoxy groups being further optionally substituted with 1-3 halo groups; $CO_2R^a$; CN or $S(O)_p R^d$ groups; and (2) 1-3 $C_{1-10}$alkoxy groups, the alkyl portion of which is optionally substituted with 1-5 halo groups, 1-2 OH; phenyl optionally substituted with 1-3 halo, $C_{1-6}$alkyl or $C_{1-6}$ alkoxy groups, the alkyl and alkoxy groups being further optionally substituted with 1-3 halo groups; $CO_2R^a$; CN or $S(O)_pR^d$ groups;

said Aryl, HAR, Hetcy —O-Aryl, —O-HAR and —O-Hetcy group c) being further optionally substituted on carbon by a group selected from the group consisting of:
  (3) 1-5 halo groups;
  (4) 1-2 OH groups;
  (5) 1 $S(O)_pR^d$, $NO_2$ or CN group;
  (6) 1-2 $CO_2R^a$;
  (7) —$C(O)NR^bR^c$;

each $R^2$ represents H or is independently selected from the group consisting of:
a) OH, halo, $CO_2R^a$, $C(O)NR^bR^c$, $NR^bR^c$, CN or $S(O)_pR^d$;
b) $C_{1-10}$alkyl, $C_{2-10}$alkenyl, $C_{2-10}$alkynyl, $OC_{1-10}$alkyl, $OC_{3-10}$ alkenyl and $OC_{3-10}$alkynyl, said groups being optionally substituted with:
  (1) 1-5 halo groups up to a perhaloalkyl group;
  (2) 1 oxo group;
  (3) 1 OH group;
  (4) 1 $C_{1-10}$alkoxy group, each optionally substituted with: up to five halo or a perhaloalkoxy, 1 OH or $CO_2R^a$ group;
  (5) 1 $CO_2R^a$ or $S(O)_pR^d$;
  (6) 1 Aryl, Hetcy or HAR group, each optionally substituted as follows:
    (a) 1-5 halo groups,
    (b) 1 OH, $CO_2R^a$, CN, $S(O)_pR^d$, $NO_2$ or $C(O)NR^bR^c$,
    (c) 1-2 $C_{1-10}$alkyl or alkoxy groups, each optionally substituted with: 1-5 halo, up to perhaloalkyl, and 1-2 OH or $CO_2R^a$ groups; and
    (d) 1-2 phenyl rings, each of which is optionally substituted as follows: 1-5 halo groups up to perhalo; 1-3 $C_{1-10}$alkyl or alkoxy groups, each being further optionally substituted with 1-5 halo up to perhalo; and 1-2 hydroxy or $CO_2R^a$ groups;
c) Aryl, HAR, Hetcy, —O-Aryl, —O-HAR and —O-Hetcy,- each optionally substituted as set forth below:
  (1) 1-3 $C_{1-10}$alkyl, $C_{2-10}$alkenyl or $C_{2-10}$alkynyl groups optionally substituted with 1-5 halo groups, 1-2 OH, phenyl, $CO_2R^a$, CN or $S(O)_pR^d$ groups;
  (2) 1-3 $C_{1-10}$alkoxy groups, the alkyl portion of which is optionally substituted with 1-5 halo groups, 1-2 OH, phenyl, $CO_2R^a$, CN or $S(O)_pR^d$ groups; said Aryl, HAR or Hetcy group c) being further optionally substituted on carbon by a group consisting of:
  (3) 1-5 halo groups up to perhalo;
  (4) 1 OH group;
  (5) 1 $S(O)_pR^d$, $NO_2$ or CN group;
  (6) 1 $CO_2R^a$;

$R^3$ is selected from the group consisting of:
a) $C_{1-10}$alkyl or $C_{2-10}$alkenyl, each optionally substituted with
  1-5 halo groups up to perhalo;
  1-2 OH, $C_{3-10}$alkoxy or halo$C_{1-3}$alkoxy groups;
  1-2 $NR^cR^d$ groups; and
  1-2 Aryl, HAR or Hetcy groups, each optionally substituted with 1-3 halo groups and 1-2 groups selected from CN, $NO_2$, $C_{1-3}$alkyl, halo$C_{1-3}$alkyl, $C_{1-3}$alkoxy and halo$C_{1-3}$alkoxy groups,
b) Aryl, HAR or Hetcy, each optionally substituted with 1-3 halo groups and 1-2 groups selected from CN, $NO_2$, $C_{1-3}$alkyl, halo$C_{1-3}$alkyl, $C_{1-3}$alkoxy and halo$C_{1-3}$alkoxy groups;

$R^4$ is independently selected from the group consisting of: Aryl, HAR or Hetcy, each optionally substituted as set forth below:
  (1) 1-3 $C_{1-14}$alkyl, $C_{2-10}$alkenyl or $C_{2-10}$alkynyl groups optionally substituted with 1-5 halo groups, 1-2 OH, $CO_2R^a$, CN or $S(O)_pR^d$ groups or phenyl optionally substituted as follows: 1-5 halo groups up to perhalo; 1-3 $C_{1-10}$alkyl or alkoxy groups, each being further optionally substituted with 1-5 halo up to perhalo, or 1-2 hydroxy or $CO_2R^a$ groups;
  (2) 1-3 $C_{1-10}$alkoxy or $C_{3-10}$alkenyloxy groups, the alkyl portion of which is optionally substituted with 1-5 halo groups, 1-2 OH, $CO_2R^a$, CN, $S(O)_pR^d$, and phenyl optionally substituted as follows: 1-5 halo groups up to perhalo; 1-3 $C_{1-10}$alkyl or alkoxy groups, each being further optionally substituted with 1-5 halo up to perhalo, or 1-2 hydroxy or $CO_2R^a$ groups;
  (3) 1-2 Aryl, HAR or Hetcy, OAryl, OHAR or OHetcy groups, each optionally substituted as follows:
    (i) 1-3 halo groups;
    (ii) 1-2 $C_{1-10}$alkyl, $C_{2-10}$alkenyl or $C_{2-10}$alkynyl groups each optionally substituted with 1-5 halo groups, 1-2 OH, phenyl, $CO_2R^a$, CN or $S(O)_pR^d$ groups;
    (iii) 1-2 $C_{1-10}$alkoxy groups the alkyl portion of which being optionally substituted with 1-5 halo groups, 1-2 OH, phenyl, $CO_2R^a$, CN or $S(O)_pR^d$ groups; and
    (iv) 1-2 $CO_2R^a$, $S(O)_pR^d$, CN, $NR^bR^c$, $NO_2$ or OH groups;

said Aryl, HAR or Hetcy group $R^4$ being further optionally substituted on carbon by a group selected from the group consisting of:
  (4) 1-5 halo groups;
  (5) 1-2 OH groups;
  (6) 1 $S(O)_pR^d$, $NO_2$ or CN group;
  (7) 1-2 $CO_2R^a$;

$R^5$ represents H or $C_{1-6}$alkyl;

$R^6$ is selected from the group consisting of H, OH, F or $C_{1-3}$alkyl;

$R^7$ is H or F, or $R^6$ and $R^7$ are taken in combination and represent oxo;

$R^8$ represents H or $C_{1-6}$alkyl, optionally substituted with OH and 1-5 halo groups up to perhalo;

$R^9$ represents H, halo, OH, $C_{1-6}$alkyl, optionally substituted with 1-5 halo groups up to perhalo, or $C_{1-6}$alkoxy, optionally substituted with 1-3 halo groups up to perhalo, or when $R^9$ is ortho to the benzylic group, $R^8$ and $R^9$ can be taken together and represent a —$(CH_2)_{2-4}$— or a —O—$(CH_2)_{1-3}$— group;

$R^a$ is H or C, loalkyl, optionally substituted with phenyl, OH, $OC_{1-6}$alkyl, $CO_2H$, $CO_2C_{1-6}$alkyl and 1-3 halo groups;

$R^b$ is H or $C_{1-10}$alkyl;

$R^c$ is H or is independently selected from:
  (a) $C_{1-10}$alkyl, optionally substituted with OH, $OC_{1-6}$alkyl, $CO_2H$, $CO_2C_{1-6}$alkyl, and 1-3 halo groups;
  (b) Aryl or Ar—$C_{1-6}$alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo;
  (c) Hetcy or Hetcy-$C_{1-6}$alkyl, optionally substituted with 1-5 halo groups and 1-3 groups selected from: oxo, $C_{1-10}$alkyl and $OC_{1-10}$alkyl, said alkyl and alkoxy being further optionally substituted with 1-5 halo groups up to perhalo; and (d) HAR or HAR-$C_{1-6}$alkyl, optionally substituted with 1-5 halo groups and 1-3 groups selected from: $C_{1-10}$alkyl and $OC_{1-10}$alkyl, said alkyl and alkoxy being further optionally substituted with 1-5 halo groups up to perhalo;

$R^d$ is $C_{1-10}$alkyl, Aryl or Ar—$C_{1-10}$alkyl;

m is an integer selected from 0, 1 and 2;

n is an integer selected from 0 to 6;

p is an integer selected from 0, 1 and 2, and when at least one of m and n is other than 0, Z is selected from $CO_2R^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl).

One aspect of the invention that is of interest relates to a compound of formula I or a pharmaceutically acceptable salt or solvate there of, wherein $R^1$ is selected from the group consisting of: H, halo, $C_{1-10}$alkyl and $OC_{1-10}$alkyl, said alkyl and O-alkyl groups being optionally substituted with 1-5 halo groups up to a perhaloalkyl or perhaloalkoxy. Within this subset, all other variables are as originally defined with respect to formula I.

More particularly, an aspect of the invention that is of interest relates to compounds of formula I or a pharmaceutically acceptable salt or solvate thereof, wherein $R^1$ is selected from the group consisting of: H, halo, C1-4 alkyl, C1-4 alkoxy, said alkyl and alkoxy being optionally substituted with 1-3 halo groups. Within this subset, all other variables are as originally defined with respect to formula I.

Another aspect of the invention that is of interest relates to compounds of formula I wherein each $R^2$ represents H or is independently selected from the group consisting of:

a) halo or $S(O)_pR^d$; wherein p is 2 and $R^d$ represents $C_{1-10}$alkyl;

b) $C_{1-10}$alkyl, $C_{2-10}$alkenyl, $OC_{1-10}$alkyl and $OC_{3-10}$alkenyl, said groups being optionally substituted with:
 (1) 1-5 halo groups up to a perhaloalkyl group;
 (2) 1 $C_{1-10}$alkoxy group, each optionally substituted with: up to five halo or perhaloalkoxy, 1 OH or $CO_2R^a$ group;
 (3) 1 Aryl or HAR group, each optionally substituted as follows:
  (a) 1-5 halo groups,
  (b) 1-2 $C_{1-10}$alkyl or alkoxy groups, each optionally substituted with: 1-5 halo, up to perhaloalkyl, and 1-2 OH or $CO_2R^a$ groups;

c) Aryl or HAR, each optionally substituted with:
 (1) 1-2 $C_{1-10}$alkyl groups optionally substituted with 1-5 halo groups;
 (2) 1-2 $C_{1-10}$alkoxy groups, the alkyl portion of which is optionally substituted with 1-5 halo groups;

said Aryl or HAR being further optionally substituted on carbon by 1-3 halo groups; up to perhalo. Within this subset, all other variables are as originally defined with respect to formula I.

More particularly, an aspect of the invention that is of interest relates to compounds of formula I wherein one $R^2$ group represents H and the other represents H or is selected from the group consisting of:

a) halo or $S(O)_pR^d$; wherein p is 2 and $R^d$ represents $C_{1-10}$-alkyl;

b) $C_{1-10}$alkyl, $C_{2-10}$alkenyl, $OC_{1-10}$alkyl or $OC_{3-10}$alkenyl, said groups being optionally substituted with:
 (1) 1-5 halo groups up to a perhaloalkyl group;
 (2) 1 $C_{1-10}$alkoxy group, each optionally substituted with: up to five halo or a perhaloalkoxy, 1 OH or $CO_2R^a$ group;
 (3) 1 Aryl or HAR group, each optionally substituted as follows:
  (a) 1-5 halo groups,
  (b) 1-2 $C_{1-10}$alkyl or alkoxy groups, each optionally substituted with: 1-5 halo, up to perhaloalkyl, and 1-2 OH or $CO_2R^a$ groups;

c) Aryl or HAR, each optionally substituted with:
 (1) 1-2 $C_{1-10}$alkyl groups optionally substituted with 1-5 halo groups;
 (2) 1-2 $C_{1-10}$alkoxy groups, the alkyl portion of which is optionally substituted with 1-5 halo groups;

said Aryl or HAR being further optionally substituted on carbon by 1-3 halo groups; up to perhalo. Within this subset, all other variables are as originally defined with respect to formula I.

Even more particularly, an aspect of the invention that is of interest relates to a compound of formula I wherein:

one $R^2$ group represents H and the other represents H or a member selected from the group consisting of:

a) halo or $S(O)_pR^d$; wherein p is 2 and $R^d$ represents $C_{1-2}$alkyl;

b) $C_{1-4}$alkyl, $C_{2-4}$alkenyl, $OC_{1-4}$alkyl or $OC_{3-4}$alkenyl, said groups being optionally substituted with:
 (1) 1-5 halo groups up to a perhaloalkyl group;
 (2) 1 $C_{1-4}$alkoxy group, optionally substituted with: up to 3 halo or a perhaloalkoxy group;
 (3) 1 Aryl or HAR group, each optionally substituted as follows:
  (a) 1-3 halo groups,
  (b) 1 $C_{1-4}$alkyl or alkoxy group, each optionally substituted with: 1-3 halo, up to perhaloalkyl, groups;

c) Aryl or HAR, each optionally substituted with:
 (1) 1-2 $C_{1-4}$alkyl groups optionally substituted with 1-3 halo groups;
 (2) 1-2 $C_{1-4}$alkoxy groups, the alkyl portion of which is optionally substituted with 1-3 halo groups;

said Aryl or HAR being further optionally substituted on carbon by 1-3 halo groups; up to perhalo. Within this subset, all other variables are as originally defined with respect to formula I.

Another aspect of the invention that is of interest relates to compounds of formula I wherein $R^3$ is selected from the group consisting of:

a) $C_{1-6}$alkyl optionally substituted with:
 1-3 halo groups up to perhalo;
 1 OH, $C_{1-3}$alkoxy or halo$C_{1-3}$alkoxy group;
 1 $NR^cR^d$ group; and
 1 Aryl or HAR group, each optionally substituted with 1-3 halo groups and 1-2 groups selected from $C_{1-3}$alkyl, halo$C_{1-3}$alkyl, $C_{1-3}$alkoxy and halo$C_{1-3}$alkoxy groups, b) Aryl or HAR, each optionally substituted with 1-3 halo groups and 1-2 groups selected from $C_{1-3}$alkyl, halo$C_{1-3}$ alkyl, $C_{1-3}$alkoxy and halo$C_{1-3}$alkoxy groups. Within this subset, all other variables are as originally defined with respect to formula I.

More particularly, an aspect of the invention that is of interest relates to compounds of formula I wherein $R^3$ is selected from the group consisting of:

a) $C_{1-6}$alkyl optionally substituted with:
 1-3 halo groups up to perhalo;
 1 $C_{1-3}$alkoxy or halo$C_{1-3}$alkoxy group,
 1 $NR^cR^d$ group; wherein $R^c$ and $R^d$ are independently selected from H, $C_{1-3}$alkyl and phenyl; and 1 Aryl or HAR group, each optionally substituted with 1-3 halo groups and 1-2 groups selected from $C_{1-3}$alkyl, halo$C_{1-3}$alkyl, $C_{1-3}$alkoxy and halo$C_{1-3}$alkoxy groups, b) Aryl or HAR, each optionally substituted with 1-3 halo groups and 1 group selected from: $C_{1-3}$alkyl, halo$C_{1-3}$alkyl, $C_{1-3}$alkoxy and halo$C_{1-3}$alkoxy. Within this subset, all other variables are as originally defined with respect to formula I.

Another aspect of the invention that is of interest relates to compounds of formula I or a pharmaceutically acceptable salt or solvate thereof, wherein:

$R^4$ represents an Aryl or HAR group, each optionally substituted as set forth below:
  (1) 1-2 $C_{1-10}$alkyl or $C_{2-10}$alkenyl groups, which are optionally substituted with 1-3 halo groups, or phenyl optionally substituted with 1-2 halo, $C_{1-4}$alkyl or alkoxy groups, each being further optionally substituted with 1-3 halo groups;
  (2) 1-2 $C_{1-10}$alkoxy or $C_{3-10}$alkenyloxy groups, which are optionally substituted with 1-3 halo groups, 1-2 OH or $S(O)_pR^d$, and phenyl optionally substituted as follows: 1-3 halo groups up to perhalo; 1-2 $C_{1-6}$alkyl or alkoxy groups, each being further optionally substituted with 1-3 halo up to perhalo, or 1-2 hydroxy or $CO_2R^a$ groups;
  (3) 1-2 Aryl, HAR or Hetcy, OAryl, OHAR or OHetcy groups, each optionally substituted as follows:
    (i) 1-3 halo groups;
    (ii) 1-2 $C_{1-3}$alkyl or $C_{2-4}$alkenyl groups each optionally substituted with 1-3 halo groups, and 1 of OH, phenyl, $CO_2R^a$, CN and $S(O)_pR^d$;
    (iii) 1-2 $C_{1-3}$alkoxy groups the alkyl portion of which being optionally substituted with 1-3 halo groups, and 1 of OH, phenyl, $CO_2R^a$, CN or $S(O)_pR^d$; and
    (iv) 1-2 $CO_2R^a$, $S(O)_pR^d$, CN, $NR^bR^c$, $NO_2$ or OH groups;

said Aryl, HAR or Hetcy group $R^4$ being further optionally substituted on carbon by a group selected from the group consisting of:
  (4) 1-5 halo groups;
  (5) 1-2 OH groups;
  (6) 1 $S(O)_pR^d$, $NO_2$ or CN group. Within this subset, all other variables are as originally defined with respect to formula I.

In another aspect of the invention that is of interest, $R^5$ represents H or $CH_3$. Within this subset, all other variables are as originally defined with respect to formula I.

In another aspect of the invention that is of interest, $R^8$ is selected from the group consisting of H and $C_{1-3}$alkyl. Within this subset, all other variables are as originally defined with respect to formula I.

In another aspect of the invention that is of interest, $R^6$ and $R^7$ represent H. Within this subset, all other variables are as originally defined with respect to formula I.

In another aspect of the invention that is of interest, $R^9$ represents H. Within this subset, all other variables are as originally defined with respect to formula I.

In another aspect of the invention that is of interest, m is 0 and n is an integer selected from 0 to 2. Within this subset, all other variables are as originally defined with respect to formula I.

In another aspect of the invention when n is 1 or 2, Z is selected from $CO_2R^a$ and 5-tetrazolyl, when both m and n are 0, Z is 5-tetrazolyl. Within this subset, all other variables are as originally defined with respect to formula I.

More particularly, an aspect of the invention that is of interest relates to a compound of formula I or a pharmaceutically acceptable salt or solvate there of, wherein:

$R^1$ is selected from the group consisting of: H, halo, $C_{1-10}$alkyl and $OC_{1-10}$alkyl, said alkyl and O-alkyl groups being optionally substituted with 1-5 halo groups up to a perhaloalkyl or perhaloalkoxy;

each $R^2$ represents H or is independently selected from the group consisting of:
  a) halo or $S(O)_pR^d$; wherein p is 2 and $R^d$ represents $C_{1-10}$alkyl;
  b) $C_{1-10}$alkyl, $C_{2-10}$alkenyl, $OC_{1-10}$alkyl and $OC_{3-10}$alkenyl, said groups being optionally substituted with:
    (1) 1-5 halo groups up to perhaloalkyl;
    (2) 1 $C_{1-10}$alkoxy group, each optionally substituted with: up to five halo or perhaloalkoxy, 1 OH or $CO_2R^a$ group;
    (3) 1 Aryl or HAR group, each optionally substituted as follows:
      (a) 1-5 halo groups,
      (b) 1-2 $C_{1-10}$alkyl or alkoxy groups, each optionally substituted with: 1-5 halo, up to perhaloalkyl, and 1-2 OH or $CO_2R^a$ groups;
  c) Aryl or HAR, each optionally substituted with:
    (1) 1-2 $C_{1-10}$alkyl groups optionally substituted with 1-5 halo groups;
    (2) 1-2 $C_{1-10}$alkoxy groups, the alkyl portion of which is optionally substituted with 1-5 halo groups;

said Aryl or HAR being further optionally substituted on carbon by 1-3 halo groups; up to perhalo;

$R^3$ is selected from the group consisting of:
  a) $C_{1-6}$alkyl optionally substituted with:
    1-3 halo groups up to perhalo;
    1 OH, $C_{1-3}$alkoxy or halo$C_{1-3}$alkoxy group;
    1 $NR^cR^d$ group; and
    1 Aryl or HAR group, each optionally substituted with 1-3 halo groups and 1-2 groups selected from $C_{1-3}$alkyl, halo$C_{1-3}$alkyl, $C_{1-3}$alkoxy and halo$C_{1-3}$alkoxy;
  b) Aryl or HAR, each optionally substituted with 1-3 halo groups and 1-2 groups selected from $C_{1-3}$alkyl, halo$C_{1-3}$ alkyl, $C_{1-3}$alkoxy and halo$C_{1-3}$alkoxy;

$R^4$ represents an Aryl or HAR group, each optionally substituted as set forth below:
  (1) 1-2 $C_{1-10}$alkyl or $C_{2-10}$alkenyl groups, which are optionally substituted with 1-3 halo groups, or phenyl optionally substituted with 1-2 halo, $C_{1-4}$alkyl or alkoxy groups, each being further optionally substituted with 1-3 halo groups;
  (2) 1-2 $C_{1-10}$alkoxy or $C_{3-10}$alkenyloxy groups, which are optionally substituted with 1-3 halo groups, 1-2 OH or $S(O)_pR^d$, and phenyl optionally substituted as follows: 1-3 halo groups up to perhalo; 1-2 $C_{1-6}$alkyl or alkoxy groups, each being further optionally substituted with 1-3 halo up to perhalo, or 1-2 hydroxy or $CO_2R^a$ groups;
  (3) 1-2 Aryl, HAR or Hetcy, OAryl, OHAR or OHetcy groups, each optionally substituted as follows:
    (i) 1-3 halo groups;
    (ii) 1-2 $C_{1-3}$alkyl or $C_{2-4}$alkenyl groups each optionally substituted with 1-3 halo groups, and 1 of OH, phenyl, $CO_2R^a$, CN and $S(O)_pR^d$;
    (iii) 1-2 $C_{1-3}$alkoxy groups the alkyl portion of which being optionally substituted with 1-3 halo groups, and 1 of OH, phenyl, $CO_2R^a$, CN and $S(O)_pR^d$; and (iv) 1-2 $CO_2R^a$, $S(O)_pR^d$, CN, $NR^bR^c$, $NO_2$ or OH groups;

said Aryl, HAR or Hetcy group $R^4$ being further optionally substituted on carbon by a group selected from the group consisting of;
(4) 1-5 halo groups;
(5) 1-2 OH groups;
(6) 1 $S(O)_pR^d$, $NO_2$ or CN group;

$R^5$ represents H or $CH_3$;

$R^8$ is selected from the group consisting of H and $C_{1-3}$alkyl;

$R^6$, $R^7$ and $R^9$ represents H;

m is 0 and n is an integer selected from 0 to 2, such that when n is 1 or 2, Z is selected from $CO_2R^a$ and 5-tetrazolyl, and when both m and n are 0, Z is 5-tetrazolyl. Within this subset, all other variables are as originally defined with respect to formula I.

Examples of compounds that fall within the present invention include the following:

TABLE 1

1
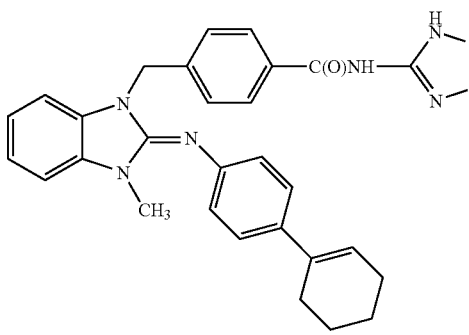

2
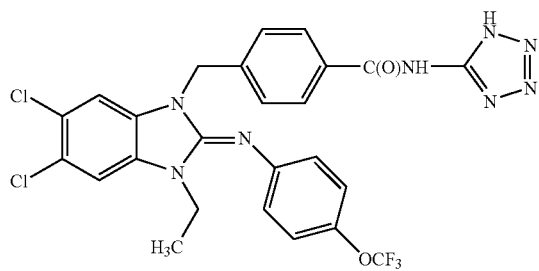

3
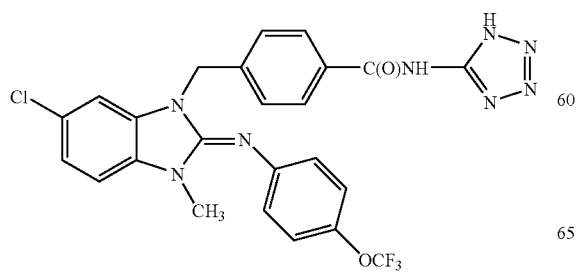

TABLE 1-continued

4
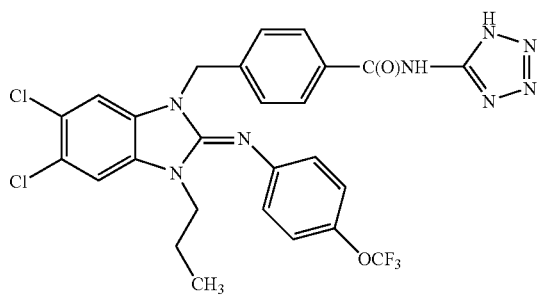

5
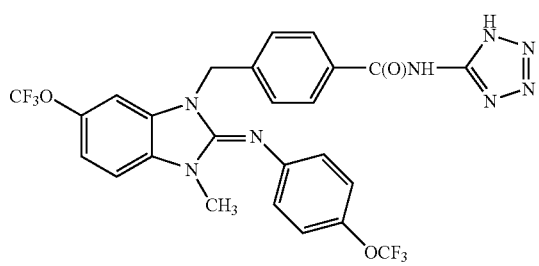

6
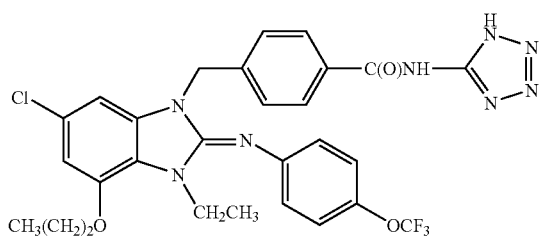

7
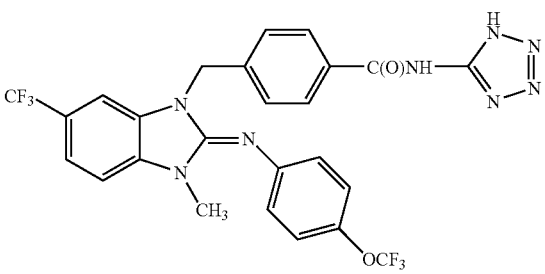

8
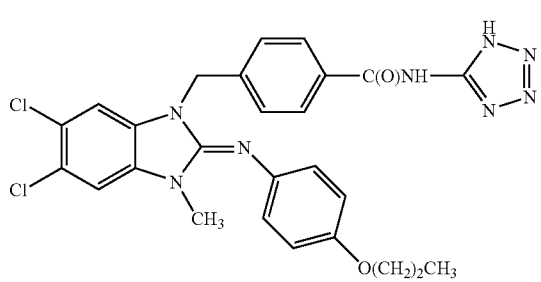

TABLE 1-continued
9
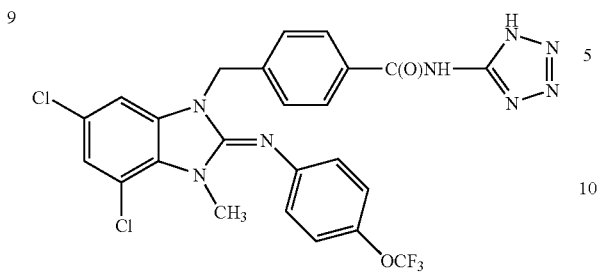
10
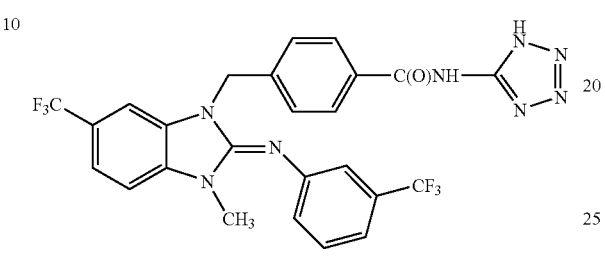
11
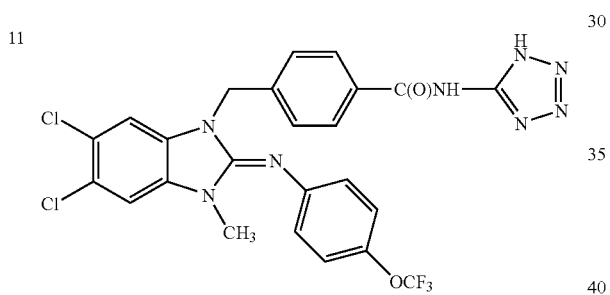
12
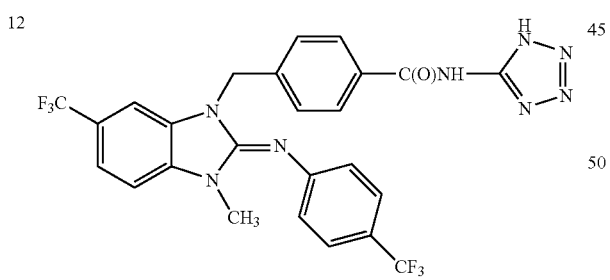
13
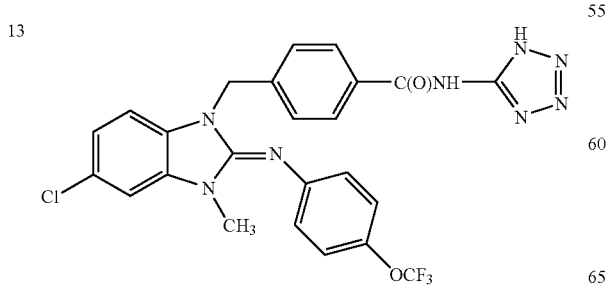
TABLE 1-continued
14
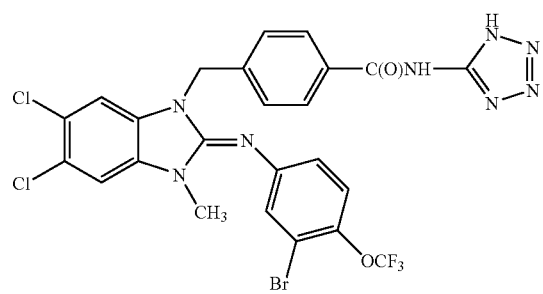
15
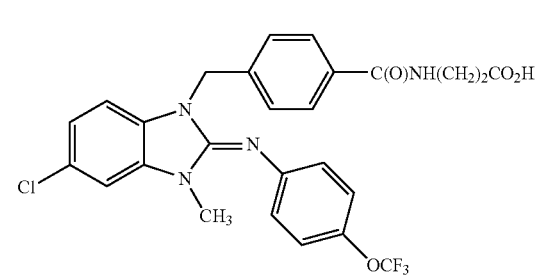
16
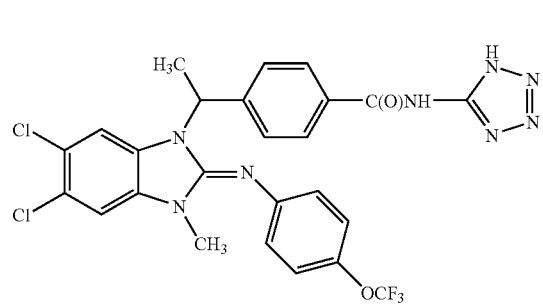
17
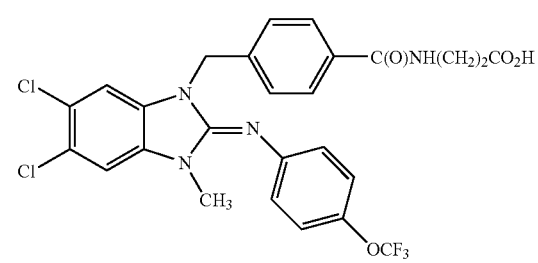
18
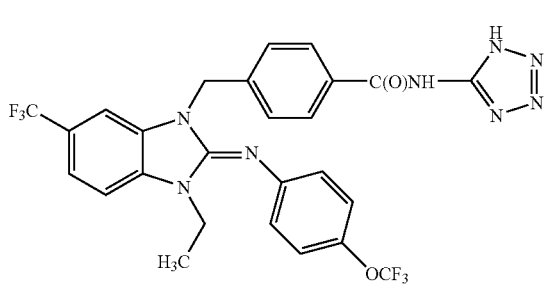

TABLE 1-continued
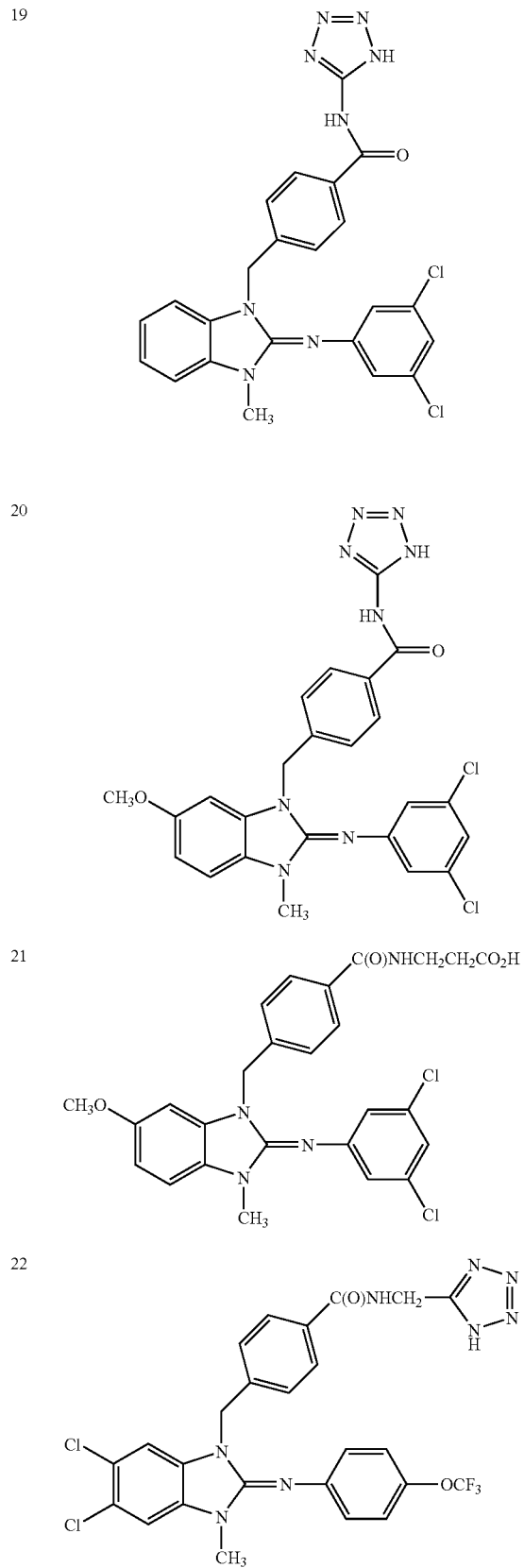
TABLE 1-continued
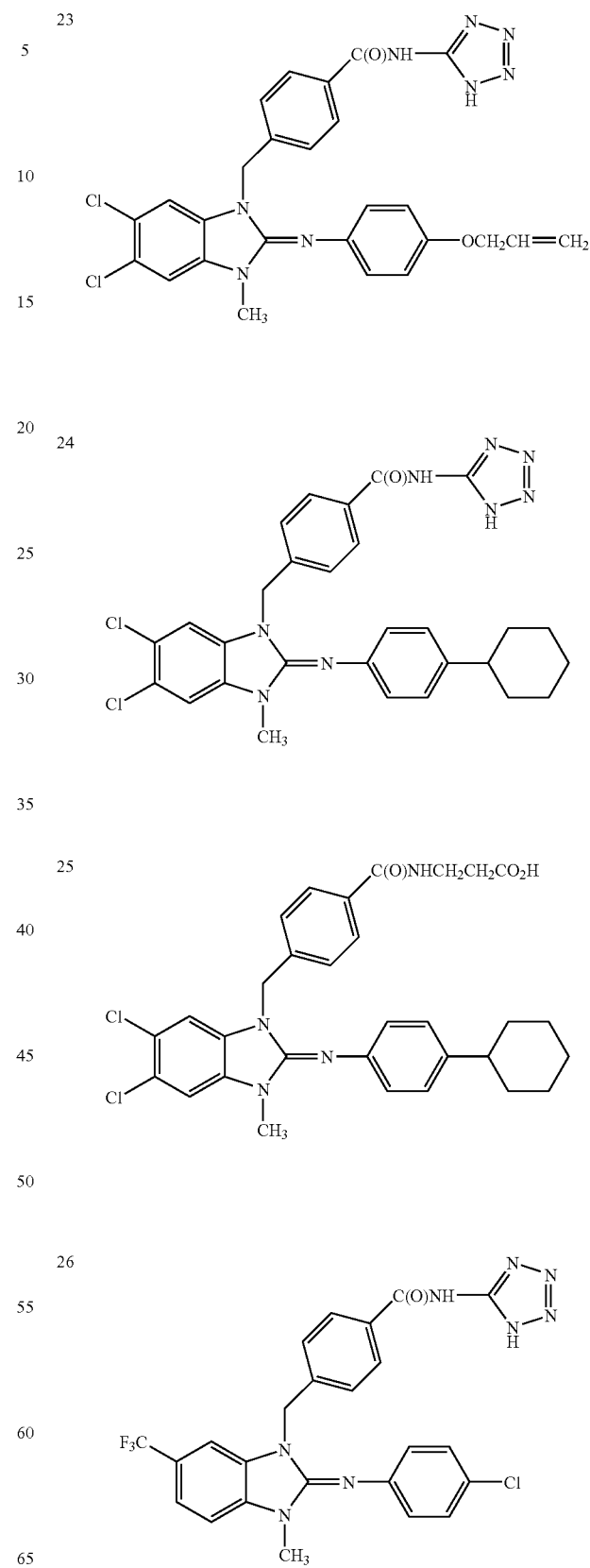

TABLE 1-continued
| 27 | 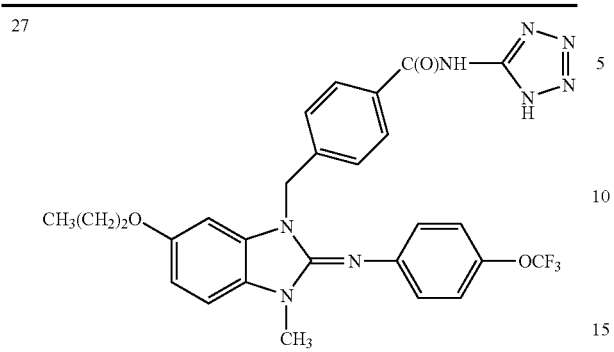 |
|---|---|
| 28 | 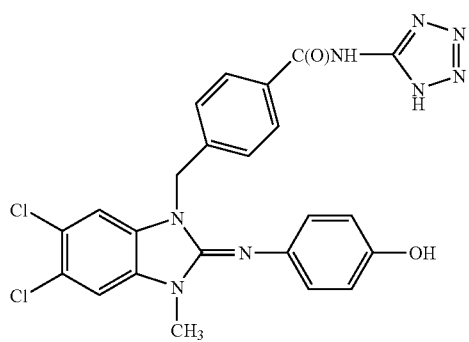 |
| 29 | 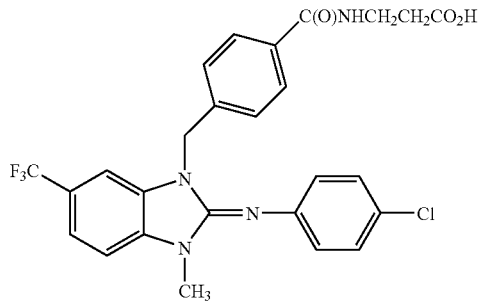 |
| 30 | 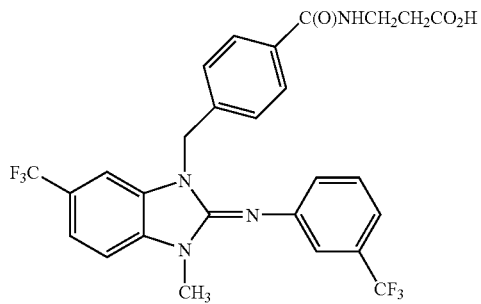 |
TABLE 1-continued
| 31 | 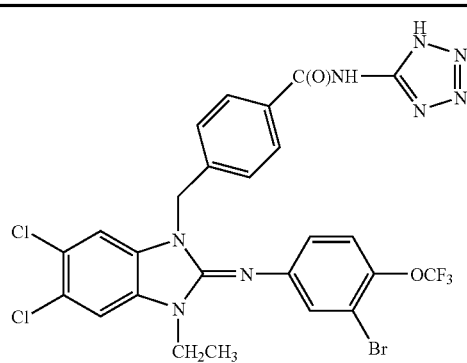 |
|---|---|
| 32 | 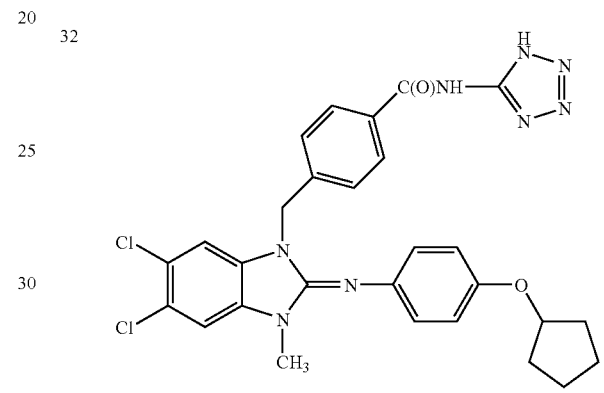 |
| 33 | 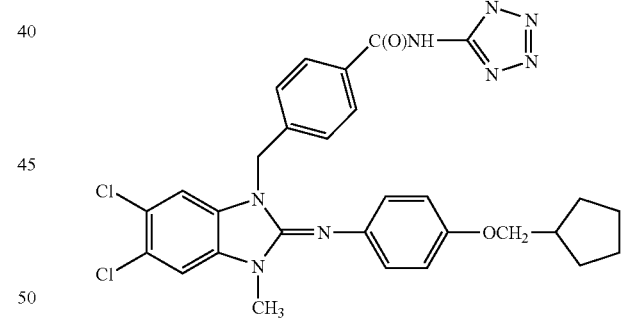 |
| 34 | 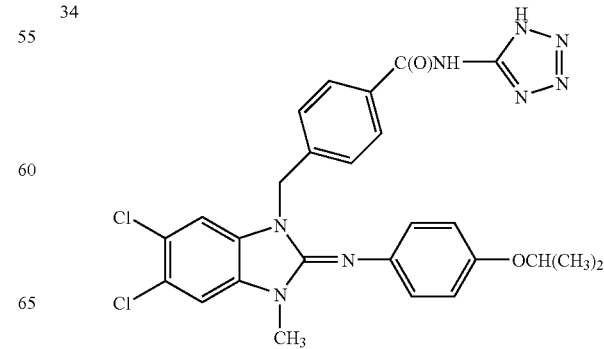 |

TABLE 1-continued
| 35 | 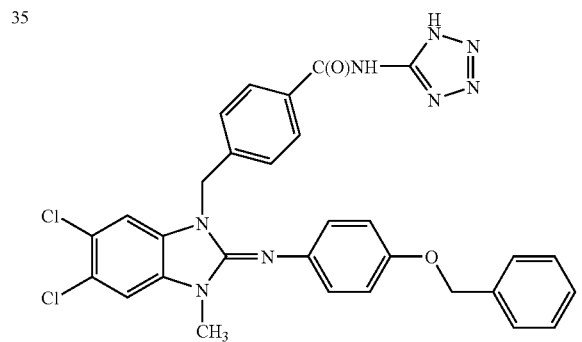 |
|---|---|
| 36 | 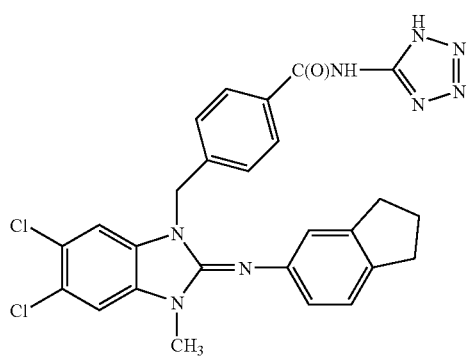 |
| 37 | 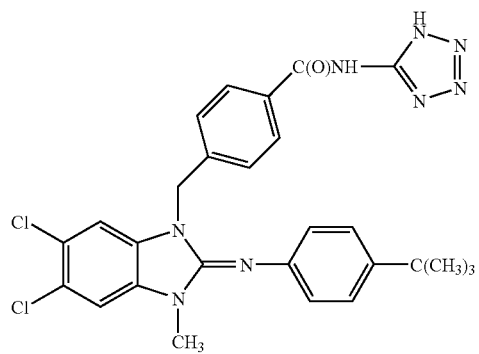 |
| 38 | 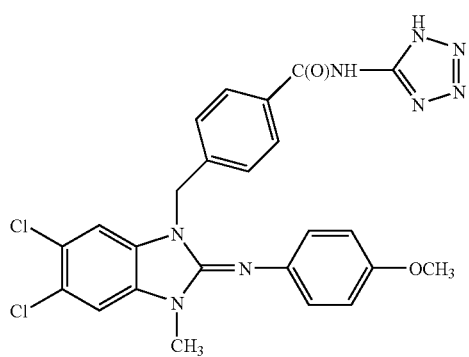 |
TABLE 1-continued
| 39 | 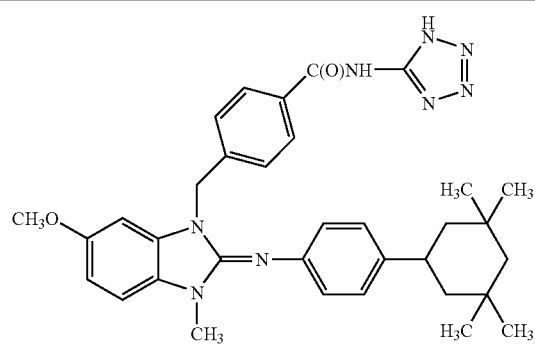 |
|---|---|
| 40 | 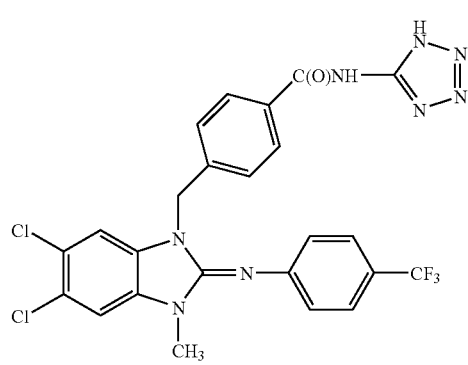 |
| 41 | 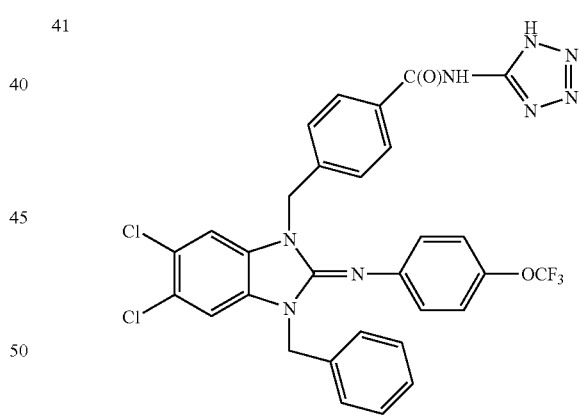 |
| 42 | 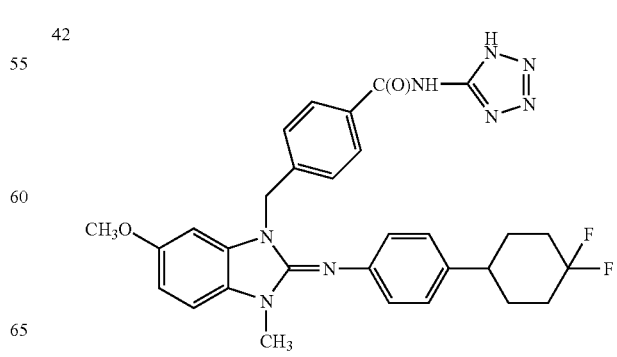 |

TABLE 1-continued
43 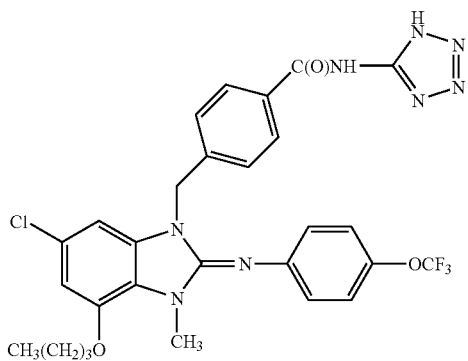
44 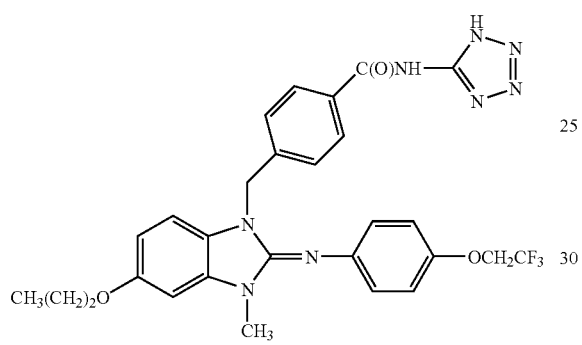
45 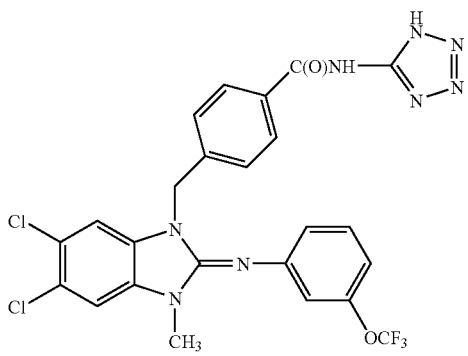
46 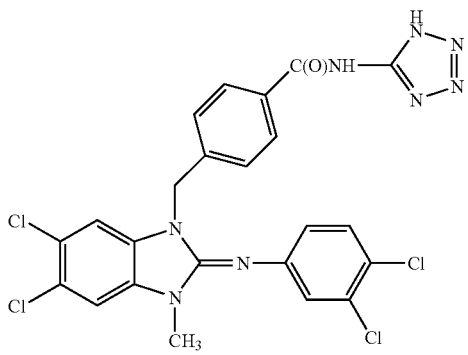
47 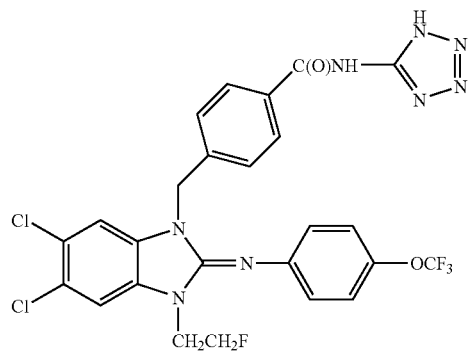
48 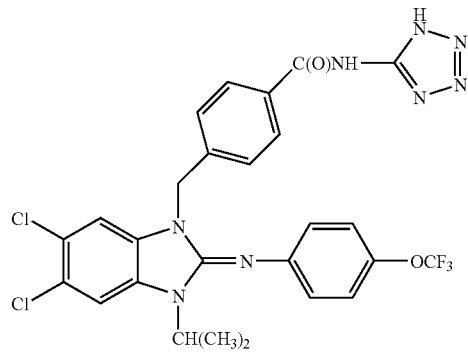
49 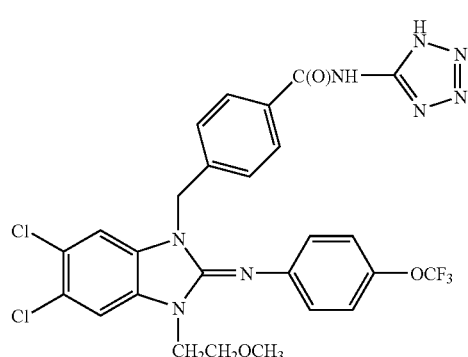
50 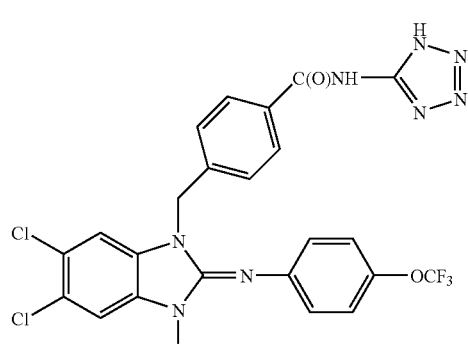

TABLE 1-continued
51
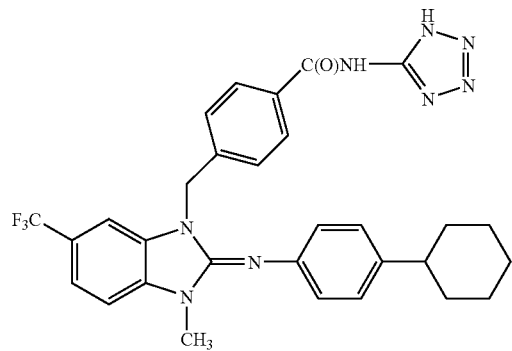
52
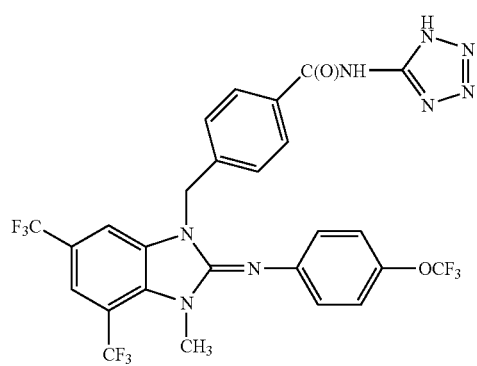
53
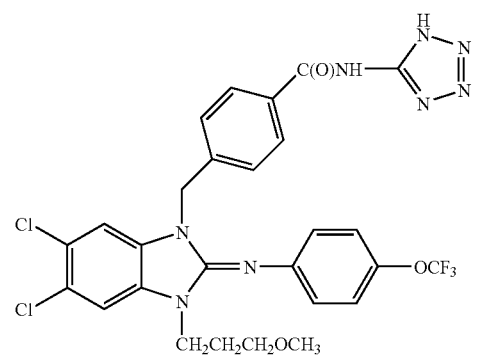
54
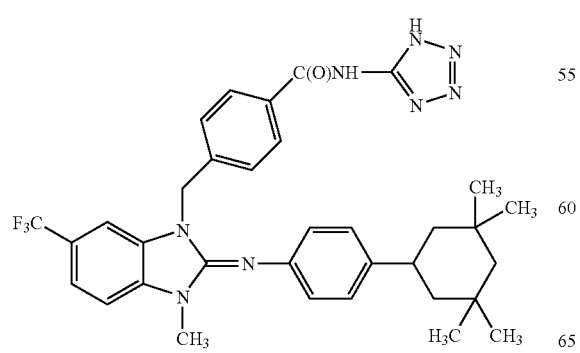
TABLE 1-continued
55
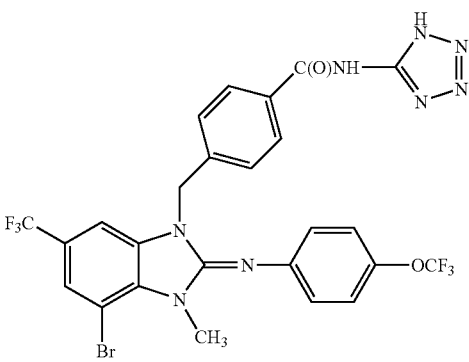
56
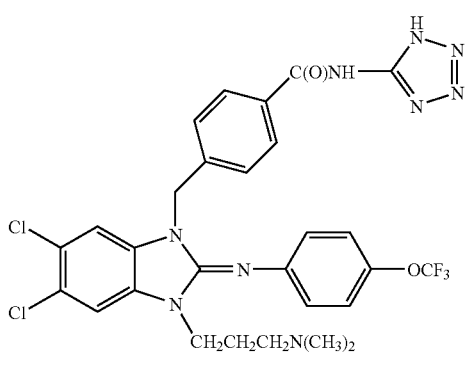
57
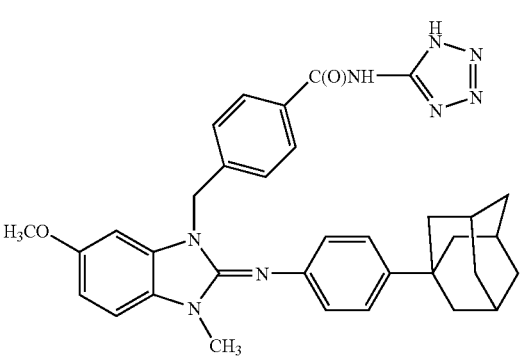
58
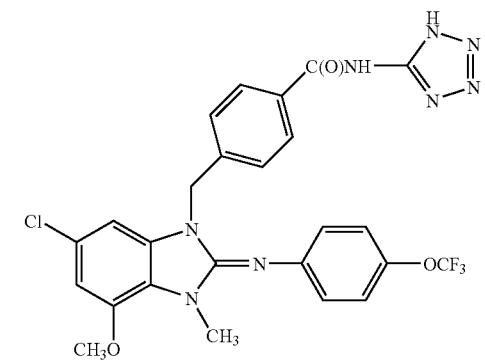

TABLE 1-continued
59 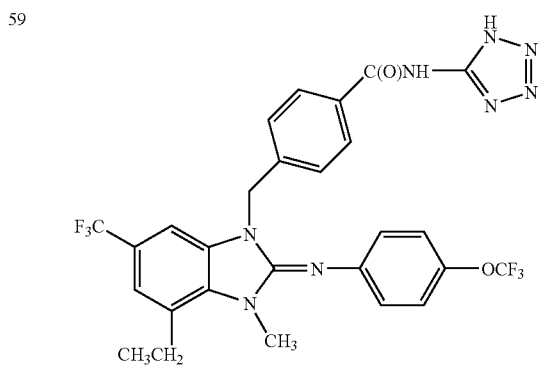
60 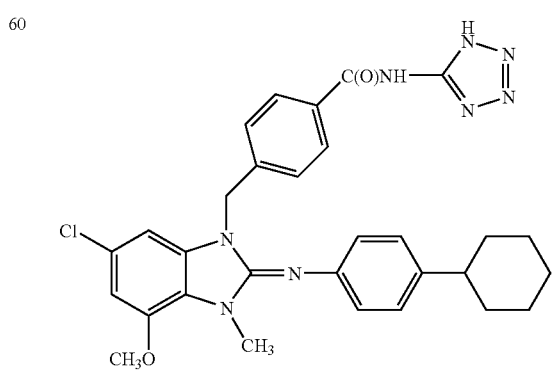
61 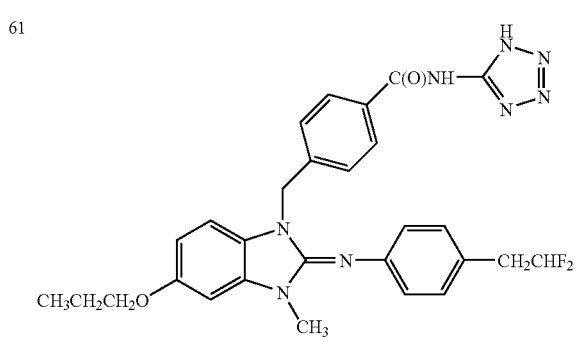
62 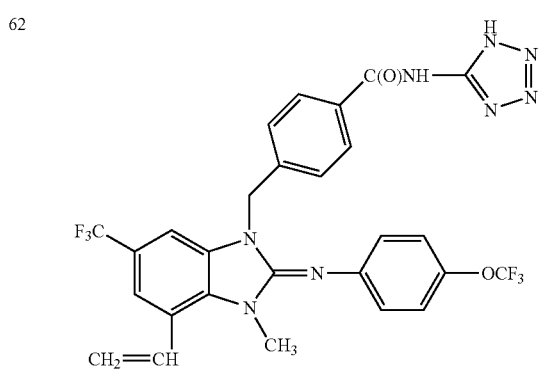
TABLE 1-continued
63 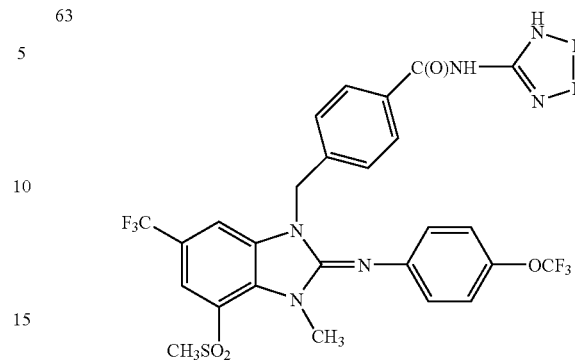
64 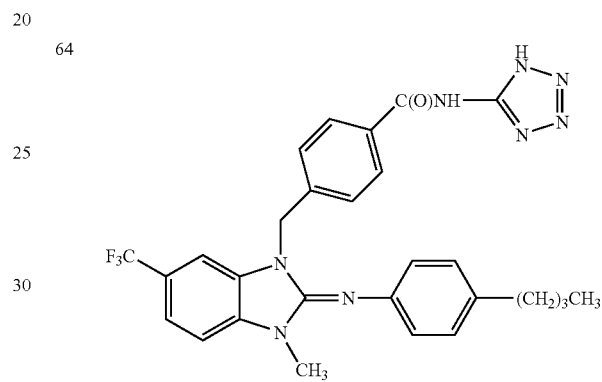
65 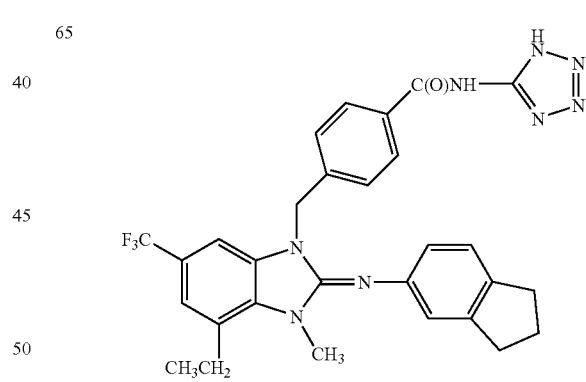
66 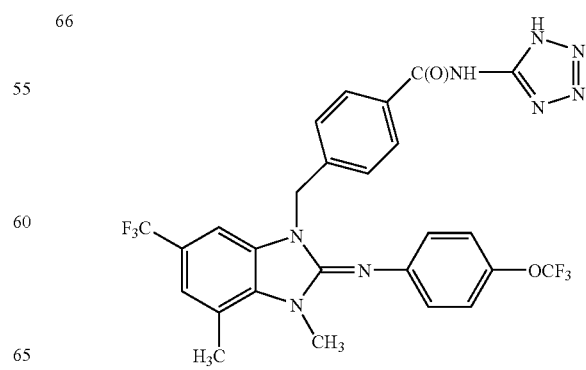

TABLE 1-continued
67 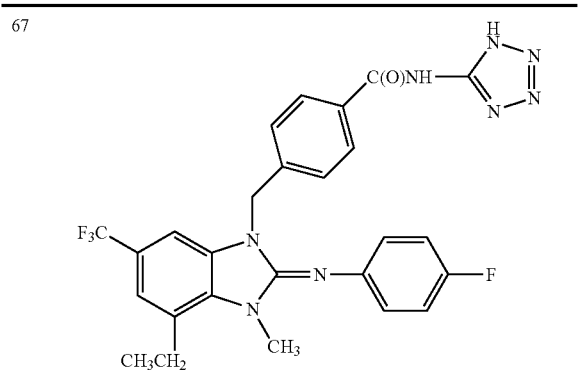
68 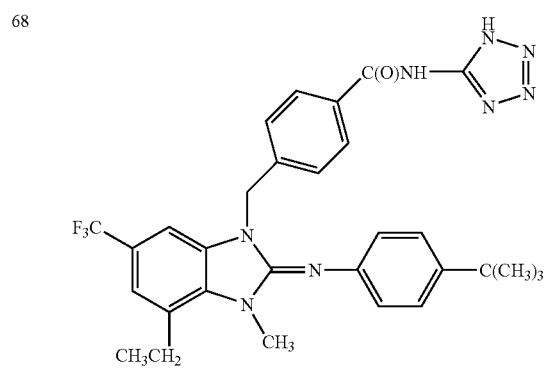
69 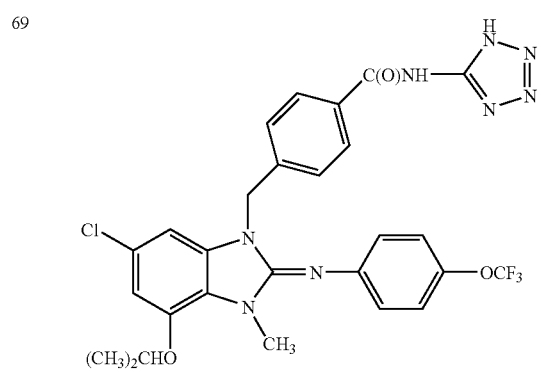
70 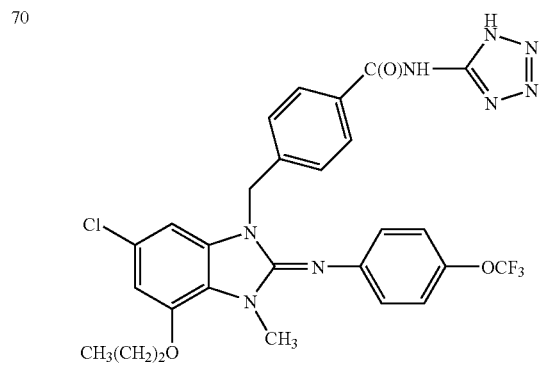
71 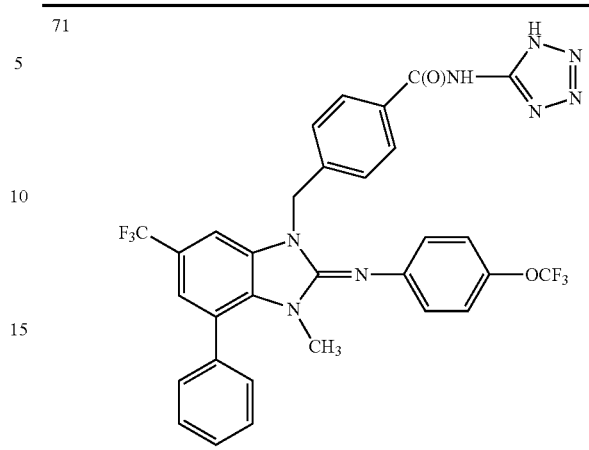
72 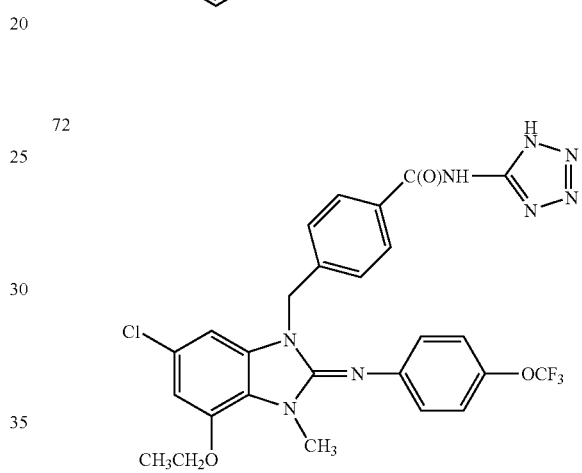
73 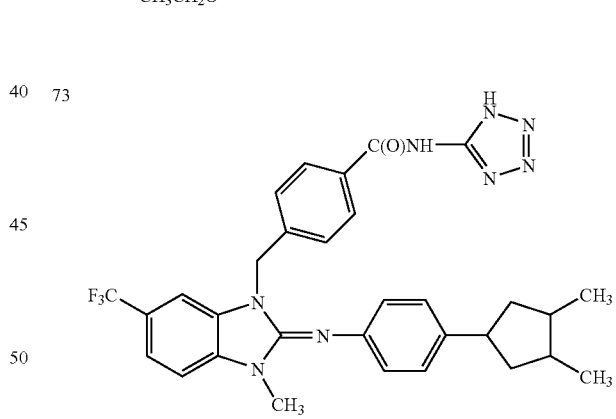
74 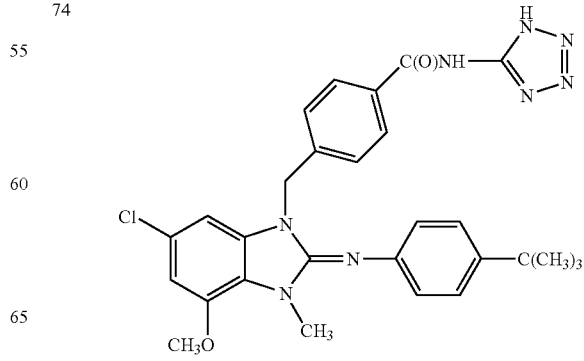

TABLE 1-continued
75
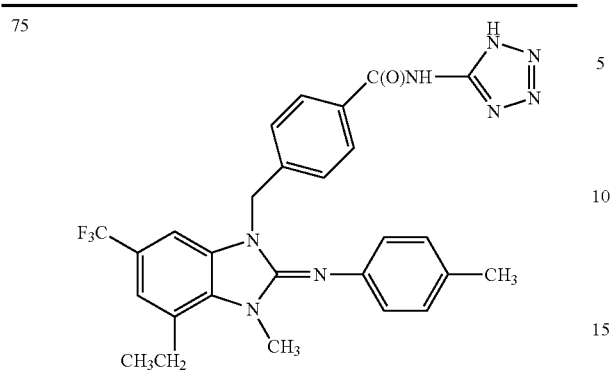
76
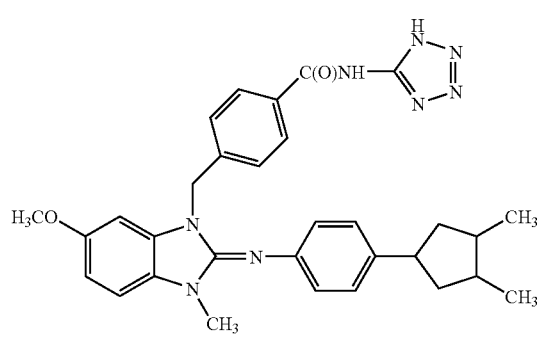
77
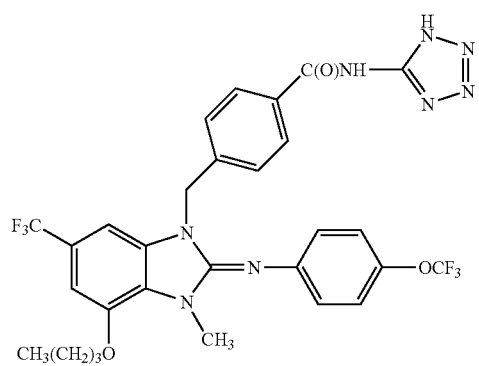
78
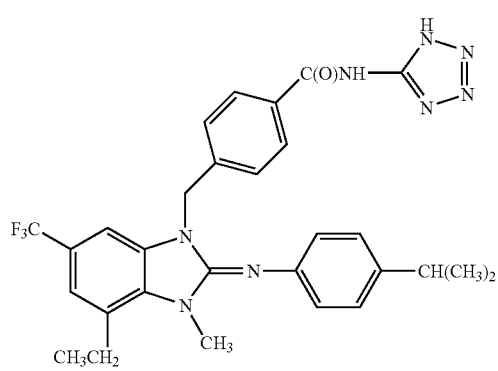
TABLE 1-continued
79
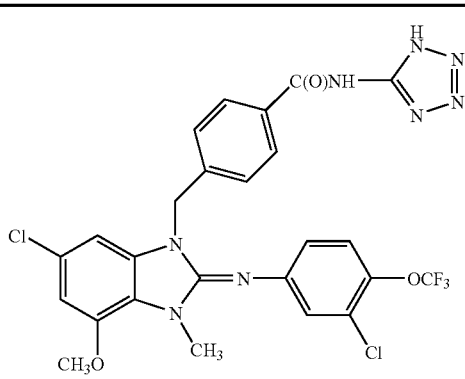
80
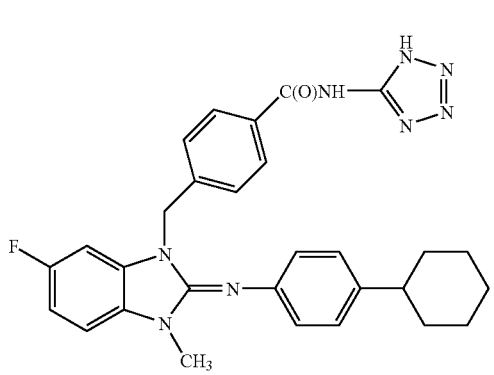
81
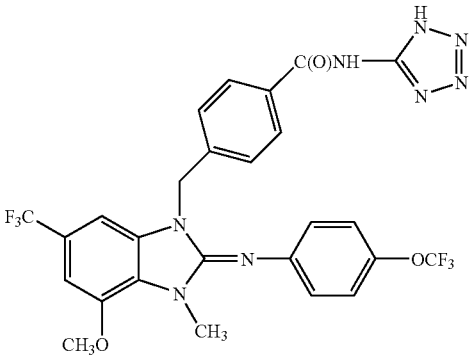
82
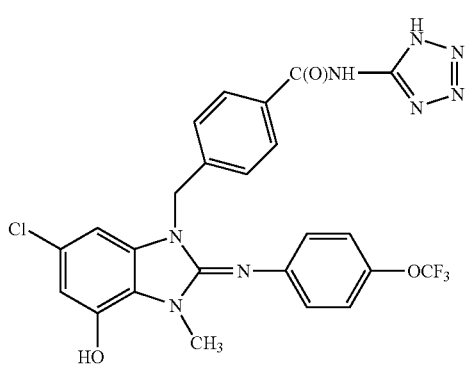

TABLE 1-continued
83
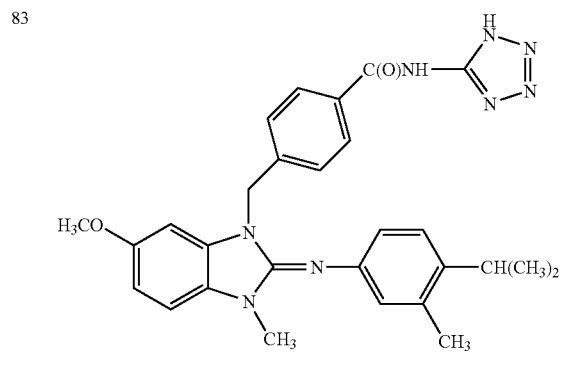
84
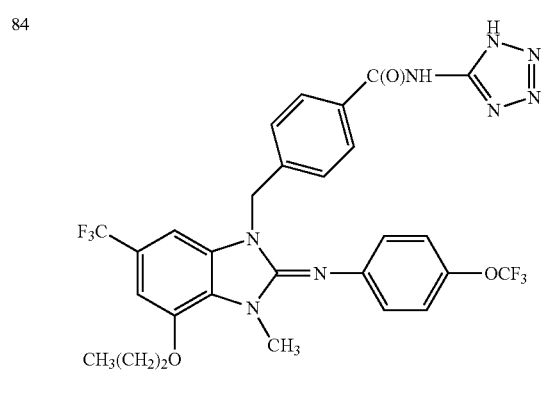
85
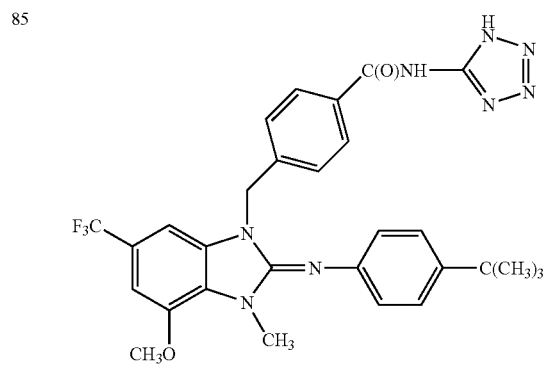
86
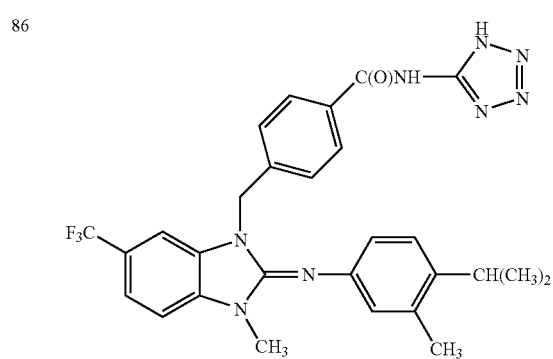
TABLE 1-continued
87
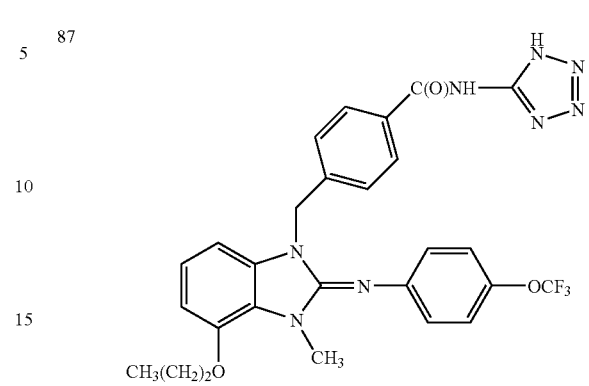
88
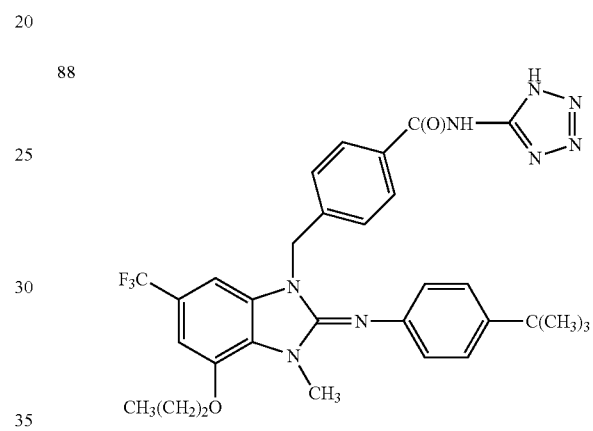
89
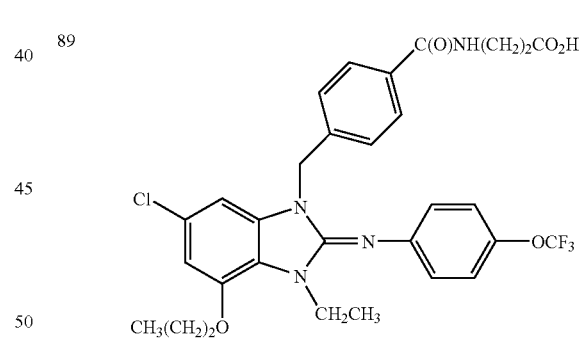
90
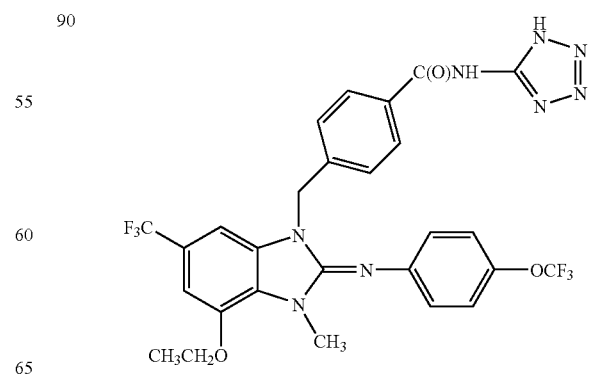

TABLE 1-continued

91 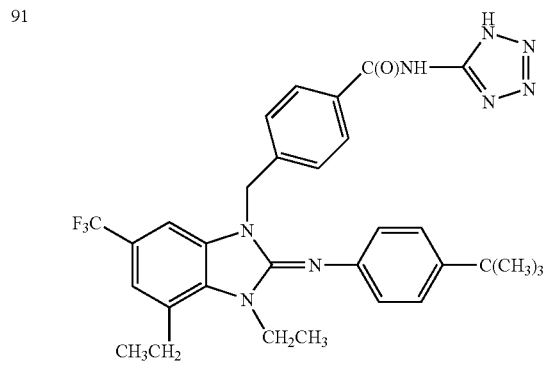

92 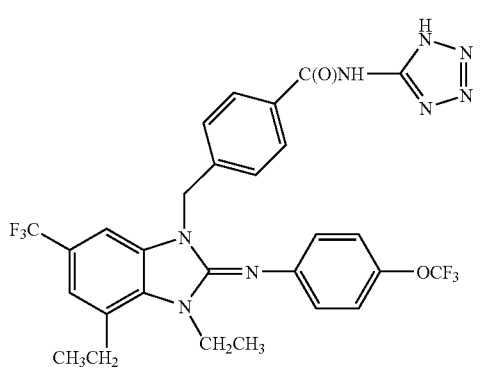

93 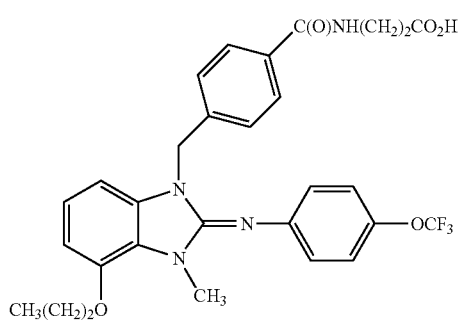

94 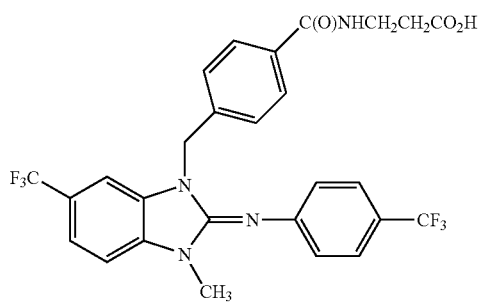

TABLE 1-continued

95 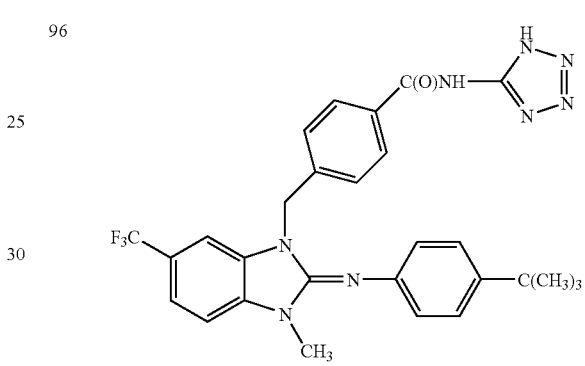

96 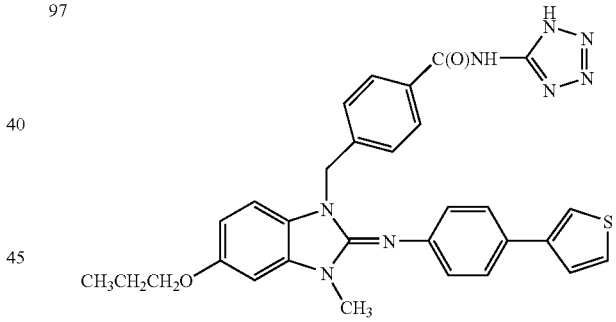

97

Pharmaceutically acceptable salts and solvates of the species noted above are also included.

The invention further includes a pharmaceutical composition which is comprised of a compound of formula I or a pharmaceutically acceptable salt or solvate thereof, in combination with a pharmaceutically acceptable carrier.

Also included is a method of treating type 2 diabetes mellitus in a mammalian patient in need of such treatment, comprising administering to said patient a compound of formula I in an amount that is effective to treat type 2 diabetes mellitus.

Also included is a method of preventing or delaying the onset of type 2 diabetes mellitus in a mammalian patient in need thereof, comprising administering to said patient a compound of formula I in an amount that is effective to prevent or delay the onset of type 2 diabetes mellitus.

Also included in the present invention is a method of treating hyperglycemia, diabetes or insulin resistance in a mammalian patient in need of such treatment which comprises administering to said patient an effective amount of a compound of formula I.

Also included in a method of treating, preventing or delaying the onset of diseases or conditions that are associated with type 2 diabetes mellitus. Examples include diseases and conditions selected from the group consisting of: dyslipidemias, (e.g., hyperlipidemia), such as elevated levels of cholesterol (hypercholesterolemia), triglycerides (hypertriglyceridemia) or low density lipoproteins (LDL) (high LDL levels), low levels of high density lipoprotein (HDL), microvascular or macrovascular changes and the sequellae of such conditions, such as coronary heart disease, stroke, peripheral vascular disease, hypertension, renal hypertension, nephropathy, neuropathy and retinopathy. The method entails administering to a type 2 diabetic patient, e.g., a human patient, an amount of a compound of formula I that is effective for treating, preventing or delaying the onset of such diseases or conditions.

Also included in the present invention is a method of treating atherosclerosis in a mammalian patient in need of such treatment, comprising administering to said patient a compound of formula I in an amount effective to treat atherosclerosis.

Also included in the present invention is a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalina patient in need of such treatment, comprising administering to the patient a compound in accordance with formula I in an amount that is effective to treat said condition.

Also included in the present invention is a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high IDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I in an amount that is effective to delay the onset of said condition.

Also included in the present invention is a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I in an amount that is effective to reduce the risk of developing said condition.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Salts and Solvates

The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I include the pharmaceutically acceptable salts and solvates.

This invention relates to method of antagonizing or inhibiting the production or activity of glucagon, thereby reducing the rate of gluconeogenesis and glycogenolysis, and the concentration of glucose in plasma.

The compounds of formula I can be used in the manufacture of a medicament for the prophylactic or therapeutic treatment of disease states in mammals caused by elevated levels of glucose, comprised of combining the compound of formula I with the carrier materials to provide the medicament.

Dose Ranges

The prophylactic or therapeutic dose of a compound of formula I will, of course, vary with the nature of the condition to be treated, the particular compound selected and its route of administration. It will also vary according to the age, weight and response of the individual patient. In general, the daily dose range lie within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount" "anti-diabetic effective amount" and the other terms appearing throughout the application addressing the amount of the compound to be used refer to the dosage ranges provided, taking into account any necessary variation outside of these ranges, as determined by the skilled physician.

Representative dosages for adults range from about 0.1 mg to about 1.0 g per day, preferably about 1 mg to about 200 mg, in single or divided doses.

When intravenous or or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of Formula I per kg of body weight per day.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred. Thus, one aspect of the invention that is of interest is the use of a compound of formula I for preparing a pharmaceutical composition which is comprised of combining the compound of formula I with the carrier.

In preparing oral compositions, any of the usual pharmaceutical media may be employed, such as, for example, water, glycols, oils, alcohols, flavoring agents, preservatives, coloring agents and the like in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets, with the solid oral preparations being preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 1 g of the active ingredient and each cachet or capsule contains from about 1 to about 500 mg of the active ingredient.

The following are examples of pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to make | 1.0 mL |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| Total | 500 mg |

| Capsule | mg/capsule |
|---|---|
| Compound of Formula I | 25 |
| Lactose Powder | 573.5 |
| Magnesium Stearate | 1.5 |
| Total | 600 mg |

| Aerosol | Per canister |
|---|---|
| Compound of Formula I | 24 mg |
| Lecithin, NF Liq. Conc. | 1.2 mg |

-continued

| | |
|---|---|
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/delaying the onset of type 2 diabetes mellitus, as well as the diseases and conditions associated with type 2 diabetes mellitus, for which compounds of Formula I are useful. Other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) bis-guanides (e.g., buformin, metformin, phenformin), (b) PPAR agonists (e.g., troglitazone, pioglitazone, rosiglitazone), (c) insulin, (d) somatostatin, (e) α-glucosidase inhibitors (e.g., voglibose, miglitol, acarbose), (f) DP-IV inhibitors, (g) IXR modulators and (h) insulin secretagogues (e.g., acetohexamide, carbutamide, chlorpropamide, glibomuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide).

The weight ratio of the compound of the Formula I to the second active ingredient may be varied within wide limits and depends upon the effective dose of each ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

Examples of pharmaceutical combination compositions include:

(1) a compound according to formula I,
(2) a compound selected from the group consisting of:
  (a) DP-IV inhibitors;
  (b) insulin sensitizers selected from the group consisting of (i) PPAR agonists and (ii) biguanides;
  (c) insulin and insulin mimetics;
  (d) sulfonylureas and other insulin secretagogues;
  (e) α-glucosidase inhibitors;
  (f) glucagon receptor antagonists;
  (g) GLP-1, GLP-1 mimetics, and GLP-1 receptor agonists;
  (h) GIP, GIP mimetics, and GIP receptor agonists;
  (i) PACAP, PACAP mimetics, and PACAP receptor 3 agonists;
  (j) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA:cholesterol acyltransferase inhibitors, (viii) anti-oxidants and (ix) LXR modulators;
  (k) PPARδ agonists;
  (l) antiobesity compounds;
  (m) an ileal bile acid transporter inhibitor;
  (n) anti-inflammatory agents other than glucocorticoids; and
  (o) protein tyrosine phosphatase-1B (PTP-1B) inhibitors; and
(3) a pharmaceutically acceptable carrier In accordance with the methods described herein one method that is of interest relates to a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient an effective amount of a compound of formula I and a compound selected from the group consisting of:
  (a) DP-IV inhibitors;
  (b) insulin sensitizers selected from the group consisting of (i) PPAR agonists and (ii) biguanides;
  (c) insulin and insulin mimetics;
  (d) sulfonylureas and other insulin secretagogues;
  (e) α-glucosidase inhibitors;
  (f) glucagon receptor antagonists;
  (g) GLP-1, GLP-1 mimetics, and GLP-1 receptor agonists;
  (h) GIP,GEP mimetics, and GIP receptor agonists;
  (i) PACAP, PACAP mimetics, and PACAP receptor 3 agonists;
  (j) cholesterol lowering agents selected from the group consisting of (i) HMG-CoA reductase inhibitors, (ii) sequestrants, (iii) nicotinyl alcohol, nicotinic acid and salts thereof, (iv) PPARα agonists, (v) PPARα/γ dual agonists, (vi) inhibitors of cholesterol absorption, (vii) acyl CoA:cholesterol acyltransferase inhibitors, (viii) anti-oxidants and (ix) LXR modulators;
  (k) PPARδ agonists;
  (l) antiobesity compounds;
  (m) an ileal bile acid transporter inhibitor
  (n) anti-inflammatory agents excluding glucocorticoids; and
  (o) protein tyrosine phosphatase-1B (PTP-1B) inhibitors, said compounds being administered to the patient in an amount that is effective to treat said condition.

More particularly, a method that is of interest relates to a method of treating a condition selected from the group consisting of-hypercholesterolemia, atherosclerosis, low HDL levels, high LDL levels, hyperlipidemia, hyperkriglyceridemia and dyslipidemia, in a mammalina patient in need of such treatment, comprising administering to the patient a therapeutically effective amount of a compound of formula I and an HMG-CoA reductase inhibitor.

Even more particularly, the method that is of interest comprises administering to the patient a therapeutically effective amount of a compound of formula I and an HMG-CoA reductase inhibitor wherein the MG-CoA reductase inhibitor is a statin, and even more particularly, the statin is selected from the group consisting of lovastatin, simvastatin, pravastatin, fluvastatin, atorvastatin, itavastatin, ZD-4522 and rivastatin.

A different aspect of the invention relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound of formula I and an HMG-CoA reductase inhibitor.

Another aspect of the invention relates to a method for delaying the onset or reducing the risk of developing atherosclerosis in a human patient in need of such treatment comprising administering to said patient an effective amount of a compound of formula I and an HMG-CoA reductase inhibitor. More particularly, the method comprises administering an effective amount of a compound of formula I and an HMG-CoA reductase inhibitor wherein the HMG-CoA reductase inhibitor is a statin. Even more particularly, the method comprises administering a compound of formula I and a statin selected from the group consisting of: lovastatin, simvastatin, pravastatin, fluvastatin, atorvastatin, itavastatin, ZD-4522 and rivastatin. Still more particularly, the method comprises administering a compound of formula I and the statin known as simvastatin.

Another aspect of the invention relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound of formula I and a cholesterol absorption inhibitor. In particular, the method comprises administering an effective amount of a compound of formula I and the cholesterol absorption inhibitor known as ezetimibe.

More particularly, a method for delaying the onset or reducing the risk of developing atherosclerosis in a human patient in need of such treatment is described which comprises administering to said patient an effective amount of a compound of formula I and a cholesterol absorption inhibitor. More particularly, the method comprises administering a compound of formula I and the cholesterol absorption inhibitor known as ezetimibe.

Throughout the instant application, the following abbreviations are used with the following meanings unless otherwise indicated:

| | |
|---|---|
| Bu = butyl, t-Bu= t-butyl | Bn and Bnzl = benzyl |
| BOC, Boc = t-butyloxycarbonyl | CBZ, Cbz = Benzyloxycarbonyl |
| DCC = Dicyclohexylcarbodiimide | DCM = dichloromethane |
| DIEA = diisopropylethylamine | DMF = N,N-dimethylformamide |
| DMAP = 4-Dimethylaminopyridine | Et = ethyl |
| EtOAc = ethyl acetate | EtOH = ethanol |
| eq. = equivalent(s) | FAB-mass spectrum = Fast atom bombardment-mass spectroscopy |
| HOAc = acetic acid | HPLC = High pressure liquid chromatography |
| HOBT, HOBt = Hydroxybenztriazole | LAH = Lithium aluminum hydride |
| Me = methyl | PBS = phosphate buffer saline |
| Ph = phenyl | TFA = Trifluoroacetic acid |
| THF = Tetrahydrofuran | TMS = Trimethylsilane |
| $C_6H_{11}$= cyclohexyl | $Nme_2$= dimethylamino |
| iPr = isopropyl | 2ClPh = 2-chlorophenyl |
| 2,4-diClPh = 2,4-dichlorophenyl | Py, Pyr = pyridyl |

Compounds of the present invention may be prepared according to the methodology outlined in the following general synthetic schemes.

In one embodiment of the present invention, the compounds (Ia) may be prepared from ester IIa (vide infra),

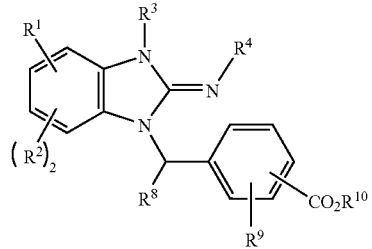

IIa where $R^1$, $R^2$, $R^3$, $R^4$, $R^8$, and $R^9$ are as defined above and $R^{10}$ represents an alkyl or aryl group.

Compounds IIa can be prepared using a variety of methods which will become apparent to those of ordinary skill from the teachings herein, one such route being illustrated in Scheme 1. Aniline 1 is treated with thiophosgene in the presence of a base such as diethylisopropylamine (DIEA) in a nonpolar aprotic solvent such as dichloromethane at temperatures of zero to 25° C. followed by direct addition of a 1,2-diaminobenzene 2 and either mercury (II) trifluoroacetate or methyl iodide (for example J. Med. Chemi., 1985, 28, 1925 and Synthesis, 1974, 41). The reaction is stirred a further 30 min to 6 h before isolation of benzimnidazole 3 with an aqueous work-up. 1,2-Diaminobenzene analogs 2 are commercially available, or readily prepared by those skilled in the art by reduction of the corresponding 2-nitroaniline with, for example hydrogen and a palladium catalyst or stannous chloride. Either reaction is effected in an alcoholic solvent such as methanol or ethanol. In some instances, the isothiocyanates prepared in situ above are commercially available and can be used directly in the reaction.

Benzimidazole 3 is converted to intermediate 4 by deprotonation with a base such as sodium hydride in a polar aprotic solvent such as dimethylformamide (DMF) at 0-25° C. for 15 min to 2 h, followed by addition of a benzyl electrophile such as 4-carbomethoxy benzyl bromide. The reaction is stirred, with heating if necessary, for an additional 1-24 h to give intermediate 4. The alkylation can alternatively be achieved in the absence of base by stirring the electrophile with benzimidazole 3 in a polar aprotic solvent such DMF or acetonitrile at elevated temperatures for 6-24 h. At this point mixtures of isomers may be obtained, compounds can be separated by recrystallization, trituration, preparative thin layer chromatography, flash chromatography on silica gel as described by W. C. Still et al, J. Org. Chem., 43, 2923, (1978), or HPLC. Compounds purified by HPLC may be isolated as the corresponding salt. Purification of intermediates is achieved in the same manner. The above reaction should be repeated on intermediate 4, using an electrophile such as methyl iodide to give the fully elaborated cyclic guanidine intermediate 5.

SCHEME 1

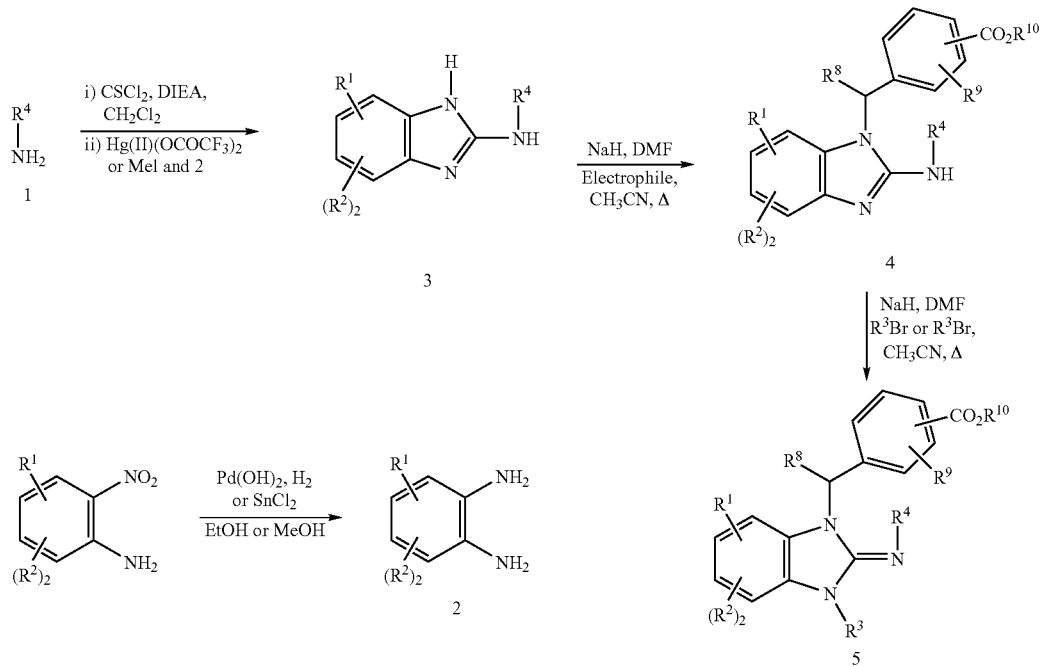

An alternate route to cyclic guanidine 5 is illustrated in Scheme 2 and 3. and goes via the N-alkylated 1,2-diaminobenzene 6. These are commercially available or readily prepared by those skilled in art. One such method involves alkylation of a 2-nitro aniline. This is effected by deprotonation with a base such as sodium hydride in a polar aprotic solvent such as dimethylformamide (DMF) at 0-25° C. for 15 min to 2 h, followed by addition of an electrophile such as an alkyl iodide, Scheme 2. The reaction is stirred for an additional 1-24 h to give intermediate 7, which can be reduced with, for example hydrogen and a palladium catalyst or stannous chloride in an alcoholic solvent. The alkylated 2-nitro aniline 7 can also be prepared by nucleophilic displacement of fluorine from a 2-fluoronitrobenzene 8 with an amine as described in *J. Org. Chem.*, 1999, 64, 3060. This is achieved in a solvent such as methylene chloride or DMF with a base such as DIEA, at temperatures of 25-80° C. for 1-6 h, Scheme 2. The diaminobenzene 6 can then be converted to the benzimidazole 9 using amine 1 in an identical fashion to that described above. Finally, reaction with an appropriate electrophile such as 4-carbomethoxy benzyl bromide gives intermediate 5, vide supra and illustrated in Scheme 3. The order of reaction with the two electrophiles may be reversed, such that intermediate 2 is first elaborated with the benzyl bromide to give, after reaction with amine 1 benzimidazole 4 which is converted to 5 as in Scheme 1.

SCHEME 2

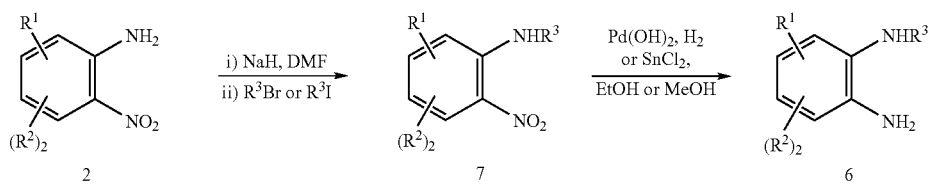

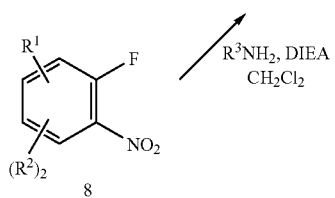

SCHEME 3 (continued)

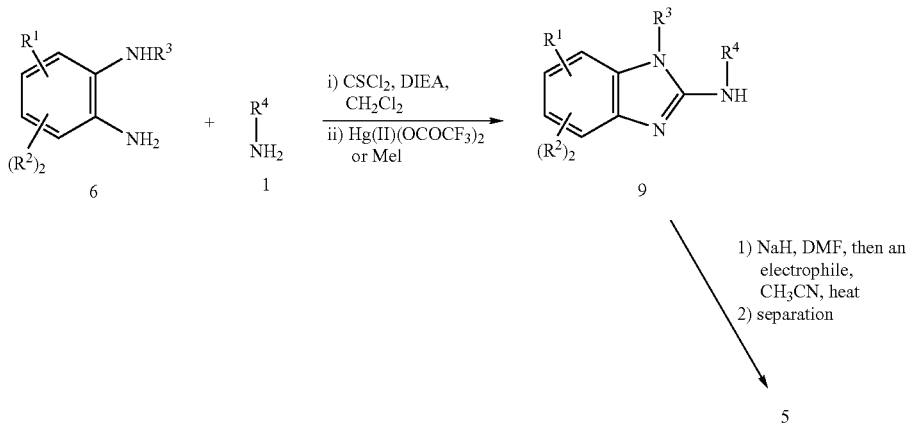

Preparation of the desired compounds Ia is then achieved by saponification of the ester 5 using a base such as aqueous lithium or sodium hydroxide in a polar solvent such as tetrahydrofuran, methanol, ethanol or a mixture of similar solvents, Scheme 4. Coupling of the acid with an amine, generally 5-aminotetrazole 10 or a beta alanine derivative 11 which may be substituted at the 2-position, is then achieved using 1-ethyl-3-(3-dimethylaminopropyl)-carbodiimide (EDC), 1-hydroxybenzotriazole (HOBt), and a base, generally diisopropylethylamine, in a solvent such as N,N-dimethylformamide (DMF) or methylene chloride for 3 to 48 hours at ambient temperature to yield the compounds Ia-10 and Ia-11. Other peptide coupling conditions may also be used. The product is purified from unwanted side products by recrystallization, trituration, preparative thin layer chromatography, flash chromatography on silica gel as described by W. C. Still et al, *J. Org. Chem.*, 43, 2923, (1978), or HPLC. Compounds purified by HPLC may be isolated as the corresponding salt. Purification of intermediates is achieved in the same manner. As will be understood by those skilled in the art, for the preparation of enantiomerically pure compounds, enantiomerically pure starting materials should be used.

SCHEME 4

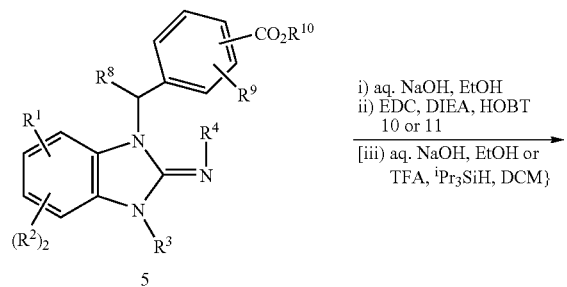

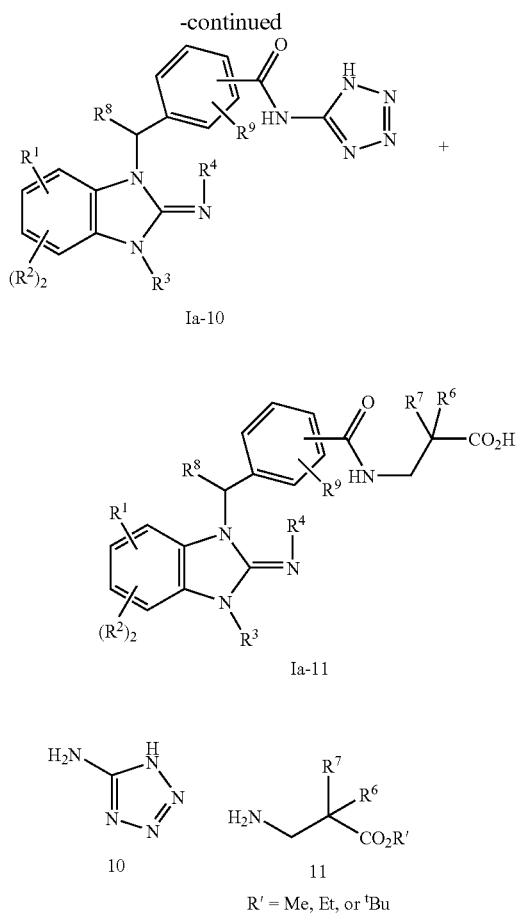

In some cases further modification of intermediates such as 5 can be undertaken in one of several different ways. These manipulations may include, but are not limited to substitution, reduction, oxidation, alkylation, acylation, and hydrolysis reactions, which are commonly known to those skilled in the art. One such modification, illustrated here when $R^4$ is a protected phenol as in 12, involves release of the alcohol and subsequent etherification. The hydroxyl group may be protected as a silyl ether, in which case a fluoride source, generally hydrofluoric acid or tetrabutylammonium fluoride is used for the reaction. Deprotection of a methoxy ether is routinely effected by treatment of the compound with boron tribromide in a solvent such as methylene chloride for a period of 1-16 h at ambient temperatures. Finally, if the alcohol is protected as an alkyl ether this is removed by treatment with dimethylbarbituric acid and a palladium catalyst, routinely tris(dibenzylideneacetone)dipalladium(0), with a ligand such as 1,4-bis-(diphenylphospino)butane in an aprotic solvent such as methylene chloride for 15 min to 2 h. See "Protective Groups in Organic Synthesis", Greene, published by Wiley and Sons.

SCHEME 5

12

13

ROH, DIAD
PPh$_3$, CH$_2$Cl$_2$

-continued

14

The free hydroxyl group may then be further modified to prepare ethers using an alcohol and coupling agent, such as diisopropylazodicarboxylate (DIAD), and triphenylphosphine in a non polar solvent such as methylene chloride at temperatures of 0 to 40° C. for 1 to 16 h, Scheme 5. Intermediates 13 and 14 can then be converted to the desired products as previously described, vide supra. Similar chemistry can be applied in the case when R$^1$ or R$^2$ are protected alcohols.

Other modifications, illustrated here when R$^1$ contains an aromatic bromide or iodide as in 15, Scheme 6, involve coupling reactions for example in a Suzuki type coupling where the halide is coupled with a boronic acid, exemplified here with phenyl boronic acid, using a palladium catalyst such as palladium acetate and tris-o-tolylphosphine or triphenyl phosphine. The solvent is generally DMF, toluene or ethanol, and cesium carbonate or aqueous sodium carbonate is also added to the reaction, which is performed at elevated temperatures for 12-24 h (see *Helv. Chim. Acta*, 1992, 75, 855). Alternatively bromide 15 can be coupled with an alkenyl stannane 17 (in which R$^1$=alkyl) or alkyl zinc reagent 18 using a palladium catalyst such as triphenyl phosphine in a polar solvent such as THF or DMF at elevated temperatures (see *J. Org. Chem.*, 1998, 63, 3764). Coupling with an alcohol to provide ethers 21 is again achieved with a palladium catalyst, most usually palladium acetate and a phosphine ligand in the presence of a base such as cesium carbonate in a non polar aprotic solvent such as toluene at elevated temperatures (see *J. Am. Chem. Soc.*, 2001, 123, 10770).

SCHEME 6

16

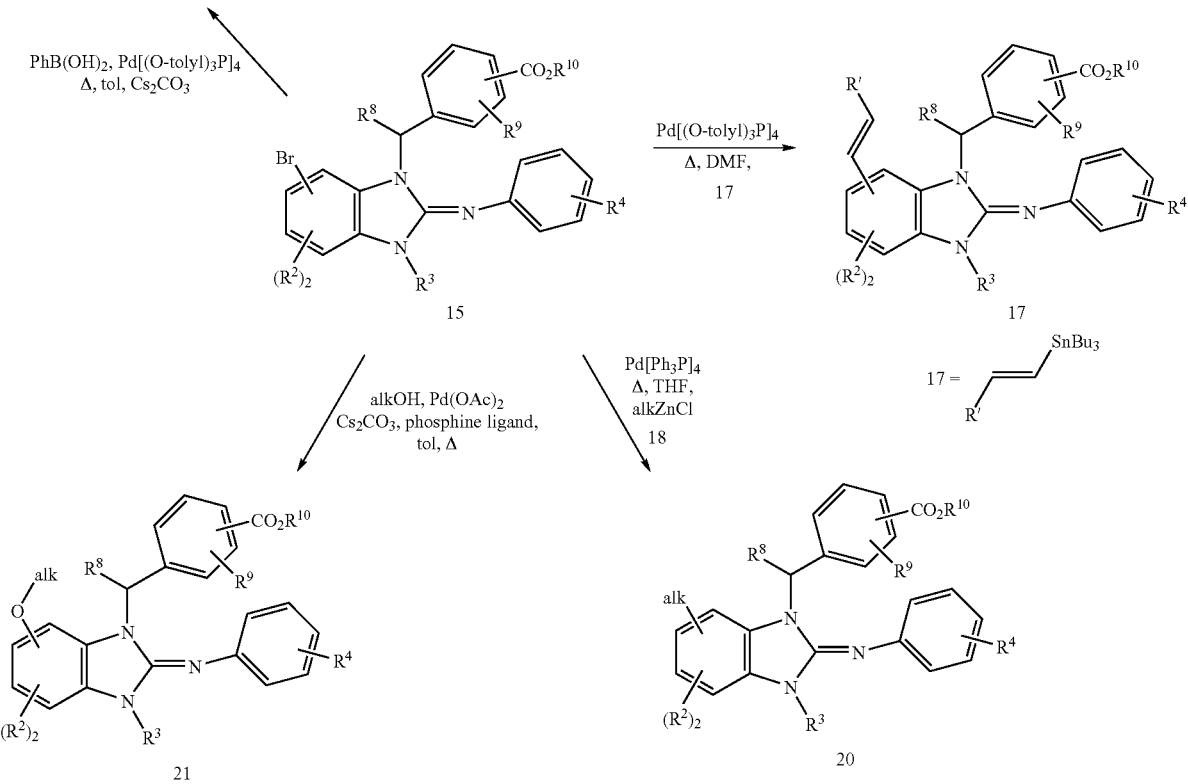

Similar chemistry can be applied in the case when $R^2$ or $R^4$ are aromatic bromides or iodides. Intermediates 16 and 19-21 can then be converted to the desired products as previously described, vide supra.

LC-MS Conditions:

Method A: column: Waters Xterra C18 (3.0×50 mm). Gradient: 10-98% MeCN (containing 0.05% TFA)/H$_2$O (containing 0.06% TFA) over 3.75 min @ 1 mL/min Method B: column: MetaChem Polaris (4.6×50 mm). Gradient: 5-95% MeCN/H$_2$O, (both with 0.05% TFA) over 2.5 min @ 2.5 mL/min Method C: column: Waters Xterra C18 (3.0×50 mm). Gradient: 10-100% MeCN (containing 0.05% formic acid)/ H$_2$O (containing 0.06% formic acid) over 3.75 min @ 1 mL/min Preparative HPLC was performed on a YMC-Pack Pro C18 column (150×20 mm i.d.) at an initial flow rate of 4 mL/min for 1.35 min, followed by 20 mL/min for 10.6 min. The gradients employed during the faster part of the run are described, and all runs were followed with 100% organic at 20 mL/min for 0.5 min.

The following examples are provided so that the invention might be more fully understood. They should not be construed as limiting the invention in any way.

EXAMPLE 1

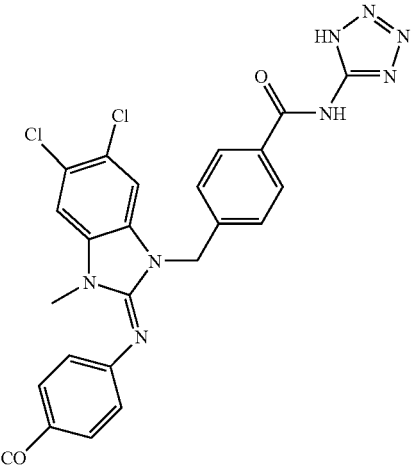

Method 1

Step A. 4,5-dichloro-N-methyl-2-nitroaniline

To a solution of 4,5-dichloro-2-nitroaniline (10 mmol, 2.07 g) in DMF (10 mL) was added NaH (12 mmol, 480 mg of 60% suspension in mineral oil) (exothermic, gas evolution). After 15 min MeI (20 mmol, 1.2 mL) was added. The reaction mixture was allowed to stand at ambient temperature for 1 h, then poured into a solution of saturated NaHCO$_3$ and brine, affording the product as an orange precipitate, which was filtered, washed with water and dried in vacuo. $^1$H NMR (500 MHz, d$_6$-DMSO) δ 8.27 (m, 1H), 8.22 (s, 1H), 7.25 (s, 1H), 2.96 (d, J=4.9 Hz, 3H).

Step B. 4,5-Dichloro-N-methylbenzene-1,2-diamine

The title compound of Example 1, Method 1, Step A (5 mmol, 1.1 g) and $SnCl_2 \cdot 2H_2O$ (15 mmol, 3.4 g) were stirred in 40 mL of DMF at 40° C. for 16 hr. The reaction mixture was diluted with $CH_2Cl_2$, poured into saturated $NaHCO_3$ and stirred for 1 h. The resulting slurry was filtered over celite, and the filter cake was washed with $CH_2Cl_2$. The organic phase was collected, dried with $Na_2SO_4$ and concentrated in vacuo to afford a brown oil. Flash chromatography on silica eluting with 20% EtOAc in hexanes provided the product as a purple solid. LC-MS (ESI, Method B): 1.58 min, m/z 191.1 (M+1).

Step C. 5,6-Dichloro-1-methyl-N-[4-(trifluoromethoxy)phenyl]-1H-benzimidazol-2-amine A solution of the title compound in Example 1, Method 1, Step B (0.6 mmol, 114 mg) and 4-trifluoromethoxyphenyl isothiocyanate (0.6 mmol, 97 µL) was heated in $CH_2Cl_2$ (1 mL) at 40° C. for 1 h, then allowed to stand at ambient temperature for 16 h. DIEA (1.2 mmol, 209 µL) and MeI (0.9 mmol, 75 µL) were added to the reaction, and the resultant mixture was heated at 40° C. for 5 h, then purified directly by flash chromatography on silica eluting with a step gradient of 20-25% EtOAc in hexanes. LC-MS (ESI, Method B): 1.94 min, m/z 376.1 (M+1).

Step D. Methyl 4-[(5,6-dichloro-3-methyl-2-{[4-(trifluoromethoxy)phenyl]imino}-2,3-dihydro-1H-benzimidazol-1-yl)methyl]-N-1H-tetrazol-5-ylbenzoate To the title compound of Example 1, Method 1, Step C (0.38 mmol, 144 mg) in DMF (1.2 mL) was added NaH (0.46 mmol, 18 mg of a 60% suspension in mineral oil). After 10 min methyl-4-(bromomethyl)benzoate (0.46 mmol, 105 mg) was added and the reaction mixture was left at ambient temperature for 16 h. The reaction mixture was partitioned between $CH_2Cl_2$ and $NaHCO_3$. The organic phase was dried with $Na_2SO_4$ and concentrated in vacuo. Flash chromatography on silica eluting with 20% EtOAc in hexanes afforded the product. $^1$H NMR (500 MHz, $d_6$-DMSO) δ 7.89 (d, J=8 Hz, 2H), 7.45 (s, 1H), 7.37 (s, 1H), 7.29 (d, J=8 Hz, 2H), 7.12 (d, J=8 Hz, 2H), 6.86 (m, 2H), 5.13 (s, 2H), 3.84 (s, 3H), 3.14 (s, 3H). LC-MS (ESI, Method B): 2.10 min, m/z 524.0 (M+1).

Step E. 4-[(5,6-Dichloro-3-methyl-2-{[4-(trifluoromethoxy)phenyl]imino}-2,3-dihydro-1H-benzimidazol-1-yl)methyl]-N-1H-tetrazol-5-ylbenzamide To the title compound of Example 1, Method 1, Step D (0.17 mmol, 87 mg) in dioxane (1.6 mL) was added a solution of LiOH (0.8 mmol, 20 mg) in $H_2O$ (0.8 mL). The reaction was stirred at 45° C. for 2 h. The product was partitioned between EtOAc and pH 7 phosphate buffer. The organic phase was dried with $MgSO_4$ and concentrated under reduced pressure to provide a yellow foamy solid. To a portion of the solid (0.12 mmol, 61 mg) was added a solution of 1H-tetraazol-5-amine monohydrate (0.36 mmol, 37 mg), HOBt (0.24 mmol, 37 mg), EDC (0.24 mmol, 46 mg) and DIEA (0.36 mmol, 63 µL) in DMF (1 mL). The reaction mixture was allowed to stand at ambient temperature for 16 h, then concentrated under reduced pressure. The residue was taken up in 2:1 dioxane/$H_2O$, acidified with TFA, and purified by reverse-phase chromatography (20-60% MeCN in $H_2O$, both containing 0.1% TFA). Lyophilization afforded the title compound as a white solid. $^1$H NMR (500 MHz, $d_6$-DMSO+$Et_3$N): δ 7.90 (d, J=8 Hz, 1H), 7.44 (s, 1H), 7.39 (s, 1H), 7.25 (d, J=8 Hz), 2H), 7.15 (d, J=8 Hz, 2H), 6.89 (m, 2H), 5.11 (s, 2H), 3.15 (s, 3H). LC-MS (ESI, Method A): 2.86 min, m/z 577.2 (M+1).

Method 2.

Step A. 5,6-Dichloro-N-[4-(trifluoromethoxy)phenyl]-1H-benzimidazol-2-amine

A solution of 4,5-dichloro-1,2-phenylenediamine (2 mmol, 354 mg) and 4-trifluoromethoxyphenyl isothiocyanate (2 mmol, 325 µL) in $CH_2Cl_2$ (3 mL) was heated at 40° C. for 4 h. MeI (2.2 mmol, 137 µL) and DIEA (2.0 mmol, 348 µL) were added, and the reaction was brought to 40° C. for 24 h. The reaction mixture was partitioned between $CH_2Cl_2$ and brine. The organic phase was dried with $Na_2SO_4$ and concentrated in vacuo. Chromatography on silica eluting with 20-40% EtOAc in hexanes provided the product as a tan solid. $^1$H NMR (500 MHz, $d_6$-DMSO) δ 11.2 (br s, 1H), 9.91 (s, 1H), 7.84 (m, 2H), 7.52 (br s, 1H), 7.34 (d, J=9 Hz, 2H). LC-MS (ESI, Method A): 2.96 min, m/z 362.1 (M+1).

Step B. Methyl 4-[(5,6-dichloro-2-{[4-(trifluoromethoxy)phenyl]imino}-1H-benzimid-azol-1-yl)methyl]benzoate To the title compound of Example 1, Method 2, Step A (0.36 mmol, 130 mg) in DMF (2.5 mL) was added NaH (0.43 mmol, 17 mg of 60% suspension in mineral oil). After 10 min methyl-4-(bromomethyl)benzoate (0.36 mmol, 82 mg) was added and the reaction mixture was left a ambient temperature for 1 h. Aqueous workup with $CH_2Cl_2$ and brine, followed by flash chromatography on silica eluting with 20% and 30% EtOAc in hexanes provided the product. $^1$H NMR (500 Mz, $d_6$-DMSO) δ 9.59 (br s, 1H), 7.96 (d, J=9 Hz, 2H), 7.93 (d, J=8 Hz, 2H), 7.66 (s, 1H), 7.56 (s, 1H), 7.35 (d, J=9 Hz, 2H), 7.27 (d, J=8 Hz, 2H), 5.70 (s, 2H), 3.83 (s, 3H). LC-MS (ESI, Method B): 2.30 min, m/z 510.1 (M+1).

Step C. Methyl-4-[(5,6-Dichloro-3-methyl-2-{[4-(trifluoromethoxy)phenyl]imino}-2,3-dihydro-1H-benzimidazol-1-yl)methyl]-N-1H-tetrazol-5-ylbenzoate To a solution of the title compound of Example 1, Method 2, Step B (0.27 mmol, 138 mg) in DMF (1.5 mL) was added NaH (0.32 mmol, 13 mg of 60% suspension in mineral oil). After 5 min MeI (0.54 mmol, 34 µL) was added. After 2 h the reaction mixture was partitioned between $CH_2Cl_2$ and saturated $NaHCO_3$. The organic phase was dried with $MgSO_4$ and concentrated in vacuo to afford the desired product [LC-MS (ESI, Method B): 2.13 min, m/z 524.1 (M+1)] and 2-N-methylbenzimidazole regioisomer [LC-MS (ESI, Method B): 2.32 min, m/z 524.1 (M+1)] in a ca. 2:1 ratio, which was taken on directly.

Step D. 4-[(5,6-Dichloro-3-methyl-2-{[4-(trifluoromethoxy)phenyl]imino}-2,3-dihydro-1H-benzimidazol-1-yl)methyl]-N-1H-tetrazol-5-ylbenzamide The product of Example 1, Method 2, Step C was dissolved in 1.6 mL of dioxane and a solution of LiOH (1.1 mmol, 26 mg) in 0.8 mL of H₂O was added. The reaction was stirred at 45° C. for 2 h, then partitioned between EtOAc and pH 7 phosphate buffer. The organic phase was dried with MgSO₄ and concentrated under reduced pressure to afford the product as an orange foam. To a portion of the solid containing the two N-methyl regioisomers (0.18 mmol, 93 mg) was added a solution of 1H-tetraazol-5-amine monohydrate (0.5 mmol, 48 mg), HOBt (0.3 mmol, 47 mg), EDC (0.3 mmol, 59 mg) and DIEA (0.5 mmol, 82 µL) in DMF (1.5 mL). The reaction mixture was brought to 40° C. for 1 h, then concentrated under reduced pressure. The residue was taken up in ca. 2:1 dioxane/H₂O, acidified with TFA, and purified by reverse-phase chromatography (20-60% MeCN/H₂O, both containing 0.1% TFA). Lyophilization afforded the title compound as a white solid. Spectroscopic data were identical with that obtained above.

EXAMPLE 2

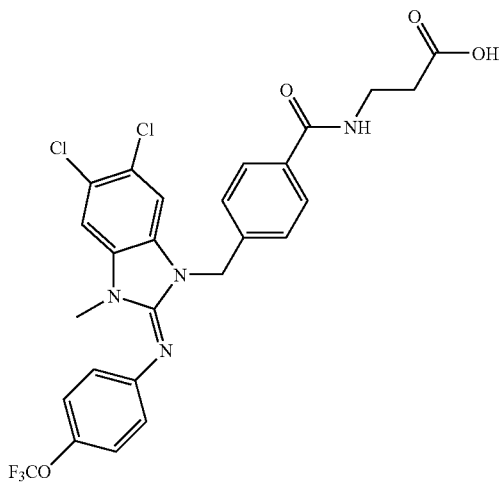

N-{4-[(5,6-Dichloro-3-methyl-2-{[4-(trifluoromethoxy)phenyl]imino}-2,3-dihydro-1H-benzimidazol-1-yl)methyl]benzoyl}-β-alanine To the title compound of Example 1, Method 1, Step E (0.04 mmol, 20 mg) was added a solution of the hydrochloride salt of β-alanine tert-butyl ester (0.08 mmol, 15 mg), HOBt (0.0.08 mmol, 12 mg), EDC (0.08 mmol, 15 mg) and DIEA (0.12 mmol, 21 µL) in DMF (0.5 mL). The reaction mixture was allowed to stand at ambient temperature for 16 h, and then partitioned between EtOAc/H₂O. The organic phase was dried with MgSO₄ and the solvent was removed under reduced pressure. To the residue was added 1.2 mL of 2:30:68 H₂O/TFA/CH₂Cl₂. The resultant solution was stirred for 1 h and concentrated under reduced pressure. Reverse-phase chromatography (20-60% MeCN/H₂O, both containing 0.1% TFA), followed by lyophilization, afforded the product as a white solid. ¹H NMR (500 MHz, d₆-DMSO) δ 8.54 (t, J=5 Hz, 1H), 8.09 (s, 1H), 7.89 (s, 1H), 7.77 (d, J=8 Hz, 2H), 7.34 (d, J=9 Hz, 2H), 726 (d, J=9 Hz, 2H), 7.24 (d, J=8 Hz, 2H), 5.43 s, 2H), 3.42-3.47 (overlapping s, m, 5H), 2.50 (t, J=7 Hz, 2H). LC-MS (ESI, Method A): 2.78 min m/z 581.1 (M+1).

EXAMPLE 3

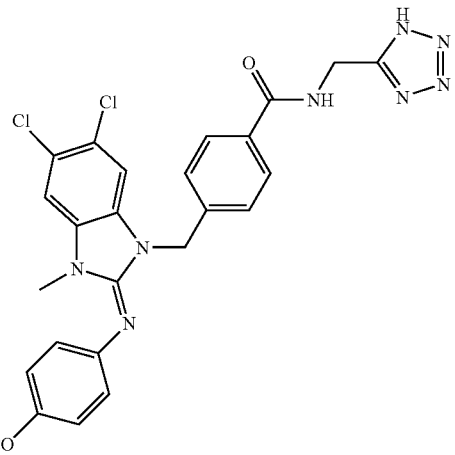

4-[(5,6-Dichloro-3-methyl-2-{[4-(trifluoromethoxy)phenyl]imino}-2,3-dihydro-1H-benzimidazol-1-yl)methyl]-N-(1H-tetrazol-5-ylmethyl)benzamide To the title compound of Example 1, Method 2, Step C (0.03 mmol, 15 mg) was added a solution of the hydrochloride salt of 2-aminomethyltetrazole (0.06 mmol, 8 mg), HOBt (0.06 mmol, 9 mg), EDC (0.06 mmol, 12 mg) and DIEA (0.09 mmol, 16 µL) in DMF (0.7 mL). The reaction mixture was brought to 40° C. for 2 h, then allowed to stand at ambient temperature for 16 h, and concentrated in vacuo. Purification by reverse-phase chromatography (20-60% MeCN/H₂O, both containing 0.1% TFA), followed by lyophilization, afforded the product as a white solid. ¹H NMR (500 MHz, d₆-DMSO) δ 9.23 (t, 5.6 Hz, 1H), 7.83 (d, J=8.5 Hz, 2H), 7.58-7.80 (overlapping br s, 2H), 7.22-7.34 (overlapping m, 4H), 7.04-7.20 (unres. m, 2H), 5.32 (br s, 2H), 4.75 (d, J=5.8 Hz, 2H). LC-MS (ESI, Method A): 3.02 min, m/z 591.1 (M+1).

EXAMPLE 4

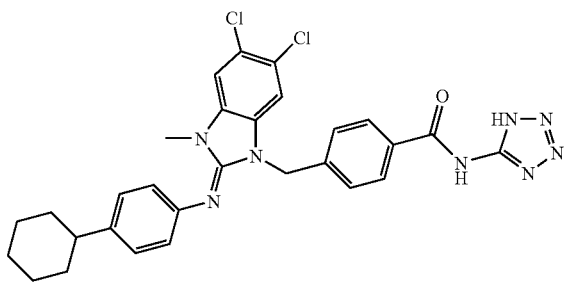

Step A. 5,6-Dichloro-N-[4-(cyclohexyl)phenyl]-1H-benzimidazol-2-amine

To a stirring solution of 4-cyclohexylaniline (10 mmol, 1.75 g) and DIEA (21 mmol, 3.65 mL) in CH₂Cl₂ (10 mL) at 0° C. was added thiophosgene (10 mmol, 700 µL)

dropwise. The solution was allowed to reach ambient temperature for 1 h, and 4,5-dichloro-1,2-phenylenediamine (10.5 mmol, 1.86 g) was added. The reaction mixture was heated to reflux for 2 h, then concentrated in vacuo. The residue was taken up in a solution of EtOH (5 mL) and MeI (20 mmol, 1.25 muL), heated at 40° C. for 16 h, and concentrated in vacuo. Flash chromatography on silica eluting with 18-25% EtOAc in hexanes afforded the product as a red solid. LC-MS (ESI, Method C): 3.47 min, m/z 360.2 (M+1).

Step B. Methyl 4-[(5,6-dichloro-2-{[4-(cyclohexyl)phenyl]amino}-1H-benzimidazol-1-yl)methyl]benzoate To the title compound of Example 4, Step A (1.1 mmol, 400 mg) in DMF (2 mL) was added NaH (1.2 mmol, 49 mg of 60% suspension in mineral oil). After 25 min methyl-4-(bromomethyl)benzoate (1.2 mmol, 280 mg) was added and the reaction mixture was allowed to stand at ambient temperature for 30 min. The reaction was diluted with saturated NH$_4$Cl (5 mL), and the crude product was extracted into EtOAc. The organic phase was dried with Na$_2$SO$_4$ and concentrated in vacuo. Flash chromatography on silica eluting with 15% EtOAc in hexanes afforded the product as a yellow solid. LC-MS (ESI, Method C): 4.44 min, m/z 508.1 (M+1).

Step C. Methyl 4-[(5,6-dichloro-3-methyl-2-{[4-(cyclohexyl)phenyl]imino}-2,3-dihydro-1H-benzimidazol-1-yl)methyl]-N-1H-tetrazol-5-ylbenzoate To a solution of the title compound of Example 4, Step B (0.38 mmol, 190 mg) in DMF (2 mL) was added NaH (0.56 mmol, 23 mg of 60% suspension in mineral oil). The reaction mixture was stirred for 20 min, and MeI (0.56 mmol, 35 μL) was added. After 1 h the reaction was quenched with saturated NH$_4$Cl and the crude product was extracted into EtOAc. The organic phase was dried with Na$_2$SO$_4$ and concentrated in vacuo. Flash chromatography on silica eluting with 10-15% EtOAc in hexanes afforded the product as a beige foam. LC-MS (ESI, Method C): 4.64 min, m/z 522.2 (M+1).

Step D. 4-[(5,6-Dichloro-3-methyl-2-{[4-(cyclohexyl)phenyl]imino}-2,3-dihydro-1H-benzimidazol-1-yl)methyl]-N-1H-tetrazol-5-ylbenzamide To the title compound of Example 4, Step C (0.15 mmol, 79 mg) in dioxane (1.8 mL), was added a solution of LiOH (1.5 mmol, 36 mg) in H$_2$O (1 mL). The resulting solution was stirred at ambient temperature for 16 h. The reaction mixture was concentrated in vacuo to remove dioxane, and then diluted with H$_2$O (3 mL) and neutralized with 2 N HCl. The resulting precipitate was filtered, washed with water and dried in vacuo to afford a white solid. A portion of the solid (0.07 mmol, 35 mg) was taken up in a solution of 1H-tetraazol-5-amine monohydrate (0.34 mmol, 35 mg), EDC (0.31 mmol, 60 mg), HOBt (0.17 mmol, 26 mg) and DIEA (0.35 mmol, 60 μL) in DMF (1 mL), and heated for 1 hr at 40° C. Purification by reverse-phase chromatography eluting with a gradient of 20-60% MeCN/H$_2$O, both containing 0.1% TFA, followed by lyophilization afforded the product as a white solid. $^1$H NMR (500 MHz, CD$_3$OD), δ (ppm): 8.02 (d, J=8.5 Hz, 2H), 8.00 (s, 1H), 7.80 (s, 1H), 7.26 (d, J=6.1 Hz, 2H), 7.24 (d, J=6.4 Hz, 2H), 7.16 (d, J=8.7 Hz, 2H), 5.46 (s, 2H), 3.66 (s, 3H), 2.55 (m, 1H), 1.86 (m, 4H), 1.76 (m, 1H), 1.44 (m, 4H), 1.30 (m, 1H). LC-MS (ESI, Method C): 2.90 min, m/z 575.2 (M+1).

EXAMPLE 5

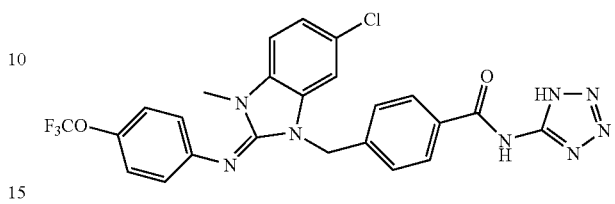

Step A. 4-chloro-N-methyl-2-nitroaniline

To a solution of 4-chloro-2-nitroaniline (10 mmol, 1.73 g) in DMF (10 mL) was added portionwise NaH (12 mmol, 480 mg of a 60% suspension in mineral oil) (exothermic, gas evolution). After 10 min MeI (20 mmol, 1.2 mL) was added to the reaction mixture. After 1 h the reaction mixture was poured into aqueous NaHCO$_3$ and brine to afford the product as an orange precipitate, which was filtered, washed with water and dried in vacuo. H$^1$ NMR (500 MHz, d$_6$-DMSO): δ 8.22 (m, 1H), 8.02 (d, J=2.5 Hz, 1H), 7.56 (dd, J=9.1 Hz, 2.5 Hz, 1H), 7.02 (d, J=9.4 Hz, 1H), 2.94 (d, J=5.0 Hz, 3H).

Step B. 4-Chloro-1-N-methylbenzene-1,2-diamine

To the title compound in Example 5, Step A (5 mmol, 933 mg) in DMF (10 mL) was added SnCl2.2H$_2$O (15 mmol, 3.38 g). The reaction mixture was stirred at 40° C. for 16 h, then poured into EtOAc and saturated NaHCO$_3$, which resulted in formation of a yellow precipitate. The slurry was filtered through celite, the filter cake was washed with water and EtOAc, and the combined organic phase was dried with Na$_2$SO$_4$ and concentrated in vacuo to provide an orange oil. Purification by flash chromatography on silica eluting with 25% EtOAc in hexanes afforded the product as an amber solid. H$^1$ NMR (500 MHz, d$_6$-DMSO): δ 6.53 (d, J=2.6 Hz, 1H), 6.48 (dd, J=8.5 Hz, 2.5 Hz, 1H), 6.30 (d, J=8.5 Hz, 1H), 4.74 (br s, 3H), 2.67 (s, 3H). LC-MS (ESI, Method B): 1.16 min, m/z 157.1 (M+1).

Step C. 5-Chloro-1-methyl-N-[4-(trifluoromethoxy)phenyl]-1H-benzimidazol-2-amine To a solution of the title compound in Example 5, Step B (0.3 mmol, 47 mg) in CH$_2$Cl$_2$ (0.5 mL) was added 4-trifluoromethoxyphenyl isothiocyanate (0.3 mmol, 49 μL). After 1 h MeI (0.5 mmol, 53 μL) was added. The reaction mixture was heated at 40° C. for 1 h, then allowed to stand at ambient temperature for 16 h. The reaction mixture was partitioned between CH$_2$Cl$_2$ and saturated NaHCO$_3$. The organic phase was dried with Na$_2$SO$_4$ and concentrated in vacuo to afford a white solid. The product was isolated by flash chromatography on silica eluting with 25% EtOAc in hexanes. LC-MS (ESI, Method B): 1.67 min, m/z 342.1 (M+1).

Step D. Methyl 4-[(6-chloro-3-methyl-2-{[4-(trifluoromethoxy)phenyl]imino}-2,3-dihydro-1H-benzimidazol-1-yl)methyl]benzoate To the title compound of Example 5, Step C (0.13 mmol, 44 mg) in DMF (0.4 mL) was added NaH (0.15 mmol, 6 mg of 60% suspension in mineral oil). After 10 min methyl-4-(bromomethyl)benzoate (0.17 mmol, 39 mg) was added and the reaction mixture was allowed to stand at ambient temperature for 1 h. Aqueous workup with $CH_2Cl_2$/saturated $NaHCO_3$, followed by flash chromatography on silica eluting with 12% EtOAc in hexanes provided the product [LC-MS (ESI, Method C) 2.94 min, m/z 490.0 (M+1)], and the 2-N-benzyl regioisomer [LC-MS (ESI, Method C) 4.16 min, m/z 490.1 (M+1)], in a ca. 1:2 ratio.

Step E. 4-[(6-Chloro-3-methyl-2-{[4-(trifluoromethoxy)phenyl]imino}-2,3-dihydro-1H-benzimidazol-1-yl)methyl]-N-1H-tetrazol-5-ylbenzamide To the product of Example 5, Step D (0.11 mmol, 52 mg) in dioxane (1 mL), was added a solution of LiOH (1 mmol, 24 mg) in $H_2O$ (0.5 mL). The resulting solution was stirred at 40° C. for 1 h, and partitioned into EtOAc/brine buffered to pH 7. The organic phase was dried with $Na_2SO_4$ and concentrated in vacuo. To the residue was added a solution of 1H-tetraazol-5-amine monohydrate (0.2 mmol, 21 mg), EDC (0.2 mmol, 38 mg), HOBt (0.2 mmol, 31 mg) and DIEA (0.3 mmol, 52 μL) in DMF (1 mL). The reaction mixture was heated for 2 h at 40° C., Reverse-phase chromatography (20-60% MeCN/$H_2O$, both containing 0.1% TFA), followed by lyophilization, afforded the product as a white solid. $^1$H NMR (500 MHz, $d_6$-DMSO+$NH_3$): δ 7.97 (d, J=7.4 Hz, 2H), 7.33 (d, J=8.0 Hz), 7.19 (d, J=2.1 Hz, 1H), 7.08-7.15 (overlapping m, 3H), 7.05 (dd, J=8.5 Hz, 2.0 Hz, 1H), 6.88 (m, 2H), 6.53 (s, 1H), 5.14 (s, 2H), 3.13 (s, 3H). LC-MS (ESI, Method C) 2.48 min, m/z 543.1 (M+1).

EXAMPLE 6

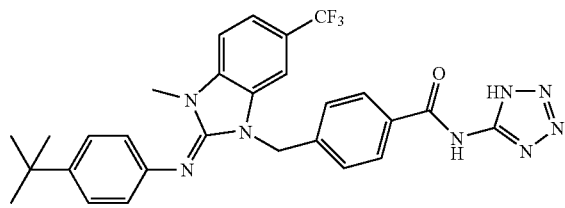

Step A. N-Methyl-2-nitro-4-(trifluoromethyl)aniline

To a solution of 2-nitro-4-trifluoromethylaniline (200 mmol, 41.2 g) in DMF (200 mL) cooled to 0° C. was added portionwise NaH (210 mmol, 8.4 g of a 60% suspension in mineral oil) (exothermic, gas evolution). The reaction was allowed to reach ambient temperature for 45 min, then cooled back to 0° C. MeI (220 mmol, 13.7 mL) was added via syringe (exothermic) and the resulting slurry was stirred for 2 h. The reaction mixture was poured into a 1:1 mixture of saturated $NaHCO_3$ and brine (1 L) to provide the product as a bright orange precipitate, which was filtered, washed with water and dried in vacuo. $^1$H NMR (500 MHz, $CDCl_3$), δ (ppm): 8.52 (d, J=1.2 Hz, 1H), 8.31 (br s, 1H), 7.70 (d, J=8.9 Hz, 1H), 6.98 (d, J=9.2 Hz, 1H), 3.13 (d, J=5.3 Hz, 3H). LC-MS (ESI, Method C): 3.34 min, m/z 221.1 (M+1).

Step B. $N^1$-methyl-4-(trifluoromethyl)benzene-1,2-diamine

The title compound of Example 6, Step A (150 mmol, 33 g) and Pearlman's catalyst (ca. 400 mg) were agitated in MeOH (200 mL) under $H_2$ (40 psi, Parr shaker) for 4 h. The reaction mixture was filtered through celite and the filtrate was concentrated in vacuo. Flash chromatography on silica eluting with 20-25% EtOAc in hexanes afforded the product as a light orange solid. $^1$H NMR (500 MHz, $CDCl_3$), δ (ppm): 7.17 (1H, d, J=8.3 Hz), 6.97 (1H, d, J=1.9 Hz), 6.68 (1H, d, J=8.2 Hz), 3.78 (1H, bs), 3.38 (2H, bs), 2.94 (3H, s). LC-MS (ESI, Method C): 2.71, m/z 191.1 (M+1).

Step C. N-(4-tert-butylphenyl)-1-methyl-5-(trifluoromethyl)-1H-benzimidazol-2-amine To a stirring solution of 4-t-butylaniline (1.3 mmol, 189 mg) and DIEA (2.53 mmol, 441 μL) in DCM (3 mL) at 0° C. was added dropwise thiophosgene (1.3 mmol, 91 μL). After 10 min the title compound of Example 6, Step B (10.5 mmol, 1.86 g) was added, and the reaction mixture was brought to 40° C. for 2 h. $Hg(O_2CCF_3)_2$ (2.5 mmol, 1 g) and DIEA (1.3 mmol, 220 μL) were added and the reaction was heated at 40° C. for 16 h. The reaction was poured into DCM and brine containing $Na_2S$, and the resulting slurry was filtered through celite. The organic phase was collected and dried over $MgSO_4$ and concentrated in vacuo. Flash chromatography on silica eluting with 25% EtOAc in hexanes afforded the product as a yellow solid. LC-MS (ESI, Method B): 1.81 min, m/z 348.3 (M+1).

Step D. 4-[(2-{[4-(tert-butyl)phenyl]imino}-3-methyl-6-trifluoromethyl-2,3-dihydro-1H-benzimidazol-1-yl)methyl]-N-1H-tetrazol-5-ylbenzamide To the title compound of Example 6, Step C (0.2 mmol, 70 mg) in DMF (1.5 mL) was added NaH (0.4 mmol, 16 mg of 60% suspension in mineral oil). After 20 min methyl-4-(bromomethyl)benzoate (0.22 mmol, 51 mg) was added. The reaction mixture was allowed to stand at ambient temperature for 30 min, then concentrated in vacuo. The residue was taken up in dioxane (2 mL), and a solution of LiOH (2 mmol, 48 mg) in $H_2O$ (1 mL) was added. The reaction mixture was stirred at 40° C. for 1 h, diluted with $H_2O$, and neutralized with 2 N HCl. The crude product was extracted with EtOAc, which was dried with $MgSO_4$ and concentrated in vacuo to afford a brown solid. The solid was taken up in a solution of 1H-tetraazol-5-amine monohydrate (1 mmol, 103 mg), EDC (0.8 mmol, 155 mg), HOBt (0.6 mmol, 92 mg) and DIEA (1 mmol, 175 μL) in DMF (1.5 mL) and heated for 3 h at 40° C. Reverse-phase chromatography (20-60% MeCN in $H_2O$, both containing 0.1% TFA) and lyophilization afforded the product as a white solid. $^1$H NMR (500 MHz, $CD_3OD$), δ (ppm): 8.02 (d, J=8.4 Hz, 2H), 7.91-7.89 (m, 2H), 7.86 (d, J=8.7 Hz, 1H), 7.44 (d, J=8.7 Hz, 2H), 7.26 (d, J=8.5 Hz, 2H), 7.21 (d, J=8.7 Hz, 2H), 5.56 (s, 2H), 3.74 (s, 3H), 1.34 (s, 9H). LC-MS (ESI, Method B): 2.04 min, m/z 549.4 (M+1).

EXAMPLE 7

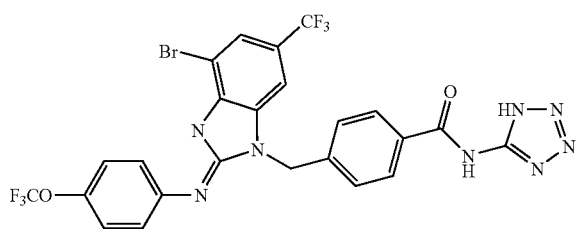

Step A. 2-Bromo-N-methyl-6-nitro-4-(trifluoromethyl)aniline

To a solution of 4-amino-3-bromo-5-nitrobenzotrifluoride (5.25 g, 18.4 mmol) in DMF (40 mL) was added NaH (883 mg, 60% suspension in mineral oil, 22.1 mmol). After 30 min MeI (1.38 mL, 22.1 mmol) was added. The reaction mixture was allowed to stand at room temperature for 1 h, then was poured into a solution of saturated aqueous NaHCO$_3$ and brine. The resulting suspension was extracted twice with CH$_2$Cl$_2$, and the combined extracts were dried over Na$_2$SO$_4$ and concentrated in vacuo. Purification by flash chromatography (5% EtOAc in hexanes, then 8% EtOAc in hexanes) provided the title compound as a yellow solid: $^1$H NMR (500 MHz, CDCl$_3$) δ 8.12 (br s, 1H), 7.86 (d, J=2.0 Hz, 1H), 6.47 (br s, 1H), 3.07 (d, J=5.5 Hz, 3H).

Step B. 2-Bromo-N$^1$-methyl-4-(trifluoromethyl)benzene-1,2-diamine

To a solution of the title compound in Example 7, Step A (5.78 g, 19.3 mmol) in DMF (40 mL) and H$_2$O (4 mL) was added SnCl$_2$·2H$_2$O (14.6 g, 77.3), and the mixture was stirred at 40° C. for 16 h. The reaction mixture was then slowly poured into saturated aq. NaHCO$_3$ (exothermic) and CH$_2$Cl$_2$. The resulting slurry was filtered through Celite, and the filter cake was rinsed with CH$_2$Cl$_2$. The organic phase was collected, dried over Na$_2$SO$_4$, and concentrated in vacuo to give a red oil. Purification by flash chromatography (10% EtOAc in hexanes) afforded the product as a colorless oil: $^1$H NMR (500 MHz, CDCl$_3$) δ 7.17 (d, J=1.5 Hz, 1H), 6.85 (d, J=1.5 Hz, 1H), 4.12 (br s, 2H), 3.44 (br s, 1H), 2.71 (s, 3H).

Step C. 7-Bromo-1-methyl-N-[4-(trifluoromethoxy)phenyl]-5-(trifluoromethyl)-1H-benzimidazol-2-amine To a solution of the title compound in Example 7, Step B (250 mg, 0.93 mmol) in CH$_2$Cl$_2$ (3 mL) was added 4-trifluoromethoxyphenyl isothiocyanate (218 µL, 1.34 mmol), and the mixture was stirred at 40° C. After 1 h, the reaction mixture was allowed to cool to ambient temperature. DMF (3 mL) was added, followed by mercury trifluoroacetate (646 mg, 1.51 mmol), and the mixture was stirred at 40° C. for 12 h. The mixture was then poured into EtOAc/saturated aq. Na$_2$S, and the resulting black slurry was filtered through Celite. The organic phase was collected, dried over Na$_2$SO$_4$, and concentrated in vacuo. Purification by flash chromatography (10% EtOAc/hexanes then 20% EtOAc/hexanes) provided the title compound as a white solid: $^1$H NMR (500 MHz, CD$_3$OD) δ 7.71 (d, J=9.0 Hz, 2H), 7.63 (s, 1H), 7.52 (s, 1H), 7.29 (d, J=9.0 Hz, 2H), 4.08 (s, 3H). LC-MS (ESI, Method B) 2.04 min, m/z 455.9 (M+3).

Step D. Methyl 4-[(4-bromo-6-trifluoromethyl-3-methyl-2-{[4-(trifluoromethoxy)-phenyl]imino}-2,3-dihydro-1H-benzimidazol-1-yl)methyl]benzoate To a mixture of the title compound in Example 7, Step C (38 mg, 0.084 mmol) and sodium hydride (6.0 mg, 60% suspension in mineral oil, 0.15 mmol) was added DMF (1 mL). After ten min, methyl-4-(bromomethyl)benzoate (38 mg, 0.168 mmol) was added, and the mixture was stirred at room temperature. After 12 h, the mixture was diluted with CH$_2$Cl$_2$ and poured in saturated aq. NaHCO$_3$/brine (1:1). The phases were separated, and the organic phase was dried over Na$_2$SO$_4$ and concentrated. The crude reaction mixture, a ca. 5:1 mixture regioisomers, was taken forward directly: $^1$H NMR (500 MHz, CDCl$_3$) δ 7.97 (d, J=8.0 Hz, 2H), 7.43 (s, 1H), 7.11 (d, J=8.5 Hz, 2H), 6.98 (d, J=8.5 Hz, 2H), 6.85 (s, 1H), 6.78 (d, J=8.0 Hz, 2H), 4.98 (s, 2H), 3.91 (s, 3H), 3.63 (s, 3H). LC-MS (ESI, Method B) 1.97 min, m/z 604.0 (M+1).

Step. E. 4-[(4-Bromo-3-methyl-2-{[4-(trifluoromethoxy)phenyl]-imino}-6-(trifluoromethyl)-2,3-dihydro-1H-benzimidazol-1-yl)methyl]-N-1H-tetrazol-5-ylbenzamide To a dioxane (1 mL) solution of the title compounds in Example 7, Step D was added LiOH (10 mg, 0.42 mmol) in 0.5 mL H$_2$O, and the reaction mixture was stirred at 40° C. After 1 h, the reaction mixture was diluted with EtOAc and washed with pH 7 phosphate buffer. The aqueous phase was extracted twice with EtOAc, and the combined organic phases were dried over Na$_2$SO$_4$ and concentrated. To the crude mixture of carboxylic acids were added EDC (161 mg, 0.84 mmol), HOBt (128 mg, 0.84 mmol), DMF (1.5 mL), DIEA (219 µL, 1.26 mmol) and 1H-tetraazol-5-amine monohydrate monohydrate (86 mg, 0.84 mmol). The reaction mixture was stirred at 40° C. for 12 h, then concentrated in vacuo. Purification by reverse-phase chromatography (20-80% CH$_3$CN/H$_2$O, each with 0.1% TFA) and lyophilization provided the title compound as a white solid. $^1$H NMR (500 MHz, d$_6$-DMSO) δ 12.40 (s, 1H), 7.99 (d, J=8.5 Hz, 2H), 7.57 (s, 1H), 7.51 (s, 1H), 7.25 (d, J=8.5 Hz, 2H), 7.12 (d, J=8.0 Hz, 2H), 6.90 (d, J=8.0 Hz 2H), 6.52 (br s, 1H), 5.22 (s, 2H), 3.57 (s, 3H); LC-MS (ESI, Method B) 1.75 min, m/z 655.0 (M+1).

EXAMPLE 8

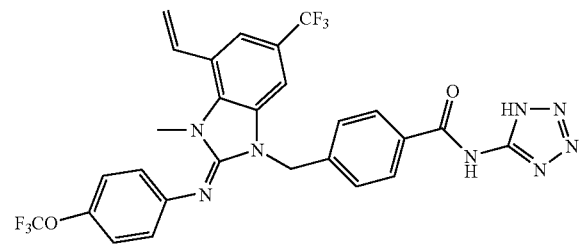

Step A. 1-methyl-N-[4-(trifluoromethoxy)phenyl]-5-(trifluoromethyl)-5-(trifluoromethyl)-7-vinyl-1H-benzimidazol-2-amine A nitrogen-purged flask was charged with AsPh$_3$ (44 mg, 0.12 mmol) and Pd$_2$(dba)$_3$ (34 mg, 0.037 mmol). In a separate flask, the title compound from Example 7, Step C (165 mg, 0.363 mmol) and vinyl tributylstannane (200 μL, 0.68 mmol) were dissolved in DMF. This solution was degassed by sparging with nitrogen, then transferred to the flask containing AsPh$_3$ and Pd$_2$(dba)$_3$, and the reaction mixture was stirred for 15 h at 60° C. The mixture was then cooled to room temperature, filtered through Celite, washed with brine, and concentrated. Purification by flash chromatography (10% EtOAc in hexanes then 25% EtOAc in hexanes) provided the title compound as a white solid: LC-MS (ESI, Method B) 1.80 min, m/z 402.3 (M+1).

Step B. Methyl 4-[(3-methyl-2-{[4-(trifluoromethoxy)-phenyl]imino}-6-(trifluoromethyl)4-vinyl-2,3-dihydro-1H-benzimidazol-1-yl)methyl]benzoate To a mixture of the title compound of Example 8, Step A (59 mg, 0.147 mmol) and sodium hydride (60% suspension in mineral oil, 8.9 mg, 0.221 mmol) was added DMF (1.5 mL). After ten min, methyl-4-(bromomethyl)benzoate (50.5 mg, 0.221 mmol) was added and the mixture was stirred at room temperature. After 1.5 h, the mixture was diluted with CH$_2$Cl$_2$ and poured in saturated aq. NaHCO$_3$/brine. The phases were separated, and the organic phase was dried over Na$_2$SO$_4$ and concentrated. The crude reaction mixture, a ca. 5:1 mixture of regioisomers, was taken forward directly: LC-MS (ESI, Method B) 1.95 min, m/z 550.3 (M+1).

Step C. 4-[(3-Methyl-2-{[4-(trifluoromethoxy)phenyl]imino}-6-(trifluoromethyl)4-vinyl-2,3-dihydro-1H-benzimidazol-1-yl)methyl]-N-1H-tetrazol-5-ylbenzamide To a solution of the title compounds from Example 8, Step B in dioxane (1 mL) was added LiOH (21 mg, 0.88 mmol) in 0.5 mL H$_2$O, and the reaction mixture was stirred at 40° C. After 1 h, the reaction mixture was diluted with EtOAc and washed with pH 7 phosphate buffer. The aqueous phase was extracted twice with EtOAc, and the combined organic phases were dried over Na$_2$SO$_4$ and concentrated. To the crude mixture of carboxylic acids were added EDC (253 mg, 1.32 mmol), HOBt (202 mg, 1.32 mmol), DMF (1 mL), DIEA (520 μL, 2.94 mmol) and 1H-tetraazol-5-amine monohydrate (151 mg, 1.47 mmol). The reaction mixture was stirred at 40° C. for 12 h, then concentrated under high vacuum. Purification by reverse-phase chromatography (20-80% CH$_3$CN/H$_2$O, both containing 0.1% TFA) followed by lyophilization provided the product as a white solid: $^1$H NMR (d$_6$-DMSO, 500 MHz) δ 12.40 (s, 1H), 8.00 (d, J=8.0 Hz, 2H), 7.65-7.00 (m, 7H), 7.33 (d, J=8.0 Hz, 2H), 5.90-5.22 (m, 6H), N-Me obscured by H$_2$O peak; LC-MS (ESI, Method B) 1.79 min, m/z 603.3 (M+1).

EXAMPLE 9

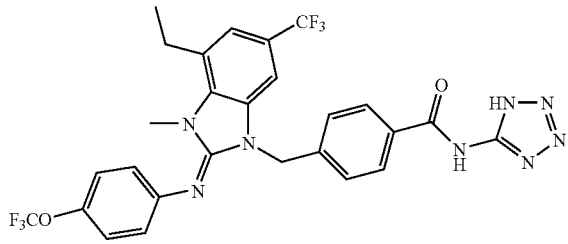

Step A. 7-Ethyl-1-methyl-5-N-[4-(trifluoromethoxy)phenyl]-5-(trifluoromethyl)-1H-benzimidazol-2-amine A solution of the title compound of Example 8, Step A (50 mg, 0.12 mmol) in MeOH (5 mL) was degassed by sparging with nitrogen, then was charged with 10% Pd/C (60 mg). The suspension was placed under a hydrogen atmosphere (balloon) and stirred rapidly for 24 h. After filtration through Celite and concentration in vacuo, the crude product was taken forward directly: LC-MS (ESI, Method B) 1.77 min, m/z 404.0 (M+1).

Step B. Methyl 4-[(4-ethyl-3-methyl-2-{[4-(trifluoromethoxy)-phenyl]imino}-6-(trifluoromethyl)-2,3-dihydro-1H-benzimidazol-1-yl)methyl]benzoate A flask containing the title compound from Example 9, Step A (36 mg, 0.089 mmol) was charged with sodium hydride (60% suspension in mineral oil, 5.4 mg, 0.134 mmol), and the mixture was dissolved in DMF (1.5 mL). After ten min, methyl-4-(bromomethyl)benzoate (31.5 mg, 0.134 mmol) was added and the mixture was stirred at room temperature. After 1.5 h, the mixture was diluted with CH$_2$Cl$_2$ and poured into saturated aq. NaHCO$_3$/brine. The phases were separated, and the organic phase was dried over Na$_2$SO$_4$ and concentrated. The crude reaction mixture, containing both N-benzylated regioisomers, was taken forward directly: LC-MS (ESI, Method B) 2.01 min, m/z 552.3 (M+1).

Step C. 4-[(4-Ethyl-3-methyl-2-{[4-(trifluoromethoxy)phenyl]-imino}-6-(trifluoromethyl)-2,3-dihydro-1H-benzimidazol-1-yl)methyl]-N-1H-tetrazol-5-ylbenzamide To a solution of the crude product from Example 9, Step B in dioxane (1 mL) was added LiOH (12.8 mg, 0.53 mmol) in 0.5 mL H$_2$O, and the reaction mixture was stirred at 40° C. After 1 h, the reaction mixture was diluted with EtOAc and washed with pH 7 phosphate buffer. The aqueous phase was extracted twice with EtOAc, and the combined organic phases were dried over Na$_2$SO$_4$ and concentrated. To the crude mixture of carboxylic acids were added EDC (154 mg, 0.80 mmol), HOBt (122 mg, 0.80 mmol), DMF (1.5 mL), DIEA (236 μL, 1.34 mmol) and 1H-tetraazol-5-amine monohydrate (92 mg, 0.89 mmol). The reaction mixture was stirred at 40° C. for 6 h, then concentrated under high vacuum. Purification by reverse-phase chromatography (20-65% CH$_3$CN/H$_2$O, both containing 0.1% TFA), followed by lyophilization, provided the product as a white solid: $^1$H NMR (500 MHz, d$_6$-DMSO) δ 12.43 (s, 1H), 8.03 (d, J=8.0 Hz, 2H), 7.50-7.20 (m, 7H), 7.34 (d, J=8.0 Hz, 2H), 5.51 (br s, 2H), 1.33 (t, J=7.0 Hz, 3H), C4-CH$_2$ and N-Me obscured by H$_2$O; LC-MS (ESI, Method A) 3.00 min, m/z 605.3 (M+1).

EXAMPLE 10

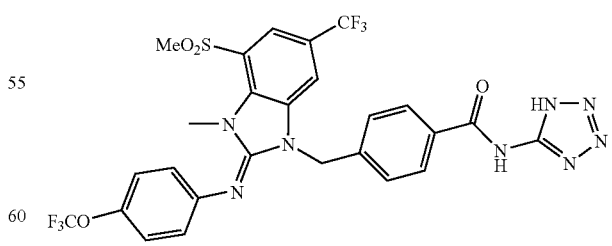

Step A. 1-Methyl-7-(ethylsulfonyl)-N-[4-(trifluoromethoxy)phenyl]-5-(trifluoromethyl)-1H-benzimidazol-2-amine To a suspension of the title compound from Example 7, Step C (45 mg, 0.10 mmol) and CuI (47 mg, 0.25 mmol) in DMSO (1 mL) was added sodium methanesulfinate (24 mg, 0.20 mmol), and the reaction mixture was stirred at 110° C. for 15 h. The mixture was allowed to cool to room temperature, then filtered through a cotton plug, and diluted with EtOAc. The filtrate was washed with water and brine, then concentrated in vacuo. Purification by flash chromatography (20% EtOAc in hexanes then 100% EtOAc) provided the title compound as a white solid: $^1$H NMR (500 MHz, CD$_3$OD) δ 7.99 (s, 1H), 7.95 (s, 1H), 7.79 (d, J=8.5 Hz, 2H), 7.32 (d, J=8.5 Hz, 2H), 4.20 (s, 3H), 3.43 (s, 3H). LC-MS (ESI, Method B) 2.42 min, m/z 454.2 (M+1).

Step B. Methyl 4-[(3-methyl-4-methylsufonyl-2-{[4-(trifluoromethoxy)-phenyl]imino}-6-(trifluoromethyl)-2,3-dihydro-1H-benzimidazol-1-yl)methyl]benzoate A flask containing the title compound from Example 10, Step A (30 mg, 0.066 mmol) was charged with sodium hydride (60% suspension in mineral oil, 4.0 mg, 0.10 mmol), and the mixture was dissolved in DMF (1.5 mL). After ten minutes, methyl4-(bromomethyl)benzoate (18 mg, 0.077 mmol) was added and the mixture was stirred at room temperature. After 15 h, the mixture was diluted with CH$_2$Cl$_2$ and poured in saturated aq. NaHCO$_3$/brine. The phases were separated, and the organic phase was dried over Na$_2$SO$_4$ and concentrated. The crude reaction mixture, containing both N-benzyl regioisomers, was taken forward directly: LC-MS (ESI, Method B) 2.25 min, m/z 602.3 (M+1).

Step C. 4-[(3-methyl4-methylsufonyl-2-{[4-(trifluoromethoxy)-phenyl]imino}-6-(trifluoromethyl)-2,3-dihydro-1H-benzimidazol-1-yl)methyl]-N-1H-tetrazol-5-ylbenzamide To a solution of the crude product from Example 10, Step B in dioxane (1 mL) was added LiOH (9.5 mg, 0.04 mmol) in 0.5 mL H$_2$O, and the reaction mixture was stirred at 40° C. After 1 h, the reaction mixture was diluted with EtOAc and washed with pH 7 phosphate buffer. The aqueous phase was extracted twice with EtOAc, and the combined organic phases were dried over Na$_2$SO$_4$ and concentrated. To the crude mixture of carboxylic acids were added EDC (113 mg, 0.59 mmol), HOBt (91 mg, 0.59 mmol), DMF (1 mL), DIEA (230 μL, 1.32 mmol) and 1H-tetraazol-5-amine monohydrate (68 mg, 0.66 mmol). The reaction mixture was stirred at 40° C. for 12 h, then concentrated under high vacuum. Purification by reverse-phase chromatography (20-80% CH$_3$CN/H$_2$O, both containing 0.1% TFA), followed by lyophilization, provided the product as a white solid: $^1$H NMR (500 MHz, d$_6$-DMSO) δ 12.40 (s, 1H), 8.00 (d, J=8.5 Hz, 2H), 7.84 (s, 1H), 7.79 (s, 1H), 7.22 (d, J=8.5 Hz, 2H), 7.20 (br s, 1H), 7.12 (d, J=8.0 Hz, 2H), 6.87 (d, J=8.0 Hz, 2H), 5.24 (s, 2H), 3.66 (s, 3H), 3.56 (s, 3H); LCMS (ESI,) 1.97 min, m/z 655.2 (M+1).

EXAMPLE 11

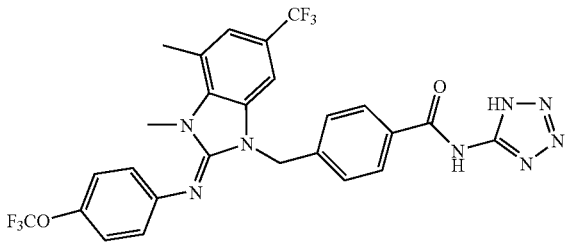

Step A. 1,7-Dimethyl-N-[4-(trifluoromethoxy)phenyl]-5-(trifluoromethyl)-1H-benzimidazol-2-amine A nitrogen-purged flask was charged with AsPh$_3$ (32 mg, 0.0.88 mmol) and Pd$_2$(dba)$_3$ (20 mg, 0.022 mmol). In a separate flask, the title compound from Example 7, Step C (100 mg, 0.22 mmol) and tetramethyltin (40 μL, 0.29 mmol) were dissolved in DMF (1.5 ml). This solution was then transferred to the flask containing AsPh$_3$ and Pd$_2$(dba)$_3$, and the reaction mixture was stirred for 15 h at 75° C. The mixture was then cooled to room temperature, filtered through Celite, washed with brine, and concentrated. Purification by flash chromatography (10% EtOAc/hexanes then 25% EtOAc/hexanes) provided the title compound as a colorless oil: LC-MS (ESI, Method B) 2.06 min, m/z 390.2 (M+1).

Step B. Methyl 4-[(3,4-dimethyl-2-{[4-(trifluoromethoxy)-phenyl]imino}-6-(trifluoromethyl)-2,3-dihydro-1H-benzimidazol-1-yl)methyl]benzoate A flask containing the title compound from Example 11, Step A (20 mg, 0.051 mmol) was charged with sodium hydride (60% suspension in mineral oil, 3.0 mg, 0.077 mmol), and the mixture was dissolved in DMF (1 mL). After ten minutes, methyl-4-(bromomethyl)benzoate (18 mg, 0.077 mmol) was added and the mixture was stirred at room temperature. After 15 h, the mixture was diluted with CH$_2$Cl$_2$ and poured in saturated aq. NaHCO$_3$/brine. The phases were separated, and the organic phase was dried over Na$_2$SO$_4$ and concentrated. The crude reaction mixture, containing both N-benzyl regioisomers, was taken forward directly: LC-MS (ESI, Method B) 2.24 min, m/z 538.1 (M+1); 2.60 min, m/z 538.1 (M+1).

Step C. 4-[(3,4-dimethyl-2-{[4-(trifluoromethoxy)-phenyl]imino}-6-(trifluoromethyl)-2,3-dihydro-1H-benzimidazol-1-yl)methyl]-N-1H-tetrazol-5-ylbenzamide To a solution of the crude product from Example 11, Step B in dioxane (1 mL) was added LiOH (10 mg, 0.04 mmol) in 0.5 mL H$_2$O, and the reaction mixture was stirred at 40° C. After 1 h, the reaction mixture was diluted with EtOAc and washed with pH 7 phosphate buffer. The aqueous phase was extracted twice with EtOAc, and the combined organic phases were dried over Na$_2$SO$_4$ and concentrated. To the crude mixture of carboxylic acids were added EDC (113 mg, 0.59 mmol), HOBt (91 mg, 0.59 mmol), DMF (1 mL), DIEA (230 μL, 1.29 mmol) and 1H-tetraazol-5-amine monohydrate (68 mg, 0.66 mmol). The reaction mixture was stirred at 40° C. for 12 h, then concentrated under high vacuum.

Purification by reverse-phase chromatography (20-75% $CH_3CN/H_2O$, both containing 0.1% TFA), followed by lyophilization, provided the product as a white solid: $^1H$ NMR (500 MHz, $d_6$-DMSO) δ 12.40 (s, 1H), 8.01 (d, J=8.0 Hz, 2H), 7.60-6.50 (m, 7H), 7.33 (d, J=8.0 Hz, 2H), 5.47 (s, 2H), 3.64 (s, 3H), 3.62 (s, 3H); LC-MS (ESI, Method B) 2.00 min, m/z 591.3 (M+1).

EXAMPLE 12

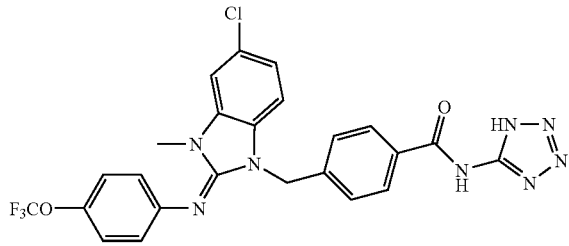

Step A. Methyl 4-{[(4-chloro-2-nitrophenyl)amino]methyl}benzoate

To 4-chloro-2-nitroaniline (10 mmol, 1.73 g) in DMF (10 mL) was added NaH (11 mmol, 440 mg of 60% suspension in mineral oil). After 30 min the reaction vessel was placed in a water bath and methyl-4-(bromomethyl)benzoate (11 mmol, 2.52 g) was added (exothermic). The reaction mixture was allowed to stand at ambient temperature for 16 h, then poured into saturated $NaHCO_3$, affording an orange precipitate which was filtered, washed with water and dried in vacuo. Purification by flash chromatography on silica eluting with 15% EtOAc in hexanes provided the product as an orange solid. LC-MS (ESI, Method C) 3.79 min, m/z 321.1 (M+1).

Step B. Methyl 4-{[(2-amino-4-chlorophenyl)amino]methyl}benzoate

The title compound of Example 12, Step A (3.6 mmol, 1.2 g) and $SnCl_2.2H_2O$ (18 mmol, 4 g) were heated in DMP (10 mL) at 40° C. for 3 hr. The reaction mixture was poured into EtOAc and concentrated $NaHCO_3$ and stirred. The resulting mixture was filtered over celite, and the filter cake was washed with EtOAc. The organic phase was collected, dried with $Na_2SO_4$ and reduced in vacuo. Flash chromatography on silica eluting with 20% and 30% EtOAc in hexanes afforded the product as a pale white solid. $^1H$ NMR (500 MHz, $d_6$-DMSO) δ 7.94 (d, J=8.2 Hz, 2H), 7.49 (d, J=8.2 Hz, 2H), 6.70 (s, 1H), 6.32 (s, 1H), 5.68 (t, J=5.8 Hz, 1H), 5.07 (s, 2H), 4.41 (d, J=5.7 Hz, 2H), 3.85 (s, 3H). LC-MS (ESI, Method C) 3.33 min, 291.2 (M+1).

Step C. Methyl 4-[(5-chloro-2-{[4-(trifluoromethoxy)-phenyl]amino}-1H-benzimid-azol-1-yl)methyl]benzoate The title compound of Example 12, Step B (0.5 mmol, 145 mg) and 4-trifluoromethoxyphenyl isothiocyanate (0.5 mmol, 81 μL) were heated in DCM (1 mL) for 1 h, then allowed to stand at ambient temperature for 16 h. MeI (1.0 mmol, 62 μL), DIEA (1.0 mmol, 174 μL) and DMF (0.5 mL) were added and the solution was heated at 40° C. for 2 h. The reaction mixture was partitioned between EtOAc/brine and the organic phase was dried with $Na_2SO_4$ and concentrated in vacuo. Flash chromatography on silica eluting with 18% EtOAc in hexanes afforded the product as a beige solid. LC-MS (ESI, Method C): 3.85 min, m/z 476.1 (M+1).

Step D. Methyl 4-[(5-chloro-3-methyl-2-{[4-(trifluoromethoxy)-phenyl]imino}-2,3-dihydro-1H-benzimidazol-1-yl)methyl]benzoate The title compound in Example 12, Step C (0.08 mmol, 36 mg) and NaH (0.1 mmol, 4 mg of a 60% suspension in mineral oil) were taken up in DMF (0.5 mL). After 10 min. MeI (0.15 mmol, 9 μL) was added and the reaction was allowed to stand at ambient temperature. After 1 h the reaction was partitioned into $NaHCO_3/CH_2Cl_2$. The organic phase was dried over $Na_2SO_4$ and reduced in vacuo to afford a mixture of N-methyl regioisomers, which was taken on directly. LC-MS (ESI, Method C) 2.95 min, m/z 490.0 (M+1).

Step E. 4-[(5-Chloro-3-methyl-2-{[4-(trifluoromethoxy)phenyl]-imino}-2,3-dihydro-1H-benzimidazol-1-yl)methyl]-N-1H-tetrazol-5-ylbenzamide The residue from Example 12, Step D was taken up in dioxane (1 mL) and a solution of LiOH (1 mmol, 24 mg) in $H_2O$ (0.5 mL) was added. The reaction was stirred at 40° C. for 1 h, then partitioned between EtOAc and brine buffered to pH 7. The organic phase was dried with $Na_2SO_4$ and reduced in vacuo. To the residue was added a solution of 1H-tetraazol-5-amine monohydrate (0.2 mmol, 21 mg), EDC (0.2 mmol, 38 mg), HOBt (0.2 mmol, 31 mg) and DIEA (0.3 mmol, 52 μL) in DMF (1 mL). The reaction mixture was heated for 2 h at 40° C. Reverse-phase chromatography (20-60% $MeCN/H_2O$, both containing 0.1% TFA) and lyophilization afforded the product as a white solid. $^1H$ NMR (500 MHz, $d_6$-DMSO) δ 12.42 (s, 1H), 8.04 (d, J=8.4 Hz, 2H), 7.87 (br m, 1H), 7.45 (br m, 1H), 7.39 (br m, 1H), 7.36 (d, J=8.2 Hz, 2H), 7.31 (br d, J=8.2 Hz, 2H), 7.24 (br m, 2H), 5.45 (s, 2H), N-Me obscured by $H_2O$ peak. LC-MS (ESI, Method C) 2.50 min, m/z 543.1 (M+1).

EXAMPLE 13

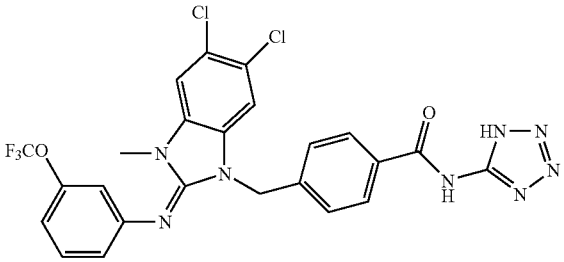

Step A. Methyl 4-{[(2-amino-4,5-dichlorophenyl)amino]methyl}benzoate 4,5-Dichloro-2-nitroaniline (10 mmol, 2.07 g), 4-bromomethylbenzoate (10 mmol, 2.29 g) and $K_2CO_3$ (12 mmol, 1.66 g) were stirred in DMF (10 mL) at ambient temperature for 16 h. The reaction mixture was partitioned between $CH_2Cl_2$ and brine, and the organic phase was dried with Na$_2$SO$_4$ and concentrated in vacuo. The monobenzylated product was obtained by flash chromatography on silica eluting with 15% EtOAc in hexanes as a bright orange solid. A portion of the nitro compound (7.4 mmol, 2.6 g) and SnCl$_2$.2 H$_2$O (22 mmol, 5.0 g) were heated in 40 mL of DMF at 40° C. for 16 h. The reaction mixture was poured into EtOAc and saturated NaHCO$_3$ and stirred to afford a precipitate, which was removed by filtration through celite. The organic phase was dried with Na$_2$SO$_4$ and concentrated in vacuo to a brown oil. Flash chromatography on silica eluting with a step gradient of 20%, 30% and 35% EtOAc in hexanes provided the product as a pale yellow solid. LC-MS (ESI, Method C) 3.54 min, m/z 325.2 (M+1).

Step B. Methyl 4-[(5,6-dichloro-2-{[3-(trifluoromethoxy)phenyl]amino}-1H-benzimid-azol-1-yl)methyl]benzoate To a solution of 3-trifluoromethyoxyphenylaniline (0.2 mmol, 35 mg, 27 µL) and DIEA (0.5 mmol, 87 µL) in 0.5 mL of CH$_2$Cl$_2$ was added thiophosgene (0.2 mmol, 15 µL) via syringe. The solution was allowed to stand at ambient temperature for 1 h, and the title compound in Example 13, Step A (0.2 mmol, 65 mg) was added. The reaction mixture was heated at 40° C. for 1 h, then Hg(O$_2$CCF$_3$)$_2$ was added. The reaction was heated at 40° C. for 2 h, and allowed to stand at ambient temperature for 16 h. The slurry was poured into EtOAc and saturated NaHCO$_3$ containing Na$_2$S, then filtered through celite. The organic phase was dried with Na$_2$SO$_4$ and concentrated in vacuo. Flash chromatography on silica eluting with 20% and 35% EtOAc in hexanes afforded the product as a beige solid. LC-MS (ESI, Method B) 2.14 min, m/z 524.1 (M+1).

Step C. Methyl 4-[(5,6-dichloro-3-methyl-2-{[3-(trifluoromethoxy)-phenyl]imino}-2,3-dihydro-1H-benzimidazol-1-yl)methyl]benzoate The title compound in Example 13, Step B (0.1 mmol, 51 mg) and NaH (0.2 mmol, 8 mg of a 60% suspension in mineral oil) were taken up in 0.7 mL of DMF. After 10 min MeI (0.2 mmol, 13 µL) was added to the reaction. After 15 h the reaction was not complete, so an additional 0.2 mmol of NaH and MeI were added to the reaction. After 2 h the reaction was partitioned between NaHCO$_3$/DCM. The organic phase was dried over Na$_2$SO$_4$ and reduced in vacuo. The product was isolated by preparative TLC on silica eluting with 20% EtOAc/hexanes (LC-MS), and taken on directly. LC-MS (ESI, Method B) 2.38 min, m/z 510.2 (M+1).

Step D. 4-[(5,6-Dichloro-3-methyl-2-{[3-(trifluoromethoxy)phenyl]-imino}-2,3-dihydro-1H-benzimidazol-1-yl)methyl]-N-1H-tetrazol-5-ylbenzamide To a solution of the title compound of Example 13, Step C in dioxane (4 mL), was added a solution of LiOH (2 mmol, 48 mg) in H$_2$O (2 mL). The reaction was stirred at ambient temperature for 16 h, then was partitioned into EtOAc/brine buffered to pH 7. The organic phase was dried with Na$_2$SO$_4$ and concentrated in vacuo. To the residue was added a solution of 1H-tetraazol-5-amine monohydrate (0.2 mmol, 21 mg), EDC (0.2 mmol, 38 mg), HOBt (0.2 mmol, 31 mg) and DIEA (0.3 mmol, 52 µL) in DMF (1 mL). The resulting reaction mixture was heated for 2 h at 40° C., and the product was isolated by reverse-phase chromatography (20-60% MeCN/H$_2$O, both containing 0.1% TFA). Lyophilization afforded the product as a white solid. $^1$H NMR (500 MHz, d$_6$-DMSO) δ 12.42 (s, 1H), 8.05 (d, J=8.2 Hz, 2H), 7.85 (br s, 1H), 7.70 (br s, 1H), 7.35-7.42 (overlapping m, 3H), 6.97-7.09 (overlapping m, 3H), 5.36 (s, 2H), 3.33 (s, 3H). LC-MS (ESI, Method B) 1.93 min, m/z 577.0 (M+1).

EXAMPLE 14

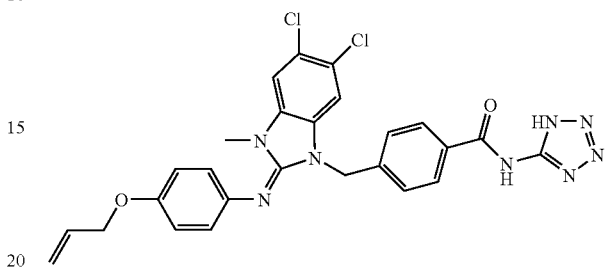

Step A. 4-(Allyloxy)aniline

To a solution of 4-nitrophenol (20 mmol, 2.78 g) in DMT (12 mL) was added K$_2$CO$_3$ (24 mmol, 3.31 g) and alkyl bromide (20 mmol, 1.73 mL). The slurry was stirred for 16 h at ambient temperature, then partitioned between CH$_2$Cl$_2$ and saturated NaHCO$_3$. The organic phase was dried with Na$_2$SO$_4$ and concentrated in vacuo to afford a brown oil. The oil was taken up in 10% H$_2$O/DMF (33 mL). SnCl$_2$.2H$_2$O (77 mmol, 17.3 g) was added and the reaction was stirred at 40° C. for 16 h. The mixture was poured into saturated NaHCO$_3$ and CH$_2$Cl$_2$ and stirred briefly, then filtered through celite. The organic phase was collected and dried with MgSO$_4$ and concentrated in vacuo. Flash chromatography on silica eluting with 20% EtOAc in hexanes afforded the product as a brown oil. LC-MS (ESI, Method B): 1.09 min, m/z 150.1 (M+1).

Step B. N-[4-(Allyloxy)phenyl]-5,6-dichloro-1H-benzimidazol-2-amine

To a stirring solution of the title compound of Example 14, Step A (2.5 mmol, 373 mmol) and DIEA (2.75 mmol, 478 µL) in CH$_2$Cl$_2$ (4 mL) at 0° C. was added thiophosgene (2.5 mmol, 191 µL). The solution was allowed to reach ambient temperature for 1 h, and 4,5-dichloro-1,2-phenylenediamine (2.5 mmol, 443 mg) was added to the reaction. The reaction mixture was heated to 40° C. for 16 h. MeI (5 mmol, 312 µL) was added, and the reaction was heated at 40° C. for 16 h. Aqueous workup with CH$_2$Cl$_2$ and brine, followed by flash chromatography on silica eluting with 3% MeOH in CH$_2$Cl$_2$ afforded the product as a brown solid. LC-MS (ESI, Method B): 1.79 min, m/z 334.1 (M+1).

Step C Methyl 4-[(2-{[4-(alkyloxy)phenyl]amino}-5,6-dichloro-1H-benzimidazol-1-yl)methyl]benzoate To the title compound of Example 14, Step B (2.2 mmol, 720 mg) in DMF (5 mL) was added NaH (2.6 mmol, 105 mg of 60% suspension in mineral oil). After 5 min methyl-4-(bromomethyl)benzoate (2.2 mmol, 502 mg) was added and the reaction mixture was left at ambient temperature for 16 h. Aqueous workup in CH$_2$Cl$_2$/brine, followed by flash chromatography on silica eluting with 3% MeOH in CH$_2$Cl$_2$ afforded the product as a brown oil. LC-MS (ESI, Method B): 2.07 mnin, m/z 482.2 (M+1).

Step D. Methyl 4-[(2-{[4-(alkyloxy)-phenyl]imino}-5,6-dichloro-3-methyl-2,3-dihydro-1H-benzimidazol-1-yl)methyl]benzoate To a solution of the title compound of Example 14, Step C (0.1 mmol, 46 mg) in DMF (1 mL) was added NaH (0.12 mmol, 5 mg of 60% suspension in mineral oil). After 5 min MeI (0.2 mmol, 12 µL) was added. After 1.5 h the reaction mixture was partitioned between $CH_2Cl_2$ and saturated $NaHCO_3$. The organic phase was dried with $MgSO_4$ and concentrated in vacuo to afford the product and the N-methyl regioisomer. LC-MS (ESI, Method B): 2.06 min, m/z 496.2 (M+1).

Step E. 4-[(2-{[4-(Allyloxy)-phenyl]imino}-5,6-dichloro-3-methyl-2,3-dihydro-1H-benzimidazol-1-yl)methyl]-N-1H-tetrazol-5-ylbenzamide To the product of Example 14, Step D (0.6 mmol, 30 mg) dissolved in 0.8 mL of dioxane was added a solution of LiOH (0.4 mmol, 10 mg) in 0.4 mL of $H_2O$. The reaction was stirred at 40° C. fo 1 h, then partitioned between EtOAc/pH 7 phosphate buffer. The organic phase was dried with $MgSO_4$ and concentrated under reduced pressure to afford an amber foam. The foam was taken up in a solution of 1H-tetraazol-5-amine monohydrate (0.18 mmol, 19 mg), HOBt (0.12 mmol, 18 mg), EDC (0.12 mmol, 23 mg) and DIEA (0.18 mmol, 31 µL) in DMF (1 mL). The reaction mixture was heated to 40° C. for 1 h, then concentrated under reduced pressure. The residue was taken up in 2:1 dioxane/$H_2O$, acidified with TFA, and purified by reverse-phase chromatography (20-60% MeCN/$H_2O$, both containing 0.1% TFA). Lyophilization afforded the title compound as a white solid. $^1$H NMR ($d_6$-DMSO+$NEt_3$, 500 MHz) δ 7.90 (br d, J=7.1 Hz, 2H), 7.35 (s, 1H), 7.28-7.26 (overlapping s, d, 3H), 6.79 (m, 2H), 6.76 (m, 2H), 6.03 (m, 1H), 5.39 (dd, J=15.6 Hz, 1.8 Hz, 1H), 5.25 (d, J=10.3 Hz, 1H), 5.08 (s, 2H), 4.50 (d, J=5.2 Hz, 2H), 3.12 (s, 3H). LC-MS (ESI, Method A): 2.99 min, m/z=549.2 (M+1).

EXAMPLE 15

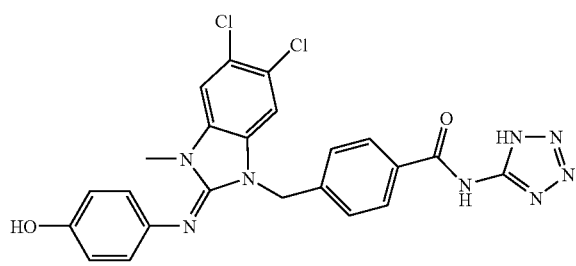

4-[(5,6-Dichloro-2-{[4-(hydroxy)phenyl]-imino}-3-methyl-2,3-dihydro-1H-benzimidazol-1-yl)methyl]-N-1H-tetrazol-5-ylbenzamide $Pd_2.dba_3$ (0.025 mmol, 23 mg) and 1,4-bis(diphenylphosphinyl)butane (0.05 mmol, 21 mg) were combined in 0.5 mL of THF under $N_2$. After 15 min the Pd solution was transferred via syringe to a separate flask containing the title compound of Example 14, Step E (0.015 mmol, 8 mg) and 1,3-dimethylbarbituric acid (0.02 mmol, 3 mg) in $CH_2Cl_2$ (0.7 mL). The reaction was allowed to stand at ambient temperature for 1 h. Reverse-phase chromatography (10-80% MeCN/$H_2O$, both containing 0.1% TFA), and lyophilization provided the product as a white solid. $^1$H NMR ($d_6$-DMSO+$NEt_3$, 500 MHz) δ 7.90 (broad d, 2H), 7.32 (s, 1H), 7.29 (broad d, 2H), 7.25 (s, 1H), 6.65 (m, 2H), 6.61 (m, 2H), 5.10 (s, 2H), 3.10 (s, 3H). LC-MS (ESI, Method A): 2.71 min, m/z 509.1 (M+1).

EXAMPLE 16

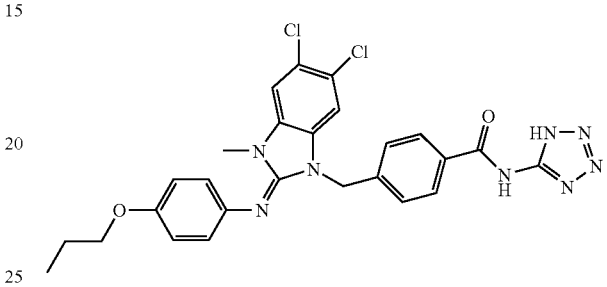

Step A. Methyl 4-[(5,6-dichloro-2-{[4-(hydroxy)-phenyl]imino}-3-methyl-2,3-dihydro-1H-benzimidazol-1-yl)methyl]benzoate $Pd_2dba_3$ (0.025 mmol, 23 mg) and 1,4-bis(diphenylphosphinyl)butane (0.05 mmol, 21 mg) were combined in 0.5 mL of THF under $N_2$. After 15 min the Pd solution was transferred via syringe to a separate flask containing the title compound of Example 14, Step D (0.1 mmol, 55 mg) and 1,3-dimethylbarbituric acid (0.12 mmol, 19 mg) in DCM (1 mL). The reaction mixture was allowed to stand at ambient temperature for 1 h. The product was isolated by chromatography on silica eluting with 3% MeOH in $CH_2Cl_2$. LC-MS (ESI, Method B): 1.86 min, m/z 456.1 (M+1).

Step B. Methyl 4-[(5,6-dichloro-3-methyl-2-{[4-(propyloxy)-phenyl]imino}-2,3-dihydro-1H-benzimidazol-1-yl)methyl]benzoate To the title compound of Example 16, Step A (0.04 mmol, 20 mg) in $CH_2Cl_2$ (0.7 mL) was added 1-propanol (0.1 mmol, 7 µL), DIAD (0.08 mmol, 16 µL) and $Ph_3P$ (0.08 mmol, 11 mg). After 1 h the reaction was not complete, so additional 1-propanol (0.1 mmol), DIAD (0.8 mmol) and $Ph_3P$ (0.08 mmol) were added. After 4 h the product was isolated by flash chromatography on silica eluting with 10% and 25% EtOAc in hexanes as a colorless oil. LC-MS (ESI, Method A): 3.40 min, m/z 498.2 (M+1).

Step C. 4-[(5,6-Dichloro-3-methyl-2-{[4-(propyloxy)phenyl]-imino}-2,3-dihydro-1H-benzimidazol-1-yl)methyl]-N-1H-tetrazol-5-ylbenzamide To the title compound of Example 16, Step B (0.04 mmol, 19 mg) dissolved in 0.8 mL of dioxane was added a solution of LiOH (0.4 mmol, 10 mg) in 0.4 mL of $H_2O$. The reaction was stirred at 40° C. for 2 h. The product was partitioned between EtOAc/pH 7 phosphate buffer. The organic phase was dried with $MgSO_4$ and concentrated under reduced pressure to provide a white foam. To the foam was added a solution of 1H-tetraazol-5-amine monohydrate (0.12 mmol, 12 mg), HOBt (0.08 mmol, 12 mg), EDC (0.08 mmol, 15 mg) and DIEA (0.12 mmol, 21 μL) in DMF (1 mL). The reaction mixture was heated to 40° C. for 2 h, then concentrated under reduced pressure. Purification by reverse-phase chromatography (20-60% MeCN/H₂O, both containing 0.1% TFA), and lyophilization afforded the title compound as a white solid. ¹H NMR (d₆-DMSO+NEt₃, 500 MHz) δ 7.90 (broad d, J=6.8 Hz, 2H), δ 7.34 (s, 1H), δ 7.29-7.26 (overlapping s, d, 3H), δ 7.78-7.74 (overlapping m, 4H), δ 5.08 (s, 2H), δ 3.86 (t, J=6.4 Hz, 2H), δ 3.11 (s, 3H), δ 1.71 (m, J=7.3 Hz, 2H), δ 0.97 (t, obscured by NEt₃). LC-MS (ESI, Method A): 2.97 min, m/z 551.2 (M+1).

EXAMPLE 17

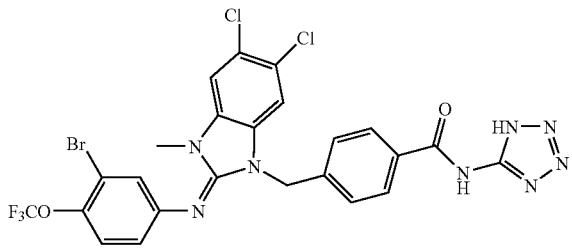

Step A. Methyl 4-[(2-{[3-bromo-4-(trifluoromethoxy)-phenyl]amino}-5,6-dichloro-1H-benzimidazol-1-yl)methyl]benzoate To a flask containing 3-bromo-4-trifluoromethoxyaniline (2 mmol, 512 mg) and DIEA (4.5 mmol, 780 μL) in CH₂Cl₂ (10 mL) in a cold water bath was added thiophosgene (2 mmol, 153 μL) (exothermic). After 30 min 4,5-dichloro-1,2-phenylenediamine (2.2 mmol, 389 mg) was added. After 1 h MeI (4 mmol, 2.28 mg) and DIEA (2.3 mmol, 400 μL) were added, and the resulting solution was allowed to stand at ambient temperature for 16 h. The reaction mixture was partitioned between sat. NaHCO₃ and CH₂Cl₂ and the organic phase was washed with brine, dried with Na₂SO₄ and concentrated in vacuo. Flash chromatography on silica eluting with 30% and 40% EtOAc in hexanes provided the benzimidazole as a beige solid. To a portion of the solid (0.4 mmol, 176 mg) in DMF (2 mL) was added NaH (0.44 mmol, 18 mg of 60% suspension in mineral oil). After 10 min methyl-4-(bromomethyl)benzoate (0.4 mmol, 92 mg) was added and the reaction mixture was left at ambient temperature for 5 h. The reaction mixture was poured into saturated NaHCO₃, causing formation of a precipitate, which was filtered, washed with water and dried in vacuo. Flash chromatography on silica eluting with 25% and 35% EtOAc in hexanes afforded the product as a beige solid. ¹H NMR (500 MHz, d₆-DMSO) δ 9.65 (s, 1H), 8.41 (d, J=2.7 Hz, 1H), 7.89-7.96 (overlapping m, 3H), 7.74 (s, 1H), 7.58 (s, 1H), 7.53 (m, 1H), 7.26 (d, J=8.5 Hz, 2H), 5.67 (s, 2H), 3.82 (s, 3H). LC-MS (ESI, Method B): 2.68 min, m/z 590.0 (M+1).

Step B. Methyl 4-[(2-{[3-bromo4-(trifluoromethoxy)-phenyl]imino}-5,6-dichloro-3-methyl-1H-benzimidazol-1-yl)methyl]benzoate To a solution of the title compound of Example 17, Step A (0.15 mmol, 88 mg) in DMF (1 mL) was added NaH (0.2 mmol, 8 mg of 60% suspension in mineral oil). After 5 min MeI (0.2 mmol, 13 μL) was added. After 2 h the reaction mixture poured into saturated NaHCO₃, causing formation of a precipitate which was filtered, washed with water and dried in vacuo. Preparative TLC on silica with a mobile phase of 25% EtOAc in hexanes afforded the product as a white solid. LC-MS ESI, Method C) 4.18 min, m/z 604.0 (M+3).

Step C. 4-[(2-{[3-bromo-4-(trifluoromethoxy)-phenyl]imino}-5,6-dichloro-3-methyl-1H-benzimidazol-1-yl)methyl]-N-1H-tetrazol-5-ylbenzamide To the title compound of Example 17, Step B (0.06 mmol, 35 mg) dissolved in dioxane (2 mL) was added a solution of LiOH (1.0 mmol, 24 mg) in H₂O (1 mL). The reaction was stirred at 40° C. for 2 h, and at ambient temperature for 16 h. The product was partitioned between EtOAc and brine buffered to pH 7. The organic phase was dried with MgSO₄ and concentrated under reduced pressure to afford a white solid. To the solid was added a solution of 1H-tetraazol-5-amine monohydrate (0.2 mmol, 21 mg), HOBt (0.2 mmol, 31 mg), EDC (0.2 mmol, 38 mg) and DIEA (0.3 mmol, 52 μL) in DMF (1 mL). The reaction mixture was heated to 40° C. for 2 h, then allowed to stand at ambient temperature for 16 h. The solution was concentrated under reduced pressure, and the residue was taken up in ca. 2:1 dioxane/H₂O, acidified with TFA, and purified by reverse-phase chromatography (20-60% MeCN in H₂O, both containing 0.1% TFA). Lyophilization afforded the title compound as a white solid. ¹H NMR (500 MHz, d₆-DMSO) δ 12.39 (s, 1H), 8.01 (d, J=8.4 Hz, 2H), 7.68 (s, 1H), 7.55 (s, 1H), 7.28-7.34 (overlapping m, 3H), 7.24 (s, 1H), 6.97 (m, 1H), 5.21 (s, 2H), 3.26 (s, 3H). LC-MS (ESI, Method C): 3.59 min, m/z 657.0 (M+3).

EXAMPLE 18

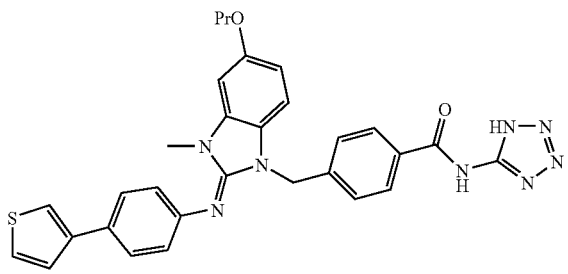

Step A. 2-Fluoro-4-propoxynitrobenzene

To a solution of the 3-fluoro-4-nitrophenol (32 mmol, 5.0 g), 1-propanol (48 mmol, 3.9 mL), and triphenylphosphine (64 mmol, 16.8 g) in CH₂Cl₂ (160 mL) at 0° C. was added DIAD (64 mmol, 12 mg). The reaction mixture was concentrated in vacuo. The product was isolated by flash chromatography on silica eluting with 5% EtOAc in hexanes. H¹ NMR (500 MHz, CDCl₃): δ 8.13 (t, J=8.7 Hz, 1H), 6.81-6.75 (m, 2H), 4.05 (d, J=6.4 Hz, 2H), 1.90 (m, 2H), 1.10 (t, J=7.3 Hz, 3H).

Step B. N-Methyl-2-nitro-5-propoxyaniline

To a solution of the title compound in Example 18, Step A (32 mmol, 6.4 g) in methanol (20 mL) was added methylamine (2.0 M in methanol, 22 nL). After 16 h, the reaction mixture was concentrated in vacuo to afford a yellow solid. $H^1$ NMR (500 MHz, $CDCl_3$) δ 8.18 (d, J=9.6 Hz, 1H), 6.28 (dd, J=2.5, 9.4 Hz, 1H), 6.17 (d, J=2.5 Hz, 1H), 4.04 (t, J=6.4 Hz, 2H), 3.04 (d, J=5.1 Hz, 3H), 1.88 (m, 2H), 1.10 (t, J=7.5Hz, 3H). LC-MS (ESI, Method C) 3.43 min, m/z 211.2 (M+1).

Step C. $N^1$-Methyl-5-propoxybenzene-1,2-diamine

To a solution of the title compound in Example 18, Step B (0.492 mmol, 45 mg) in methanol (20 mL) was added palladium hydroxide on carbon (20% by weight, 60 mg). The reaction was stirred under a balloon of hydrogen. After 1.5 h, the reaction mixture concentrated in vacuo, redissolved in ethylacetate, washed with brine, dried with $Na_2SO_4$, and concentrated in vacuo. $H^1$ NMR (500 MHz, $d_6$-DMSO): δ 6.63 (d, J=8.2 Hz, 1H), 6.27 (d, J=2.5 Hz, 1H), 6.19 (d, J=7.1 Hz, 1H), 3.88 (t, J=6.6 Hz, 2H), 3.23 (bs, 1H), 2.84 (s, 3H), 1.80 (m, 2H), 1.04 (t, J=7.5 Hz, 3H). LC-MS (ESI, Method B) 1.37 min, m/z 181.1 (M+1).

Step D. N-[4-iodophenyl]-1-methyl-6-propoxy-1H-benzimidazol-2-amine

To a solution of the title compound in Example 18, Step C (2.7 mmol, 487 mg) in $CH_2Cl_2$ (5 mL) was added 4-iodophenyl isothiocyanate (2.25 mmol, 588 mg). After 1.5 h mercury trifluoroacetate (2.7 mmol, 1.2 g) was added. Dimethylformamide was added (5 mL). The reaction mixture was heated at 40° C. for 1 h. The reaction mixture was partitioned between ethyl acetate and water. The organic phase was washed with saturated $NaHCO_3$, dried with $Na_2SO_4$, and concentrated in vacuo to afford an oil. The product was isolated by flash chromatography on silica eluting with 15 to 85% EtOAc in hexanes. LC-MS (ESI, Method B): 1.99 min, m/z 408.0 (M+1).

Step E. Methyl 4-[(2-{[4-iodophenyl]imino}-3-methyl-5-propoxy-2,3-dihydro-1H-benzimidazol-1-yl)methyl]benzoate To the title compound of Example 18, Step D (0.66 mmol, 271 mg) in DMF (6 mL) was added NaH (0.73 mmol, 29 mg of a 60% suspension in mineral oil). After 10 min methyl-4-(bromomethyl)benzoate (0.80 mmol, 183 mg) was added and the reaction mixture was stirred at ambient temperature for 10 min. The reaction mixture was partitioned between ethyl acetate and water. The organic phase was washed with saturated $NH_4Cl$ dried with $Na_2SO_4$, and concentrated in vacuo to afford an oil. The product was isolated by flash chromatography on silica eluting with 15 to 60% EtOAc in hexanes.
LC-MS (ESI, Method B): 1.95 min, m/z 558.0 (M+1).

Step F. Methyl 4-[(3-methyl-5-propoxy-2-{[4-(3-thienyl)phenyl]imino}-2,3dihydro-1H-benzimidazol-1-yl)methyl]benzoate To the title compound of Example 18, Step E (100 mg, 0.18 mmol), 3-thienyl boronic acid (25 mg, 0.20 mmol), tri(o-tolyl)phosphine (11 mg, 0.04 mmol), and cesium carbonate (117 mg, 0.36 mmol) in DMF was degassed. Palladium acetate (2.4 mg, 0.01 mmol) was added, and the reaction was stirred overnight at 60° C. The reaction was diluted with ethyl acetate, washed with water and brine, and dried over $Na_2SO_4$. The product was isolated by flash chromatography on silica eluting with 15% EtOAc in hexanes. LC-MS (ESI, Method B): 1.99 min, m/z 512.0 (M+1)

Step G. 4-[(3-Methyl-5-propoxy-2-{[4-(3-thienyl)phenyl]imino}-2,3-dihydro-1H-benzimidazol-1-yl)methyl]benzoic acid To the title compound of Example 18, Step F (0.16 mmol, 80 mg) in dioxane (6 mL) was added a solution of LiOH (2.1 mmol, 50 mg) in $H_2O$ (4 mL). The reaction was stirred at 50° C. for 2.5 h. The product was partitioned between EtOAc and saturated $NH_4Cl$. The organic phase was washed with brine, dried with $Na_2SO_4$, and concentrated under reduced pressure, affording the product as a yellow foamy solid which was taken on directly. LC-MS (ESI, Method B): 1.86 min, m/z 498.0 (M+1)

Step H. 4-[(3-Methyl-5-propoxy-2-{[4-(3-thienyl)phenyl]imino}-2,3-dihydro-1H-benzimidazol-1-yl)methyl]-N-1H-tetrazol-5-ylbenzamide To the title compound of Example 18, Step G (0.18 mmol, 88 mg) was added a solution of 1H-tetraazol-5-amine monohydrate (0.72 mmol, 74 mg), HOBt (0.72 mmol, 110 mg), EDC (0.72 mmol, 138 mg) and DIEA (1.08 mmol, 300 μL) in DMF (4 mL). The reaction mixture was stirred at 40° C. overnight, then concentrated under reduced pressure. The residue was taken up in 4:1 dioxane/$H_2O$, acidified with TFA, and purified by reverse-phase chromatography (20-80% MeCN in $H_2O$, both containing 0.1% TFA). Lyophilization afforded the title compound as a white solid. $H^1$ NMR (500 MHz, $d_6$-DMSO): 8.06 (d, J=6.7 Hz, 2H), 7.88 (m, 1H), 7.75 (d, J=8.5 Hz, 2H), 7.65 (dd, J=3.0, 5.0 Hz, 1H), 7.57 (d, J=4.4 Hz, 1H), 7.50-7.45 (m, 2H), 7.38 (d, J=8.7 Hz, 2H), 7.26 (d, J=8.0 Hz, 1H), 7.05 (m, 1H), 5.55 (s, 2H), 4.04 (t, J=6.6 Hz, 2H), 3.58 (s, 1H), 3.43 (s, 3H), 3.19 (m, 2H), 1.78 (m, 2H), 1.01 (t, J=7.4 Hz, 3H). LC-MS (ESI, Method B): 1.79 min, m/z 565.0 (M+1).

EXAMPLE 19

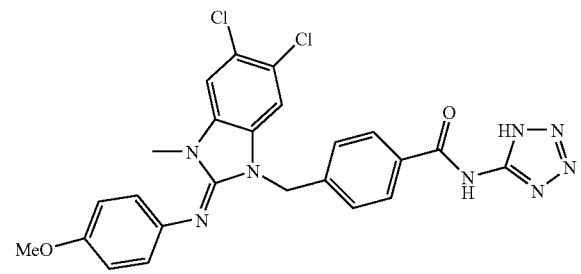

Step A. 5,6-Dichloro-N-[4-(methoxy)phenyl]-1H-benzimidazol-2-amine

To a solution of 4-anisidine (6.5 mmol, 800 mg) and DIEA (7.2 mmol, 1.24 mL) in $CH_2Cl_2$ (10 mL) cooled to 0° C. was added thiophosgene (6.5 mmol, 500 μL) dropwise.

The solution was allowed to reach ambient temperature for 1 h, and 4,5-dichloro-1,2-phenylenediamine (6.5 mmol, 1.15 g) was added to the reaction. The reaction mixture was heated at 40° C. for 16 h, and MeI (7.2 mmol, 445 µL) and DIEA (7.2 mmol, 1.24 µL) were added. The reaction was heated at 40° C. for 8 h, and allowed to stand at ambient temperature for 16 h. Aqueous workup with CH$_2$Cl$_2$/brine, followed by flash chromatography on silica eluting with 4% MeOH in CH$_2$Cl$_2$ afforded the product as a brown oil. LC-MS (ESI, Method B): 1.62 min, m/z 308.2 (M+1).

Step B. Methyl 4-[(5,6-dichloro-2-{[4-(methoxy)-phenyl]amino}-1H-benzimidazol-1-yl)methyl]benzoate To the title compound of Example 19, Step A (1.3 mmol, 407 mg) in DMF (5 mL) was added NaH (1.6 mmol, 62 mg of 60% suspension in mineral oil). After 10 min methyl-4-(bromomethyl)benzoate (1.3 mmol, 304 mg) was added and the reaction mixture was allowed to stand at ambient temperature for 2 h. Aqueous workup with CH$_2$Cl$_2$/saturated NaHCO$_3$ and brine, followed by flash chromatography on silica eluting with 40%, 50% and 60% EtOAc in hexanes afforded the product as a tan solid. LC-MS (ESI, Method B): 1.93 min, m/z 456.1 (M+1).

Step C. Methyl 4-[(5,6-dichloro-2-{[4-(methoxy)-phenyl]imino}-3-methyl-2,3-dihydro-1H-benzimidazol-1-yl)methyl]benzoate To a solution of the title compound of Example 19, Step B (0.45 mmol, 203 mg) in DMF (3 mL) was added NaH (0.54 mmol, 21 mg of 60% suspension in mineral oil). After 10 min MeI (0.9 mmol, 56 µL) was added and the reaction was allowed to stand at ambient temperature for 2 h. Aqueous workup with CH$_2$Cl$_2$/saturated NaHCO$_3$, followed by flash chromatography on silica eluting with 30% and 40% EtOAc in hexanes, afforded the product as a white solid. LC-MS (ESI, Method B): 1.93 min. m/z 470.2 (M+1).

Step D. Methyl 4-[(5,6-dichloro-2-{[4-(methoxy)-phenyl]imino}-3-methyl-2,3-dihydro-1H-benzimidazol-1-yl)methyl]-N-1H-tetrazol-5-ylbenzamide To the title compound of Example 19, Step C (0.02 mmol, 8 mg) dissolved in dioxane (0.8 mL) was added a solution of LiOH (0.42 mmol, 10 mg) in H$_2$O (0.4 mL). The reaction was stirred at 40° C. for 1 h. The product was partitioned between EtOAc and pH 7 buffer. The organic phase was dried with MgSO$_4$ and concentrated under reduced pressure to afford a foam. To the solid was added a solution of 1H-tetraazol-5-amine monohydrate (0.1 mmol, 10 mg), HOBt (0.06 mmol, 9 mg), EDC (0.06 mmol, 11 mg) and DIEA (0.1 mmol, 16 µL) in DMF (0.5 mL). The reaction mixture was heated to 40° C. for 2 h, then concentrated under reduced pressure. Purification by reverse-phase chromatography (10-80% MeCN/H$_2$O, both containing 0.1% TFA) and lyophilization afforded the title compound as a white solid. $^1$H NMR (d$_6$-DMSO+NEt$_3$, 500 MHz) δ 7.91 (broad d, J=7.8 Hz, 2H), 7.34 (s, 1H), 7.30-7.27 (overlapping s, d, 3H), 6.76 (overlapping m, 4H), 5.08 (s, 2H), 3.71 (s, 3H), 3.11 (s, 3H). LC-MS (ESI, Method A): 2.59 min, m/z 523.1 (M+1).

EXAMPLE 20

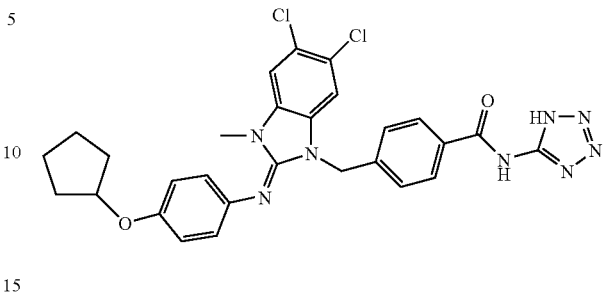

Step A. Methyl 4-[(5,6-dichloro-2-{[4-(hydroxy)-phenyl]imino}-3-methyl-2,3-dihydro-1H-benzimidazol-1-yl)methyl]benzoate To the title compound of Example 19 Step C (0.11 mmol, 50 mg) in CH$_2$Cl$_2$ (0.5 mL) cooled to −78° C. was added dropwise BBr$_3$ (0.33 mol, 330 µL of a 1 M solution in CH$_2$Cl$_2$). After addition, the reaction was removed from the cold bath for 30 min, then cooled to −78° C. and diluted with MeOH. The mixture was concentrated under reduced pressure and the product was isolated by chromatography on silica eluting with 4% MeOH in CH$_2$Cl$_2$ as a white solid. LC-MS (ESI, Method B): 1.80 min, m/z 456.1 (M+1).

Step B. Methyl 4-[(5,6-dichloro-2-{[4-(cyclopentyloxy)-phenyl]imino}-3-methyl-2,3-dihydro-1H-benzimidazol-1-yl)methyl]benzoate To the title compound of Example 20, Step A (0.03 mmol, 14 mg) in CH$_2$Cl$_2$ (0.6 mL) was added cyclopentanol (0.08 mmol, 7 µL), DIAD (0.06 mmol, 12 µL) and Ph$_3$P (0.06 mmol, 16 mg). The reaction was allowed to stand at ambient temperature for 16 h, then purified by chromatography on silica eluting with 10% and 25% EtOAc in hexanes to afford the product as a white solid. LC-MS (ESI, Method B): 2.12 min, m/z 524.2 (M+1).

Step C. Methyl 4-[(5,6-dichloro-2-{[4-(cyclopentyloxy)-phenyl]imino}-3-methyl-2,3-dihydro-1H-benzimidazol-1-yl)methyl]-N-1H-tetrazol-5-ylbenzamide To the title compound of Example 20, Step B (0.03 mmol, 15 mg) dissolved in dioxane (0.8 mL) was added a solution of LiOH (0.42 mmol, 10 mg) in H$_2$O (0.4 mL). The reaction was stirred at 40° C. for 1 h, then partitioned between EtOAc and pH 7 buffer. The organic phase was dried with MgSO$_4$ and concentrated under reduced pressure. To the residue was added a solution of 1H-tetraazol-5-amine monohydrate (0.1 mmol, 10 mg), HOBt (0.06 mmol, 9 mg), EDC (0.06 mmol, 11 mg) and DIEA (0.1 mmol, 16 µL) in DMF (0.5 mL). The reaction mixture was heated to 40° C. for 2 h, then concentrated under reduced pressure. Purification by reverse-phase chromatography (20-60% MeCN in H$_2$O, both containing 0.1% TFA) and lyophilization afforded the title compound as a white solid. $^1$H NMR (d$_6$-DMSO+NEt$_3$, 500 MHz) δ 7.89 (broad d, J=6.9 Hz, 2H), δ 7.33 (s, 1H), 7.27-7.25 (overlapping s, d, 3H), 6.73 (apparent s, 4H), 5.07 (s, 2H), 4.72 (br m, 1H), 3.12 (s, 3H), 1.86 (br m, 2H), 1.10 (br m, 2H), 1.58 (br m, 2H), δ 1.19 (br m, 2H). LC-MS (ESI, Method A): 3.13 min, m/z 577.3 (M+1).

EXAMPLE 21

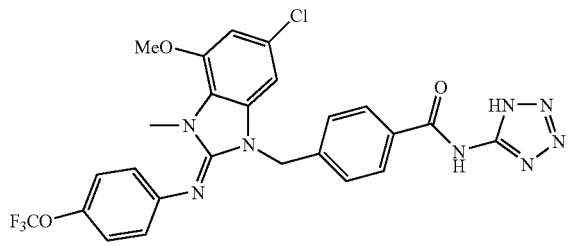

Step A. 2-Methoxy-6-nitroaniline

To acetone (60 mL) charged with 2-amino-3-nitrophenol (32 mmol, 4.9 g) and $K_2CO_3$ (48 mmol, 6.62 g) was added MeI (32 mmol, 1.98 mL). The reaction mixture was stirred rapidly at ambient temperature for 16 h. Acetone was removed under reduced pressure and the residue was partitioned between $CH_2Cl_2$ and brine. The organic phase was dried over $MgSO_4$ and concentrated under reduced pressure to provide the product as a brown solid. LC-MS (ESI, Method C) 2.56 min, m/z 169.1 (M+1).

Step B. 4-Chloro-2-methoxy-6-nitroaniline

To a solution of the title compound of Example 21, Step A (26.6 mmol, 4.5 g) in MeCN (30 mL) at 60° C. was added N-chlorosuccinimide (29 mmol, 3.9 g). The solution was brought to reflux for 2 h and allowed to stand at ambient temperature for 16 h. The reaction mixture was partitioned between $CH_2Cl_2$ and saturated $NaHCO_3$. The organic phase was washed with brine, dried with $Na_2SO_4$, and concentrated in vacuo to afford the product as a brown solid. LC-MS (ESI, Method B): 2.14 min, m/z 203.11 (M+1).

Step C. 4-Chloro-2-methoxy-N-methyl-6-nitroaniline

To the title compound of Example 21, Step B (19.9 mmol, 4.03 g) in DMF (50 mL) at 0° C. was added portionwise NaH (31.8 mmol, 1.27 g of 60% suspension in mineral oil) (exothermic, gas evolution). After 10 min MeI (23 mmol, 1.5 mL) was added and the reaction was allowed to stand at ambient temperature for 3 h. Saturated $NaHCO_3$ and brine were added to the reaction resulting in formation of a precipitate, which was filtered, washed with water and dried in vacuo. Flash chromatography on silica eluting with 15% EtOAc in hexanes afforded the product as a bright red solid. LC-MS (ESI, Method B): 2.31 min, m/z 217.2 (M+1).

Step D. 5-Chloro-3-methoxy-$N^2$-methylbenzene-1,2-diamine

To the title compound in Example 21, Step C (2.3 mmol, 500 mg) in 10% $H_2O$ in DMF (15 naL) was added $SnCl_2.2H_2O$ (9.3 mmol, 2.08 g). The reaction mixture was stirred at 45° C. for 4 h. The reaction mixture was poured into EtOAc and saturated $NaHCO_3$, and the mixture was stirred, affording a yellowish precipitate. The resulting slurry was filtered through celite and the filter cake was washed with water and EtOAc. The organic phase was collected, dried over $Na_2SO_4$ and concentrated in vacuo.

Flash chromatography on silica eluting with 0-7% MeOH in $CH_2Cl_2$ provided the product as a brown oil. $^1$H NMR (500 MHz, $d_6$-DMSO) δ 6.34 (d, J=2.0 Hz, 1H), 6.25 (d, J=2.3 Hz, 1H), 4.93 (s, 2H), 3.73 (s, 3H), 3.51 (br m, 1H), 2.51 (s, 3H). LC-MS (ESI, Method B): 1.27 min, m/z 187.2 (M+1).

Step E. 5-Chloro-7-methoxy-1-methyl-N-[4-(trifluoromethoxy)phenyl]-1H-benzimidazol-2-amine A solution of the title compound of Example 21, Step D (0.81 mmol, 151 mg) and 4-trifluoromethoxyphenyl isothiocyanate (0.81 mmol, 132 µL) in $CH_2Cl_2$ (1 mL) was heated at 45° C. for 2.5 h. The reaction was allowed to cool to ambient temperature and $Hg(O_2CCF_3)_2$ (0.97 mmol, 414 mg), then DMF (1 mL) were added. The reaction mixture was heated at 45° C. for 16 h. $CH_2Cl_2$ and brine containing $Na_2S$ were added, and the resulting slurry was filtered through celite. The organic phase was collected, dried with $MgSO_4$ and concentrated in vacuo. Flash chromatography on silica eluting with 25% to 40% EtOAc in hexanes afforded the product as a beige solid. $^1$H NMR (500 MHz, $d_6$-DMSO) δ 9.11 (s, 1H), 7.91 (d, J=9.2 Hz, 2H), 7.33 (d, J=9.0 Hz, 2H), 7.06 (m, 1H), 6.73 (m, 1H), 3.92 (s, 3H), 3.90 (s, 3H). LC-MS (ESI, Method B): 1.98 min, m/z 372.1 (M+1).

Step F. Methyl 4-[(6-chloro-4-methoxy-3-methyl-2-{[4-(trifluoromethoxy)phenyl]-imino}-2,3-dihydro-1H-benzimidazol-1-yl)methyl]-N-1H-tetrazol-5-ylbenzoate A solution of the title compound of Example 21, Step E (0.4 mmol, 155 mg) and methyl-4-(bromomethyl)benzoate (1.6 mmol, 383 mg) in MeCN (2 mL) was heated to 80° C. for 40 h. The reaction was concentrated in vacuo and purified by flash chromatography on silica eluting with $CH_2Cl_2$, then 2% MeOH in $CH_2Cl_2$, affording the product as an oil. $^1$H NMR (500 MHz, $d_6$-DMSO) δ 7.9 (d, J=8.2 Hz, 2H), 7.28 (d, J=8.2Hz, 2H), 7.10 (d, J=8.7 Hz, 2H), 6.87 (d, J=1.8 Hz, 1H), 6.81-6.86 (overlapping m, 3H), 5.12 (s, 2H), 3.88 (s, 3H), 3.84 (s, 3H). LC-MS (ESI, Method A): 3.19 min, m/z 520.1 (M+1).

Step G. 4-[(6-Chloro-4-methoxy-3-methyl-2-{[4-(trifluoromethoxy)phenyl]-imino}-2,3-dihydro-1H-benzimidazol-1-yl)methyl]-N-1H-tetrazol-5-ylbenzamide To the title compound of Example 21, Step F (110 mg, 0.21 mmol) dissolved in dioxane (1 mL) was added a solution of LiOH (25 mg, 1.1 mmol) in $H_2O$ (0.5 mL). The reaction was stirred at 40° C. for 1 h, then partitioned between EtOAc and pH 7 phosphate buffer. The organic phase was dried with $MgSO_4$ and concentrated under reduced pressure. To the residue was added a solution of 1H-tetraazol-5-amine monohydrate (66 mg, 0.64 mmol), HOBt (65 mg, 0.42 mmol), EDC (81 mg, 0.42 mmol) and DIEA (111 µL, 0.64 mmol) in DMF (0.5 mL). The reaction mixture was heated to 40° C. for 2 h, then concentrated under reduced pressure. Reverse-phase chromatography (20-60% MeCN/$H_2O$, both containing 0.1% TFA) and lyophilization afforded the title compound as a white solid. $^1$H NMR (500 MHz, $d_6$-DMSO) δ 12.40 (s, 1H), 8.01 (d, J=8.5 Hz, 2H), 7.34 (d, J=8.5 Hz, 2H), 7.36-6.55 (m, 7H), 5.44 (s, 2H), 3.97 (s, 3H), N-Me obscured by $H_2O$; LCMS (ESI, Method B) 1.66 min, m/z 573.1 (M+1).

EXAMPLE 22

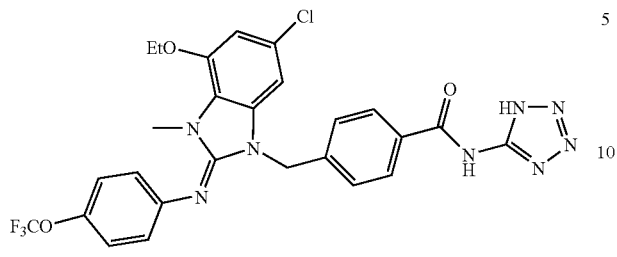

Step A. Methyl 4-[(6-chloro-4-hydroxy-3-methyl-2-{[4-(trifluoromethoxy)phenyl]-imino}-2,3-dihydro-1H-benzimidazol-1-yl)methyl]-N-1H-tetrazol-5-ylbenzoate To a stirring solution of the title compound of Example 21, Step F (0.12 mmol, 60 mg) in CH$_2$Cl$_2$ (0.6 mL) at −78° C. was added dropwise BBr$_3$ (0.58 mmol, 580 µL of a 1 M solution in CH$_2$Cl$_2$). The reaction was removed from the cold bath for 1.5 h, then cooled to −78° C. and quenched by addition of MeOH. The reaction was concentrated in vacuo and purified by flash chromatography on silica eluting with 5% MeOH in CH$_2$Cl$_2$ to afford the product as a white solid. LC-MS (ESI, Method B): 2.14 min, m/z 506.2 (M+1).

Step B. Methyl 4-[(6-chloro-4-ethoxy-3-methyl-2-{[4-(trifluoromethoxy)phenyl]-imino}-2,3-dihydro-1H-benzimidazol-1-yl)methyl]-N-1H-tetrazol-5-ylbenzoate To the title compound of Example 22, Step A (0.03 mmol, 13 mg) in CH$_2$Cl$_2$ (0.6 mL) was added EtOH (0.06 mmol, 6 µL), DIAD (0.06 mmol, 12 µL) and Ph$_3$P (0.05 mmol, 13 mg). The reaction mixture was allowed to stand at ambient temperature for 4 h, then purified on silica eluting with 10% and 25% EtOAc in hexanes to provide the product as a white solid. LC-MS (ESI, Method A): 3.32 min, m/z 534.1 (M+1).

Step C. 4-[(6-Chloro-4-ethoxy-3-methyl-2-{[4-(trifluoromethoxy)phenyl]-imino}-2,3-dihydro-1H-benzimidazol-1-yl)methyl]-N-1H-tetrazol-5-ylbenzamide To the title compound of Example 22, Step B (0.03 mmol, 13 mg) dissolved in dioxane (1 mL) was added a solution of LiOH (0.4 mmol, 10 mg) in H$_2$O (0.5 mL). The reaction mixture was stirred at 40° C. for 1 h, then partitioned between EtOAc and pH 7 buffer. The organic phase was dried with MgSO$_4$ and concentrated under reduced pressure. To the residue was added a solution of 1H-tetraazol-5-amine monohydrate (0.1 mmol, 10 mg), HOBt (0.06 mmol, 9 mg), EDC (0.06 mmol, 11 mg) and DIEA (0.1 mmol, 16 µL) in DMF (0.5 mL). The solution was heated to 40° C. for 2 h, then concentrated under reduced pressure. Purification by reverse-phase chromatography (20-60% MeCN in H$_2$O, both containing 0.1% TFA) and lyophilization afforded the title compound as a white solid. $^1$H NMR (d$_6$-DMSO+NEt$_3$, 500 MHz) δ 7.89 (broad d, J=6.5 Hz, 2H), 7.25 (d, J=8.2 Hz, 2H), 7.12 (d, J=8.3 Hz, 2H), 6.88-6.86 (overlapping s, m, 3H), 6.80 (s, 1H), 5.11 (s, 2H), 4.14 (q, J=6.9 Hz, 2H), 1.36 (t, J=6.9 Hz, 3H), N-Me obscured by H$_2$O peak. LC-MS (ESI, Method A): 2.95 min, m/z 587.0 (M+1).

Following the procedures outlined for Examples 1-22 the compounds listed in Tables 1-4 were prepared

TABLE 1

| Example | R$^1$ | R$^2$ | LCMS data; retention time (min)/M + H | Prepared according to example no. |
|---|---|---|---|---|
| 23 | H | 3,5-diCl | Method A 2.59 min/493.0 (M + 1) | Ex 4 |
| 24 | 6-MeO | 3,5-diCl | Method A 2.68 min/523.1 (M + 1) | Ex 4 |
| 25 | H | 4-(1'-cyclohexenyl) | Method C 2.74 min/505.2 (M + 1) | Ex 4 |
| 26 | 6-CF$_3$O | 4-CF$_3$O | Method C 2.72 min/593.1 (M + 1) | Ex 4 |
| 27 | 6-CF$_3$ | 4-CF$_3$O | Method C 2.79 min/577.1 (M + 1) | Ex 5 |
| 28 | 4,6-diCl | 4-CF$_3$O | Method A 2.88 min/577.1 (M + 1) | Ex 5 |
| 29 | 6-CF$_3$ | 4-Cl | Method C 2.56 min/527.2 (M + 1) | Ex 12 |
| 30 | 6-PrO | 4-CF$_3$O | Method C 2.66 min/567.2 (M + 1) | Ex 5 |
| 31 | 6-CF$_3$ | 3-CF$_3$ | Method C 2.94 min/561.2 (M + 1) | Ex 13 |
| 32 | 6-CF$_3$ | 4-CF$_3$ | Method C 3.01 min/561.2 (M + 1) | Ex 13 |
| 33 | 4-Cl, 6-CF$_3$ | 4-CF$_3$O | Method C 3.56 min/611.2 (M + 1) | Ex 7 |
| 34 | 5,6-diCl | 4-cPentCH$_2$O | Method A 3.23 min/591.3 (M + 1) | Ex 20 |
| 35 | 5,6-diCl | 4-$^i$PrO | Method A 2.99 min/551.2 (M + 1) | Ex 20 |

TABLE 1-continued

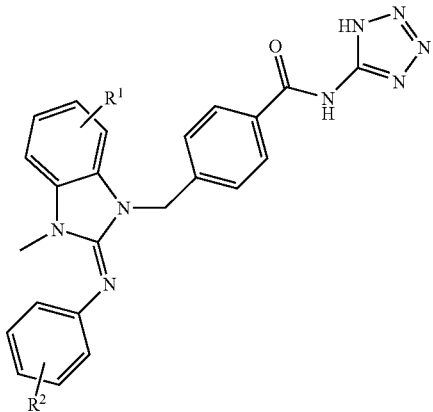

| Example | R¹ | R² | LCMS data; retention time (min)/M + H | Prepared according to example no. |
|---|---|---|---|---|
| 36 | 5,6-diCl | 4-BnO | Method A 2.90 min/599.1 (M + 1) | Ex 20 |
| 37 | 5,6-diCl | 4-$^t$Bu | Method C 2.87 min/549.2 (M + 1) | Ex 13 |
| 38 | 5,6-diCl | 4-$CF_3$ | Method C 3.14 min/561.2 (M + 1) | Ex 13 |
| 39 | 6-MeO | 4-(3',3',5',5'-tetramethylcyclohexyl) | Method B 3.2 min./593.4 (M + 1) | Ex 4 |
| 40 | 6-MeO | 4-(4',4'-difluorocyclohexyl) | Method B 1.86 min/573.3 (M + 1) | Ex 4 |
| 41 | 5-PrO | 4-$CF_3CH_2$O | Method A 3.07 min/581.1 (M + 1) | Ex 6 |
| 42 | 4-BuO, 6-Cl | 4-$CF_3$O | Method A 3.32 min/615.0 (M + 1) | Ex 22 |
| 43 | 5,6-diCl | 3,4-diCl | Method B 1.92 min/562.9 (M + 3) | Ex 13 |
| 44 | 4,6-di$CF_3$ | 4-$CF_3$O | Method A 3.94 min/615.0 (M + 1) | Ex 7 |
| 45 | 6-$CF_3$ | 4-(3',3',5',5'-tetramethylcyclohexyl) | Method C 3.59 min/631.4 (M + 1) | Ex 4 |
| 46 | 6-MeO | 4-(1'-adamantyl) | Method C 3.19 min/589.4 (M + 1) | Ex 4 |
| 47 | 4-MeO, 6-Cl | 4-cyclohexyl | Method C 3.09 min/571.3 (M + 1) | Ex 4 |
| 48 | 5-PrO | 4-$CF_2HCH_2$ | Method B 2.08 min/547 (M + 1) | Ex 6 |
| 49 | 6-$CF_3$ | 4-Bu | Method B 2.08 min/549.4 (M + 1) | Ex 6 |
| 50 | 4-Et, 6-$CF_3$ | 4-$^t$Bu | Method A 3.11 min/577.2 (M + 1) | Ex 21 |
| 51 | 4-Et, 6-$CF_3$ | 4-F | Method A 2.78/539.1 (M + 1) | Ex 21 |
| 52 | 4-PrO, 6-Cl | 4-$CF_3$O | Method A 3.07 min/601.03 (M + 1) | Ex 22 |

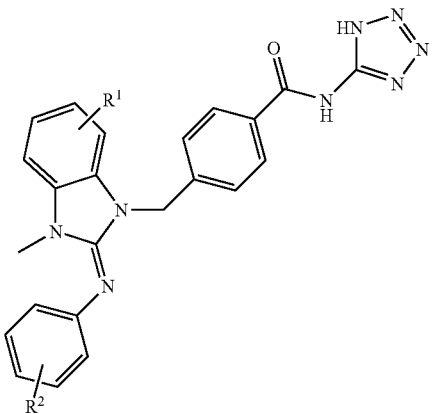

| Example | R¹ | R² | LCMS data; retention time (min)/M + H | Prepared according to example no. |
|---|---|---|---|---|
| 53 | 4-$^i$PrO, 6-Cl | 4-$CF_3$O | Method A 3.04 min/601.0 (M + 1) | Ex 22 |
| 54 | 4-Ph, 6-$CF_3$ | 4-$CF_3$O | Method A 3.17 min/653.3 (M + 1) | Ex 7 |
| 55 | 4-MeO, 6-Cl | tBu | Method A 2.99 min/545.2 (M + 1) | Ex 21 |
| 56 | 6-$CF_3$ | 4-(3',5'-dimethylcyclopentyl) | Method C 3.46 min/589.4 (M + 1) | Ex 6 |
| 57 | 6-MeO | 4-(3',5'-dimethylcyclopentyl) | Method C 3.30 min/551.4 (M + 1) | Ex 4 |
| 58 | 4-Et, 6-$CF_3$ | 4-Me | Method A 2.88 min/535.3 (M + 1) | Ex 21 |
| 59 | 4-Et, 6-$CF_3$ | 4-$^i$Pr | Method A 3.04 min/563.3 (M + 1) | Ex 21 |
| 60 | 4-BuO, 6-$CF_3$ | 4-$CF_3$O | Method A 3.26 min/649.0 (M + 1) | Ex 21 |
| 61 | 6-F | 4-cyclohexyl | Method C 3.53 min/525.3 (M + 1) | Ex 6 |
| 62 | 4-MeO, 6-Cl | 3-Cl, 4-$CF_3$O | Method A 2.91 min/606.9 (M + 1) | Ex 21 |
| 63 | 4-OH, 6-Cl | 4-$CF_3$O | Method A 2.70 min/559.0 (M + 1) | Ex 22 |
| 64 | 4-MeO, 6-$CF_3$ | 4-$CF_3$O | Method C 3.14 min/607.3 (M + 1) | Ex 21 |
| 65 | 4-PrO, 6-$CF_3$ | 4-$CF_3$O | Method C 3.71 min/657.2 (M + 1) | Ex 21 |
| 66 | 6-MeO | 3-Me, 4-$^i$Pr | Method C 2.99 min/511.3 (M + 1) | Ex 6 |
| 67 | 6-$CF_3$ | 3-Me, 4-$^i$Pr | Method C 3.17 min/549.3 (M + 1) | Ex 6 |
| 68 | 4-MeO, 6-$CF_3$ | 4-$^t$Bu | Method B 2.04 min/579.2 (M + 1) | Ex 21 |
| 69 | 4-PrO, 6-$CF_3$ | 4-$^t$Bu | Method B 2.22 min/607.3 (M + 1) | Ex 21 |

TABLE 1-continued

[Structure: benzimidazole with R1, N-methyl, =N-phenyl(R2), CH2-phenyl-C(O)NH-tetrazole]

| Example | R¹ | R² | LCMS data; retention time (min)/M + H | Prepared according to example no. |
|---|---|---|---|---|
| 70 | 4-PrO | 4-CF₃O | Method A 2.99 min/567.0 (M + 1) | Ex 21 |
| 71 | 4-EtO, 6-CF₃ | 4-CF₃O | Method A 3.00 min/621.0 (M + 1) | Ex 21 |

TABLE 2

[Structure: benzimidazole with R1, N-methyl, =N-phenyl(R2), CH2-phenyl-C(O)NH-CH2CH2-COOH]

| Example | R¹ | R² | LCMS data: retention time (min)/M + H | Prepared according to example no. |
|---|---|---|---|---|
| 72 | 6-MeO | 3,5-diCl | Method A 2.61 min/527.2 (M + 1) | Ex 4 |
| 73 | 5-Cl | 4-CF₃O | Method C 2.48 min/547.1 (M + 1) | Ex 12 |
| 74 | 5,6-diCl | 4-cyclo-hexyl | Method C 2.86 min/579.2 (M + 1) | Ex 4 |
| 75 | 6-CF₃ | 4-Cl | Method C 2.50 min/531.1 (M + 1) | Ex 13 |
| 76 | 6-CF₃ | 3-CF₃ | Method C 2.78 min/565.2 (M + 1) | Ex 13 |
| 77 | 6-CF₃ | 4-CF₃ | Method C 2.85 min/565.2 (M + 1) | Ex 13 |

TABLE 2-continued

| Example | R¹ | R² | LCMS data: retention time (min)/M + H | Prepared according to example no. |
|---|---|---|---|---|
| 78 | 4-PrO | 4-CF₃O | Method A 2.84 min/571.1 (M + 1) | Ex 21 |

TABLE 3

[Structure: 5,6-dichlorobenzimidazole with N-R, =N-(4-CF3O-phenyl), CH2-phenyl-C(O)NH-tetrazole]

| Example | R | LCMS data: retention time (min)/M + H | Prepared according to example no. |
|---|---|---|---|
| 79 | Et | Method A 2.88 min/591.1 (M + 1) | Ex 3 |
| 80 | Pr | Method A 3.24 min/605.1 (M + 1) | Ex 3 |
| 81 | Bn | Method A 3.34 min/652.9 (M + 1) | Ex 3 |
| 82 | ⁱPr | Method A 2.92 min/605.1 (M + 1) | Ex 3 |
| 83 | FCH₂CH₂ | Method A 2.86 min/608.9 (M + 1) | Ex 3 |
| 84 | Me₂NCH₂CH₂ | Method A 2.74 min/634.3 (M + 1) | Ex 3 |
| 85 | MeOCH₂CH₂ | Method A 2.94 min/621.0 (M + 1) | Ex 7 |
| 86 | MeOCH₂CH₂CH₂ | Method A 2.95 min/634.9 (M + 1) | Ex 7 |
| 87 | Me₂NCH₂CH₂CH₂ | Method A 2.46 min/647.9 (M + 1) | Ex 7 |

TABLE 4

| Example | R² | LCMS data: retention time (min)/M + H | Prepared according to example no. |
| --- | --- | --- | --- |
| 88 | (structure) | Method A 2.66 min/647.9 (M + 1) | Ex 3 |
| 89 | (structure) | Method C 2.99 min/591.3 (M + 1) | Ex 13 |
| 90 | (structure) | Method C 3.75 min/673.1 (M + 1) | Ex 3 |

TABLE 4-continued

| Example | R² | LCMS data: retention time (min)/M + H | Prepared according to example no. |
|---|---|---|---|
| 91 | | Method C 2.67 min/533.2 (M + 1) | Ex 13 |
| 92 | | Method A 2.96 min/561.3 (M + 1) | Ex 21 |
| 93 | | Method A 3.00 min/605.3 (M + 1) | Ex 21 |

TABLE 4-continued

| Example | R² | LCMS data: retention time (min)/M + H | Prepared according to example no. |
|---|---|---|---|
| 94 | [structure: benzimidazole with CF₃, ethyl, N-ethyl, N=phenyl-tBu, CH₂-phenyl-C(O)NH-tetrazole] | Method A 3.10 min/577.7 (M + 1) | Ex 21 |
| 95 | [structure: benzimidazole with Cl, PrO, N-ethyl, N=phenyl-OCF₃, CH₂-phenyl-C(O)NH-tetrazole] | Method A 3.12 min/615.0 (M + 1) | Ex 21 |

Biological Assays

The ability of the compounds of the present invention to inhibit the binding of glucagon and their utility in treating or preventing type 2 diabetes mellitus and the related conditions can be demonstrated by the following in vitro assays.

Glucagon Receptor Binding Assay

A stable CHO (Chinese hamster ovary) cell line expressing cloned human glucagon receptor was maintained as described (Chicchi et al. *J Biol Chem* 272, 7765-9 (1997); Cascieri et al. *J Biol Chem* 274, 8694-7 (1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM MgCl$_2$, 2 mM EDTA, 12% Glycerol, and 0.200 mg WGA coated PVT SPA beads (Amersham), +/−compounds or 0.001 mM unlabeled glucagon. After 4-12 hours incubation at room temperature, the radioactivity bound to the cell membranes was determined in a radioactive emission detection counter (Wallac-Microbeta). Data was analyzed using the software program Prism® from GraphPad. The IC$_{50}$ were calculated using non-linear regression analysis assuming single site competition.

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was setup as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in presence of compounds or DMSO controls for 30 minutes, and then stimulated with glucagon (250 pM) for an additional 30 minutes. The cell stimulation was stopped by addition of equal amount of a detection buffer containing lysis buffer as well as $^{125}$I-labeled cAMP tracer (NEN). After 3 hours of incubation at room temperature the bound radioactivity was determined in a liquid scintillation counter (TopCount-Packard Instruments). Basal activity (100% inhibition) was determined using the DMSO control while 0% inhibition was defined at the amount of pmol cAMP produced by 250 pM glucagon.

Certain embodiments of the invention has been described in detail; however, numerous other embodiments are contemplated as falling within the invention. Thus, the claims are not limited to the specific embodiments described herein.

All patents, patent applications and publications that are cited herein are hereby incorporated by reference in their entirety.

What is claimed is:

1. A compound represented by formula I:

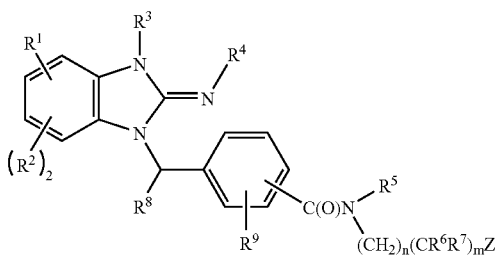

or a pharmaceutically acceptable salt or solvate thereof, wherein:

$R^1$ represents H or is independently selected from the group consisting of:
  a) OH, halo, $CO_2R^a$, $C(O)NR^bR^c$, $NR^bR^c$, CN or $S(O)_pR^d$;
  b) $C_{1-10}$alkyl, $C_{2-10}$alkenyl, $C_{2-10}$alkynyl, $OC_{1-10}$alkyl, $OC_{3-10}$alkenyl and $OC_{3-10}$alkynyl, said groups being optionally substituted with:
    (1) 1-5 halo groups up to a perhaloalkyl group;
    (2) 1 oxo group;
    (3) 1-2 OH groups;
    (4) 1-2 $C_{1-10}$alkoxy groups, each optionally substituted with: up to five halo or a perhaloalkoxy, 1 OH or $CO_2R^a$ group;
    (5) 1 $CO_2R^a$ or $S(O)_pR^d$;
    (6) 1-2 Aryl, Hetcy or HAR groups, each optionally substituted as follows:
      (a) 1-5 halo groups,
      (b) 1 OH, $CO_2R^a$, CN, $S(O)_pR^d$, $NO_2$ or $C(O)NR^bR^c$,
      (c) 1-2 $C_{1-10}$alkyl or alkoxy groups, each optionally substituted with: 1-5 halo, up to perhaloalkyl, and 1-2 OH or $CO_2R^a$ groups; and
      (d) 1-2 phenyl rings, each of which is optionally substituted as follows: 1-5 halo groups up to perhalo, 1-3 $C_{1-10}$alkyl or alkoxy groups, each being further optionally substituted with 1-5 halo up to perhalo, or 1-2 hydroxy or $CO_2R^a$ groups;
  c) Aryl, HAR, Hetcy, —O-Aryl, —O-HAR and —O-Hetcy, each optionally substituted as set forth below:
    (1) 1-3 $C_{1-10}$alkyl, $C_{2-10}$alkenyl or $C_{2-10}$alkynyl groups optionally substituted with 1-5 halo groups; 1-2 OH groups; phenyl optionally substituted with 1-3 halo, $C_{1-6}$alkyl or $C_{1-6}$alkoxy groups, the alkyl and alkoxy groups being further optionally substituted with 1-3 halo groups; $CO_2R^a$; CN or $S(O)_pR^d$ groups; and
    (2) 1-3 $C_{1-10}$alkoxy groups, the alkyl portion of which is optionally substituted with 1-5 halo groups, 1-2 OH; phenyl optionally substituted with 1-3 halo, $C_{1-6}$alkyl or $C_{1-6}$alkoxy groups, the alkyl and alkoxy groups being further optionally substituted with 1-3 halo groups; $CO_2R^a$; CN or $S(O)_pR^d$ groups;
said Aryl, HAR, Hetcy —O-Aryl, —O-HAR and —O-Hetcy group c) being further optionally substituted on carbon by a group selected from the group consisting of;
    (3) 1-5 halo groups;
    (4) 1-2 OH groups;
    (5) 1 $S(O)_pR^d$, $NO_2$ or CN group;
    (6) 1-2 $CO_2R^a$;
    (7) —$C(O)NR^bR^c$;

each $R^2$ represents H or is independently selected from the group consisting of:
  a) OH, halo, $CO_2R^a$, $C(O)NR^bR^c$, $NR^bR^c$, CN or $S(O)_pR^d$;
  b) $C_{1-10}$alkyl, $C_{2-10}$alkenyl, $C_{2-10}$alkynyl, $OC_{1-10}$alkyl, $OC_{3-10}$alkenyl and $OC_{3-10}$alkynyl, said groups being optionally substituted with:
    (1) 1-5 halo groups up to a perhaloalkyl group;
    (2) 1 oxo group;
    (3) 1 OH group;
    (4) 1 $C_{1-10}$alkoxy group, each optionally substituted with: up to five halo or a perhaloalkoxy, 1 OH or $CO_2R^a$ group;
    (5) 1 $CO_2R^a$ or $S(O)_pR^d$;
    (6) 1 Aryl, Hetcy or HAR group, each optionally substituted as follows:
      (a) 1-5 halo groups,
      (b) 1 OH, $CO_2R^a$, CN, $S(O)_pR^d$, $NO_2$ or $C(O)NR^bR^c$,
      (c) 1-2 $C_{1-10}$alkyl or alkoxy groups, each optionally substituted with: 1-5 halo, up to perhaloalkyl, and 1-2 OH or $CO_2R^a$ groups; and
      (d) 1-2 phenyl rings, each of which is optionally substituted as follows: 1-5 halo groups up to perhalo; 1-3 $C_{1-10}$alkyl or alkoxy groups, each being further optionally substituted with 1-5 halo up to perhalo; and 1-2 hydroxy or $CO_2R^a$ groups;
  c) Aryl, HAR, Hetcy, —O-Aryl, —O-HAR and —O-Hetcy, each optionally substituted as set forth below:
    (1) 1-3 $C_{1-10}$alkyl, $C_{2-10}$alkenyl or $C_{2-10}$alkynyl groups optionally substituted with 1-5 halo groups, 1-2 OH, phenyl, $CO_2R^a$, CN or $S(O)_pR^d$ groups;
    (2) 1-3 $C_{1-10}$alkoxy groups, the alkyl portion of which is optionally substituted with 1-5 halo groups, 1-2 OH, phenyl, $CO_2R^a$, CN or $S(O)_pR^d$ groups;
said Aryl, HAR or Hetcy group c) being further optionally substituted on carbon by a group selected from the group consisting of;
    (3) 1-5 halo groups up to perhalo;
    (4) 1 OH group;
    (5) 1 $S(O)_pR^d$, $NO_2$ or CN group;
    (6) 1 $CO_2R^a$;

$R^3$ selected from the group consisting of:
  a) $C_{1-10}$alkyl or $C_{2-10}$alkenyl, each optionally substituted with
    1-5 halo groups up to perhalo;
    1-2 OH, $C_{1-3}$alkoxy or halo$C_{1-3}$alkoxy groups;
    1-2 $NR^cR^d$ groups; and
    1-2 Aryl, HAR or Hetcy groups, each optionally substituted with 1-3 halo groups and 1-2 groups selected from CN, $NO_2$, $C_{1-3}$alkyl, halo$C_{1-3}$alkyl, $C_{1-3}$alkoxy and halo$C_{1-3}$ alkoxy groups,
  b) Aryl, HAR or Hetcy, each optionally substituted with 1-3 halo groups and 1-2 groups selected from CN, $NO_2$, $C_{1-3}$alkyl, halo$C_{1-3}$alkyl, $C_{1-3}$alkoxy and halo$C_{1-3}$ alkoxy groups;

$R^4$ is independently selected from the group consisting of:
Aryl, HAR or Hetcy, each optionally substituted as set forth below:
  (1) 1-3 $C_{1-14}$alkyl, $C_{2-10}$alkenyl or $C_{2-10}$alkynyl groups optionally substituted with 1-5 halo groups, 1-2 OH, $CO_2R^a$, CN or $S(O)_pR^d$ groups or phenyl optionally substituted as follows: 1-5 halo groups up to perhalo; 1-3 $C_{1-10}$alkyl or alkoxy groups, each being further optionally substituted with 1-5 halo up to perhalo, or 1-2 hydroxy or $CO_2R^a$ groups;
(2) 1-3 $C_{1-10}$alkoxy or $C_{3-10}$alkenyloxy groups, the alkyl portion of which is optionally substituted with 1-5 halo groups, 1-2 OH, $CO_2R^a$, CN, $S(O)_pR^d$, and phenyl optionally substituted as follows: 1-5 halo groups up to perhalo; 1-3 $C_{1-10}$alkyl or alkoxy groups, each being further optionally substituted with 1-5 halo up to perhalo, or 1-2 hydroxy or $CO_2R^a$ groups;
(3) 1-2 Aryl, HAR or Hetcy, OAryl, OHAR or OHetcy groups, each optionally substituted as follows:
  (i) 1-3 halo groups;
  (ii) 1-2 $C_{1-10}$alkyl, $C_{2-10}$alkenyl or $C_{2-10}$alkynyl groups each optionally substituted with 1-5 halo groups, 1-2 OH, phenyl, $CO_2R^a$, CN or $S(O)_pR^d$ groups;
  (iii) 1-2 $C_{1-10}$alkoxy groups the alkyl portion of which being optionally substituted with 1-5 halo groups, 1-2 OH, phenyl, $CO_2R^a$, CN or $S(O)_pR^d$ groups; and
  (iv) 1-2 $CO_2R^a$, $S(O)_pR^d$, CN, $NR^bR^c$, $NO_2$ or OH groups;
said Aryl, HAR or Hetcy group $R^4$ being further optionally substituted on carbon by a group selected from the group consisting of;
(4) 1-5 halo groups;
(5) 1-2 OH groups;
(6) 1 $S(O)_pR^d$, $NO_2$ or CN group;
(7) 1-2 $CO_2R^a$;

$R^5$ represents H or $C_{1-6}$ alkyl;
$R^6$ is selected from the group consisting of H, OH, F or $C_{1-3}$alkyl;
$R^7$ is H or F, or $R^6$ and $R^7$ are taken in combination and represent oxo;
$R^8$ represents H or $C_{1-6}$ alkyl, optionally substituted with OH and 1-5 halo groups up to perhalo;
$R_9$ represents H, halo, OH, $C_{1-6}$alkyl, optionally substituted with 1-5 halo groups up to perhalo, or $C_{1-6}$alkoxy, optionally substituted with 1-3 halo groups up to perhalo,
or when $R^9$ is ortho to the benzylic group, $R^8$ and $R^9$ can be taken together and represent a $-(CH_2)_{2-4}-$ or a $-O-(CH_2)_{1-3}-$ group;
$R^a$ is H or $C_{1-10}$alkyl, optionally substituted with phenyl, OH, $OC_{1-6}$alkyl, $CO_2H$, $CO_2C_{1-6}$alkyl and 1-3 halo groups;
$R^b$ is H or $C_{1-10}$alkyl;
$R^c$ is H or is independently selected from:
  (a) $C_{1-10}$alkyl, optionally substituted with OH, $OC_{1-6}$alkyl, $CO_2H$, $CO_2C_{1-6}$alkyl, and 1-3 halo groups;
  (b) Aryl or Ar-$C_{1-6}$alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo;
  (c) Hetcy or Hetcy-$C_{1-6}$alkyl, optionally substituted with 1-5 halo groups and 1-3 groups selected from: oxo, $C_{1-10}$alkyl and $OC_{1-10}$alkyl, said alkyl and alkoxy being further optionally substituted with 1-5 halo groups up to perhalo; and
  (d) HAR or HAR-$C_{1-6}$alkyl, optionally substituted with 1-5 halo groups and 1-3 groups selected from: $C_{1-10}$alkyl and $OC_{1-10}$alkyl, said alkyl and alkoxy being further optionally substituted with 1-5 halo groups up to perhalo;

$R^d$ is $C_{1-10}$alkyl, Aryl or Ar-$C_{1-10}$alkyl;
m is an integer selected from 0, 1 and 2;
n is an integer selected from 0 to 6;
p is an integer selected from 0, 1 and 2, and
when at least one of m and n is other than 0, Z is selected from $CO_2R^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl).

2. A compound in accordance with claim 1 wherein $R^1$ is selected from the group consisting of: H, halo, $C_{1-10}$alkyl and $OC_{1-10}$alkyl, said alkyl and O-alkyl groups being optionally substituted with 1-5 halo groups up to a perhaloalkyl or perhaloalkoxy.

3. A compound in accordance with claim 2 wherein $R^1$ is selected from the group consisting of: H, halo, C1-4 alkyl, C1-4 alkoxy, said alkyl and alkoxy being optionally substituted with 1-3 halo groups.

4. A compound in accordance with claim 1 wherein each $R^2$ represents H or is independently selected from the group consisting of:
  a) halo or $S(O)_pR^d$; wherein p is 2 and $R^d$ represents $C_{1-10}$alkyl;
  b) $C_{1-10}$alkyl, $C_{2-10}$alkenyl, $OC_{1-10}$alkyl and $OC_{3-10}$alkenyl, said groups being optionally substituted with:
    (1) 1-5 halo groups up to a perhaloalkyl group;
    (2) 1 $C_{1-10}$alkoxy group, each optionally substituted with: up to five halo or perhaloalkoxy, 1 OH or $CO_2R^a$ group;
    (3) 1 Aryl or HAR group, each optionally substituted as follows:
      (a) 1-5 halo groups,
      (b) 1-2 $C_{1-10}$alkyl or alkoxy groups, each optionally substituted with: 1-5 halo, up to perhaloalkyl, and 1-2 OH or $CO_2R^a$ groups;
  c) Aryl or HAR, each optionally substituted with:
    (1) 1-2 $C_{1-10}$alkyl groups optionally substituted with 1-5 halo groups;
    (2) 1-2 $C_{1-10}$alkoxy groups, the alkyl portion of which is optionally substituted with 1-5 halo groups;
said Aryl or HAR being further optionally substituted on carbon by 1-3 halo groups; up to perhalo.

5. A compound in accordance with claim 4 wherein one $R^2$ group represents H and the other represents H or is selected from the group consisting of:
  a) halo or $S(O)_pR^d$; wherein p is 2 and $R^d$ represents $C_{1-10}$alkyl;
  b) $C_{1-10}$alkyl, $C_{2-10}$alkenyl, $OC_{1-10}$alkyl or $OC_{3-10}$alkenyl, said groups being optionally substituted with:
    (1) 1-5 halo groups up to a perhaloalkyl group;
    (2) 1 $C_{1-10}$alkoxy group, each optionally substituted with: up to five halo or a perhaloalkoxy, 1 OH or $CO_2R^a$ group;
    (3) 1 Aryl or HAR group, each optionally substituted as follows:
      (a) 1-5 halo groups,
      (b) 1-2 C110 alkyl or alkoxy groups, each optionally substituted with: 1-5 halo, up to perhaloalkyl, and 1-2 OH or $CO_2R^a$ groups;
  c) Aryl or HAR, each optionally substituted with:
    (1) 1-2 $C_{1-10}$alkyl groups optionally substituted with 1-5 halo groups;
    (2) 1-2 $C_{1-10}$alkoxy groups, the alkyl portion of which is optionally substituted with 1-5 halo groups;

said Aryl or HAR being further optionally substituted on carbon by 1-3 halo groups; up to perhalo. Within this subset, all other variables are as originally defined with respect to formula I.

6. A compound in accordance with claim 5 wherein:
one $R^2$ group represents H and the other represents H or a member selected from the group consisting of:
 a) halo or $S(O)_pR^d$; wherein p is 2 and $R^d$ represents $C_{1-2}$alkyl;
 b) $C_{1-4}$alkyl, $C_{2-4}$alkenyl, $OC_{1-4}$alkyl or $OC_{3-4}$alkenyl, said groups being optionally substituted with:
  (1) 1-5 halo groups up to a perhaloalkyl group;
  (2) 1 $C_{1-4}$alkoxy group, optionally substituted with: up to 3 halo or a perhaloalkoxy group;
  (3) 1 Aryl or HAR group, each optionally substituted as follows:
   (a) 1-3 halo groups,
   (b) 1 $C_{1-4}$alkyl or alkoxy group, each optionally substituted with: 1-3 halo up to perhaloalkyl, groups;
 c) Aryl or HAR, each optionally substituted with:
  (1) 1-2 $C_{1-4}$alkyl groups optionally substituted with 1-3 halo groups;
  (2) 1-2 $C_{1-4}$alkoxy groups, the alkyl portion of which is optionally substituted with 1-3 halo groups;
said Aryl or HAR being further optionally substituted on carbon by 1-3 halo groups; up to perhalo.

7. A compound in accordance with claim 1 wherein $R^3$ is selected from the group consisting of:
 a) $C_{1-6}$alkyl optionally substituted with:
  1-3 halo groups up to perhalo;
  1 OH, $C_{1-3}$alkoxy or halo$C_{1-3}$alkoxy group;
  1 $NR^cR^d$ group; and
  1 Aryl or HAR group, each optionally substituted with 1-3 halo groups and 1-2 groups selected from $C_{1-3}$alkyl, halo$C_{1-3}$alkyl, $C_{1-3}$alkoxy and halo$C_{1-3}$alkoxy groups,
 b) Aryl or HAR, each optionally substituted with 1-3 halo groups and 1-2 groups selected from $C_{1-3}$alkyl, halo$C_{1-3}$alkyl, $C_{1-3}$alkoxy and halo$C_{1-3}$alkoxy groups.

8. A compound in accordance with claim 7 wherein $R^3$ is selected from the group consisting of:
 a) $C_{1-6}$alkyl optionally substituted with:
  1-3 halo groups up to perhalo;
  1 $C_{1-3}$alkoxy or halo$C_{1-3}$alkoxy group;
  1 $NR^cR^d$ group; wherein $R^c$ and $R^d$ are independently selected from H, $C_{1-3}$alkyl and phenyl; and
  1 Aryl or HAR group, each optionally substituted with 1-3 halo groups and 1-2 groups selected from $C_{1-3}$alkyl, halo$C_{1-3}$alkyl, $C_{1-3}$alkoxy and halo$C_{1-3}$ alkoxy groups,
 b) Aryl or HAR, each optionally substituted with 1-3 halo groups and 1 group selected from: $C_{1-3}$alkyl, halo$C_{1-3}$alkyl, $C_{1-3}$alkoxy and halo$C_{1-3}$ alkoxy.

9. A compound in accordance with claim 1 wherein:
$R^4$ represents an Aryl or HAR group, each optionally substituted as set forth below:
 (1) 1-2 $C_{1-10}$alkyl or $C_{2-10}$alkenyl groups, which are optionally substituted with 1-3 halo groups, or phenyl optionally substituted with 1-2 halo, $C_{1-4}$alkyl or alkoxy groups, each being further optionally substituted with 1-3 halo groups;
 (2) 1-2 $C_{1-10}$alkoxy or $C_{3-10}$alkenyloxy groups, which are optionally substituted with 1-3 halo groups, 1-2 OH or $S(O)_pR^d$, and phenyl optionally substituted as follows: 1-3 halo groups up to perhalo; 1-2 $C_{1-6}$alkyl or alkoxy groups, each being further optionally substituted with 1-3 halo up to perhalo, or 1-2 hydroxy or $CO_2R^a$ groups;
 (3) 1-2 Aryl, HAR or Hetcy, OAryl, OHAR or OHetcy groups, each optionally substituted as follows:
  (i) 1-3 halo groups;
  (ii) 1-2 $C_{1-3}$alkyl or $C_{2-4}$alkenyl groups each optionally substituted with 1-3 halo groups, and 1 of OH, phenyl, $CO_2R^a$, CN and $S(O)_pR^d$;
  (iii) 1-2 $C_{1-3}$alkoxy groups the alkyl portion of which being optionally substituted with 1-3 halo groups, and 1 of OH, phenyl, $CO_2R^a$, CN or $S(O)_pR^d$; and
  (iv) 1-2 $CO_2R^a$, $S(O)_pR^d$, CN, $NR^bR^c$, $NO_2$ or OH groups;
said Aryl, HAR or Hetcy group R4 being further optionally substituted on carbon by a group selected from the group consisting of;
  (4) 1-5 halo groups;
  (5) 1-2 OH groups;
  (6) 1 $S(O)_pR^d$, $NO_2$ or CN group.

10. A compound in accordance with claim 1 wherein $R^5$ represents H or $CH_3$.

11. A compound in accordance with claim 1 wherein $R^8$ is selected from the group consisting of H and $C_{1-3}$alkyl.

12. A compound in accordance with claim 1 wherein $R^6$ and $R^7$ represent H.

13. A compound in accordance with claim 9 wherein $R^9$ represents H.

14. A compound in accordance with claim 1 wherein m is 0 and n is an integer selected from 0 to 2.

15. A compound in accordance with claim 1 wherein when n is 1 or 2, Z is selected from $CO_2R^a$ and 5-tetrazolyl, when both m and n are 0, Z is 5-tetrazolyl.

16. A compound in accordance with claim 1 wherein:
$R^1$ is selected from the group consisting of: H, halo, $C_{1-10}$alkyl and $OC_{1-10}$alkyl, said alkyl and O-alkyl groups being optionally substituted with 1-5 halo groups up to a perhaloalkyl or perhaloalkoxy;
each $R^2$ represents H or is independently selected from the group consisting of:
 a) halo or $S(O)_pR^d$; wherein p is 2 and $R^d$ represents $C_{1-10}$alkyl;
 b) $C_{1-10}$alkyl, $C_{2-10}$alkenyl, $OC_{1-10}$alkyl and $OC_{3-10}$alkenyl, said groups being optionally substituted with:
  (1) 1-5 halo groups up to perhaloalkyl;
  (2) 1 $C_{1-10}$alkoxy group, each optionally substituted with: up to five halo or perhaloalkoxy, 1 OH or $CO_2R^a$ group;
  (3) 1 Aryl or HAR group, each optionally substituted as follows:
   (a) 1-5 halo groups,
   (b) 1-2 $C_{1-10}$alkyl or alkoxy groups, each optionally substituted with: 1-5 halo, up to perhaloalkyl, and 1-2 OH or $CO_2R^a$ groups;
 c) Aryl or HAR, each optionally substituted with:
  (1) 1-2 $C_{1-10}$alkyl groups optionally substituted with 1-5 halo groups;
  (2) 1-2 $C_{1-10}$alkoxy groups, the alkyl portion of which is optionally substituted with 1-5 halo groups;
said Aryl or HAR being further optionally substituted on carbon by 1-3 halo groups; up to perhalo;
$R^3$ selected from the group consisting of:
 a) $C_{1-6}$alkyl optionally substituted with:
  1-3 halo groups up to perhalo;
  1 OH, $C_{1-3}$alkoxy or halo$C_{1-3}$alkoxy group;
  1$NR^cR^d$ group; and 1 Aryl or HAR group, each optionally substituted with 1-3 halo groups and 1-2 groups selected from $C_{1-3}$alkyl, halo$C_{1-3}$alkyl, $C_{1-3}$alkoxy and halo$C_{1-3}$alkoxy;

b) Aryl or HAR, each optionally substituted with 1-3 halo groups and 1-2 groups selected from $C_{1-3}$alkyl, halo$C_{1-3}$ alkyl, $C_{1-3}$alkoxy and halo$C_{1-3}$alkoxy;

$R^4$ represents an Aryl or HAR group, each optionally substituted as set forth below:
  (1) 1-2 $C_{1-10}$alkyl or $C_{2-10}$alkenyl groups, which are optionally substituted with 1-3 halo groups, or phenyl optionally substituted with 1-2 halo, $C_{1-4}$alkyl or alkoxy groups, each being further optionally substituted with 1-3 halo groups;
  (2) 1-2 $C_{1-10}$alkoxy or $C_{3-10}$alkenyloxy groups, which are optionally substituted with 1-3 halo groups, 1-2 OH or $S(O)_pR^d$, and phenyl optionally substituted as follows: 1-3 halo groups up to perhalo; 1-2 $C_{1-6}$alkyl or alkoxy groups, each being further optionally substituted with 1-3 halo up to perhalo, or 1-2 hydroxy or $CO_2R^a$ groups;
  (3) 1-2 Aryl, HAR or Hetcy, OAryl, OHAR or OHetcy groups, each optionally substituted as follows:
    (i) 1-3 halo groups;
    (ii) 1-2 $C_{1-3}$alkyl or $C_{2-4}$alkenyl groups each optionally substituted with 1- 3 halo groups, and 1 of OH, phenyl, CO2$R^a$, CN and $S(O)_pR^d$;
    (iii) 1-2 $C^{1-3}$alkoxy groups the alkyl portion of which being optionally substituted with 1-3 halo groups, and 1 of OH, phenyl, CO2$R^a$, CN and $S(O)_pR^d$; and
    (iv) 1-2 $CO_2R^a$, $S(O)_pR^d$, CN, $NR^bR^c$, $NO_2$ or OH groups;

said Aryl, HAR or Hetcy group $R^4$ being further optionally substituted on carbon by a group selected from the group consisting of;
  (4) 1-5 halo groups;
  (5) 1-2 OH groups;
  (6) 1 $S(O)_pR^d$, $NO_2$ or CN group;

$R^5$ H or $CH_3$;

$R^8$ is selected from the group consisting of H and $C_{1-3}$alkyl;

$R^6$, $R^7$ $R^9$ represents H;

and m is 0 and n is an integer selected from 0 to 2, such that when n is 1 or 2, Z is selected from $CO_2R^a$ and 5-tetrazolyl, and when both m and n are 0, Z is 5-tetrazolyl.

17. A compound in accordance with claim 16 wherein $R^1$ is selected from the group consisting of: H, halo, Cl-4 alkyl, C1-4 alkoxy, said alkyl and alkoxy being optionally substituted with 1-3 halo groups.

18. A compound in accordance with claim 1 selected from Table 1a or 1b below:

TABLE 1a

| Cpd | $R^1$ | $R^{2a}$ | $R^{2b}$ | $R^3$ | $R^4$ |
|---|---|---|---|---|---|
| 1 | H | H | H | —Me | 4-(cyclohexenyl)phenyl |
| 2 | Cl | Cl | H | —Et | 4-($OCF_3$)phenyl |
| 3 | Cl | H | H | —Me | 4-($OCF_3$)phenyl |
| 4 | Cl | Cl | H | —Et | 4-($OCF_3$)phenyl |
| 5 | —$OCF_3$ | H | H | —Me | 4-($OCF_3$)phenyl |

TABLE 1a-continued
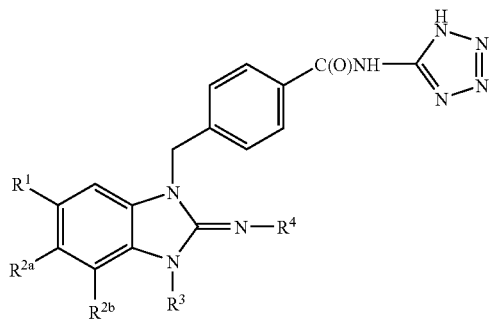
| Cpd | R¹ | R²ᵃ | R²ᵇ | R³ | R⁴ |
|---|---|---|---|---|---|
| 6 | Cl | H | —O(CH₂)₂CH₃ | —Et | 4-OCF₃-phenyl |
| 7 | —CF₃ | Cl | H | —Me | 4-OCF₃-phenyl |
| 8 | Cl | Cl | H | —Me | 4-O(CH₂)₂CH₃-phenyl |
| 9 | Cl | H | Cl | —Me | 4-OCF₃-phenyl |
| 10 | —CF₃ | H | H | —Me | 3-CF₃-phenyl |
| 11 | Cl | Cl | H | —Me | 4-OCF₃-phenyl |
| 12 | —CF₃ | H | H | —Me | 4-CF₃-phenyl |
| 13 | H | Cl | H | —Me | 4-OCF₃-phenyl |
| 14 | Cl | Cl | H | —Me | 4-OCF₃-3-Br-phenyl |
| 18 | —CF₃ | H | H | —Et | 4-OCF₃-phenyl |

TABLE 1a-continued
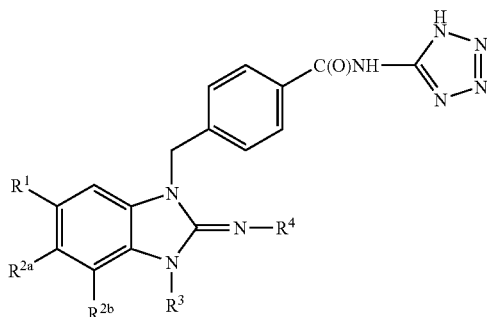
| Cpd | R¹ | R²ᵃ | R²ᵇ | R³ | R⁴ |
|---|---|---|---|---|---|
| 19 | H | H | H | —Me | 3,5-dichlorophenyl |
| 20 | —OMe | H | H | —Me | 3,5-dichlorophenyl |
| 22 | Cl | Cl | H | —Me | 3,5-dichlorophenyl |
| 23 | Cl | Cl | H | —Me | 4-(OCH₂CH=CH₂)phenyl |
| 24 | Cl | Cl | H | —Me | 4-cyclohexylphenyl |
| 26 | —CF₃ | H | H | —Me | 4-chlorophenyl |
| 27 | —OnPr | H | H | —Me | 4-OCF₃-phenyl |
| 28 | Cl | Cl | H | —Me | 4-hydroxyphenyl |
| 31 | Cl | Cl | H | —Et | 3-Br-4-OCF₃-phenyl |

TABLE 1a-continued
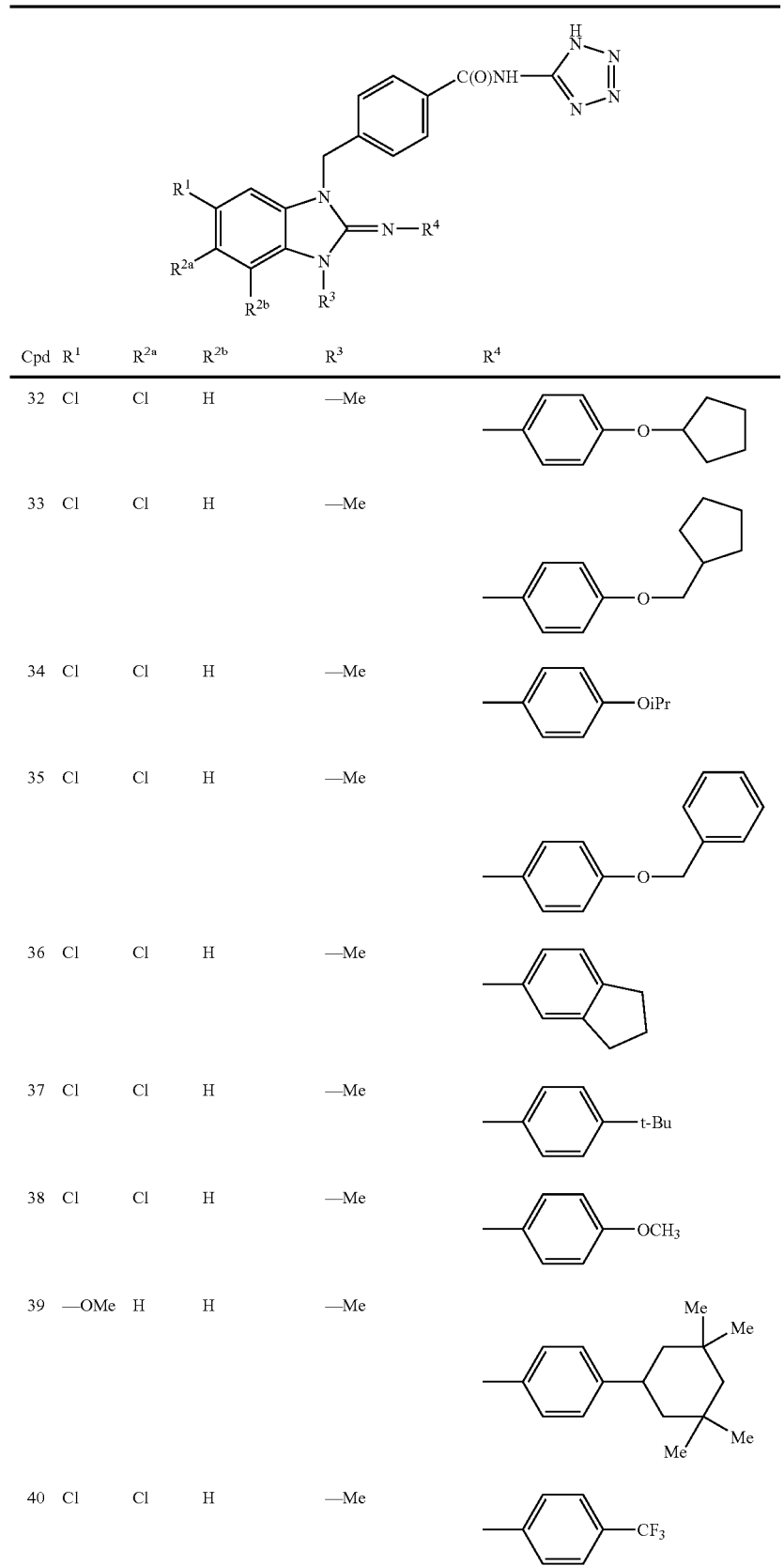
| Cpd | R¹ | R²ᵃ | R²ᵇ | R³ | R⁴ |
|---|---|---|---|---|---|
| 32 | Cl | Cl | H | —Me | 4-(cyclopentyloxy)phenyl |
| 33 | Cl | Cl | H | —Me | 4-(cyclopentylmethoxy)phenyl |
| 34 | Cl | Cl | H | —Me | 4-OiPr-phenyl |
| 35 | Cl | Cl | H | —Me | 4-(benzyloxy)phenyl |
| 36 | Cl | Cl | H | —Me | 2,3-dihydro-1H-indenyl |
| 37 | Cl | Cl | H | —Me | 4-t-Bu-phenyl |
| 38 | Cl | Cl | H | —Me | 4-OCH₃-phenyl |
| 39 | —OMe | H | H | —Me | 4-(3,3,5,5-tetramethylcyclohexyl)phenyl |
| 40 | Cl | Cl | H | —Me | 4-CF₃-phenyl |

TABLE 1a-continued
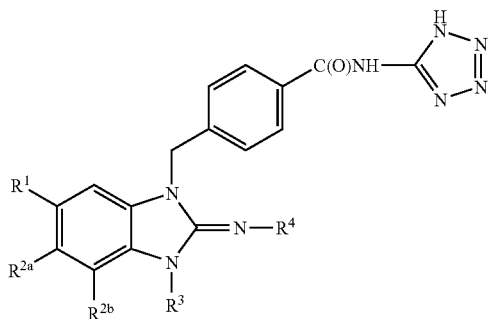
| Cpd | R¹ | R²ᵃ | R²ᵇ | R³ | R⁴ |
|---|---|---|---|---|---|
| 41 | Cl | Cl | H | -CH₂-C₆H₅ (ethylbenzyl) | 4-OCF₃-C₆H₄ |
| 42 | —OMe | H | H | —Me | 4-(4,4-difluorocyclohexyl)-C₆H₄ |
| 43 | Cl | H | —OnBu | —Me | 4-OCF₃-C₆H₄ |
| 44 | H | —OnPr | H | —Me | 4-OCH₂CF₃-C₆H₄ |
| 45 | Cl | Cl | H | —Me | 3-OCF₃-C₆H₄ |
| 46 | Cl | Cl | H | —Me | 3,4-diCl-C₆H₃ |
| 47 | Cl | Cl | H | —CH₂CH₂F | 4-OCF₃-C₆H₄ |
| 48 | Cl | Cl | H | iPr | 4-OCF₃-C₆H₄ |
| 49 | Cl | Cl | H | —(CH₂)₂OMe | 4-OCF₃-C₆H₄ |
| 50 | Cl | Cl | H | —(CH₂)₂NMe₂ | 4-OCF₃-C₆H₄ |
| 51 | CF₃ | H | H | Me | 4-cyclohexyl-C₆H₄ |

TABLE 1a-continued
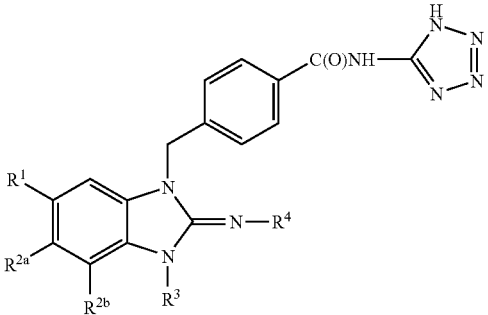
| Cpd | R¹ | R²ᵃ | R²ᵇ | R³ | R⁴ |
|---|---|---|---|---|---|
| 52 | CF₃ | H | CF₃ | Me | 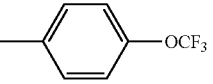 |
| 53 | Cl | Cl | H | —(CH₂)₃OMe | 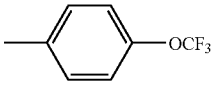 |
| 54 | CF₃ | H | H | Me | 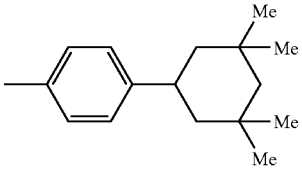 |
| 55 | CF₃ | H | Br | Me | 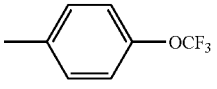 |
| 56 | Cl | Cl | H | —(CH₂)₃NMe₂ | 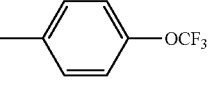 |
| 57 | OMe | H | H | Me | 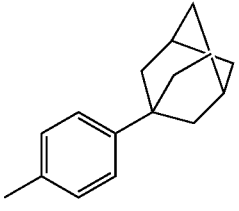 |
| 58 | Cl | H | OMe | Me | 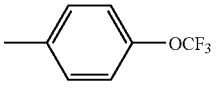 |
| 59 | CF₃ | H | Et | Me | 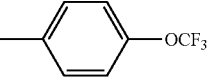 |
| 60 | Cl | H | OMe | Me | 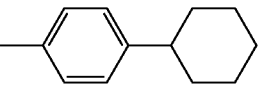 |
| 61 | H | —OnPr | H | Me | 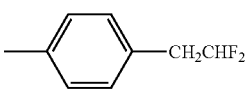 |

TABLE 1a-continued

| Cpd | R¹ | R²ᵃ | R²ᵇ | R³ | R⁴ |
|---|---|---|---|---|---|
| 62 | CF₃ | H | —CH=CH₂ | Me | 4-OCF₃-phenyl |
| 63 | CF₃ | H | SO₂Me | Me | 4-OCF₃-phenyl |
| 64 | CF₃ | H | H | Me | 4-nBu-phenyl |
| 65 | CF₃ | H | Et | Me | indan-5-yl |
| 66 | CF₃ | H | Me | Me | 4-OCF₃-phenyl |
| 67 | CF₃ | H | Et | Me | 4-F-phenyl |
| 68 | CF₃ | H | Et | Me | 4-tBu-phenyl |
| 69 | Cl | H | OiPr | Me | 4-OCF₃-phenyl |
| 70 | Cl | H | OnPr | Me | 4-OCF₃-phenyl |
| 71 | CF₃ | H | phenyl | Me | 4-OCF₃-phenyl |
| 72 | Cl | H | OEt | Me | 4-OCF₃-phenyl |
| 73 | CF₃ | H | H | Me | 4-(2,3-dimethylcyclopentyl)phenyl |

TABLE 1a-continued
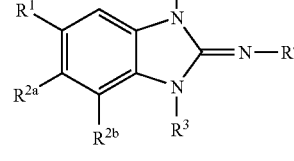
| Cpd | R¹ | R²ᵃ | R²ᵇ | R³ | R⁴ |
|-----|-----|-----|-----|-----|-----|
| 74 | Cl | H | OMe | Me | 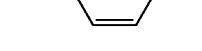 |
| 75 | CF₃ | H | Et | Me |  |
| 76 | OMe | H | H | Me | 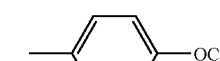 |
| 77 | CF₃ | H | OnBu | Me | 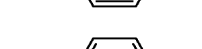 |
| 78 | CF₃ | H | Et | Me | 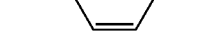 |
| 79 | L | H | OMe | Me | 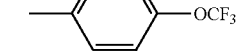 |
| 80 | F | H | H | Me | 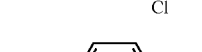 |
| 81 | CF₃ | H | OMe | Me | 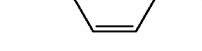 |
| 82 | Cl | H | OH | Me | 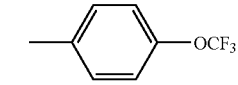 |
| 83 | OMe | H | H | Me | 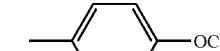 |
| 84 | CF₃ | H | OnPr | Me | 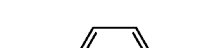 |

TABLE 1a-continued
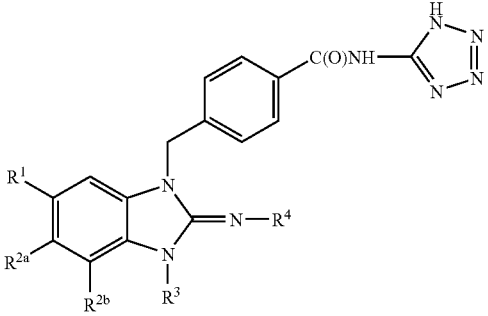
| Cpd | R¹ | R²ᵃ | R²ᵇ | R³ | R⁴ |
|---|---|---|---|---|---|
| 85 | CF₃ | H | OMe | Me | 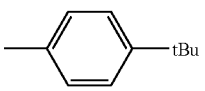 4-tBu-phenyl |
| 86 | CF₃ | H | OMe | Me | 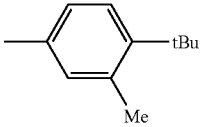 3-tBu-4-Me... |
| 87 | H | H | OnPr | Me | 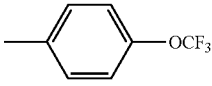 4-OCF₃-phenyl |
| 88 | CF₃ | H | OnPr | Me | 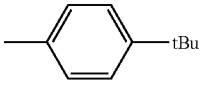 4-tBu-phenyl |
| 90 | CF₃ | H | OEt | Me | 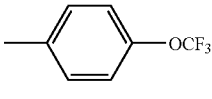 4-OCF₃-phenyl |
| 91 | CF₃ | H | Et | Et | 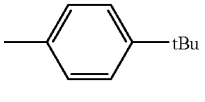 4-tBu-phenyl |
| 92 | CF₃ | H | Et | Et | 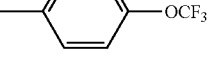 4-OCF₃-phenyl |
| 95 | CF₃ | H | Cl | Me | 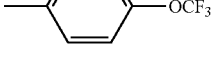 4-OCF₃-phenyl |
| 96 | CF₃ | H | H | Me | 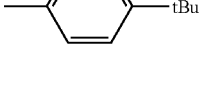 4-tBu-phenyl |
| 97 | H | OnPr | H | Me | 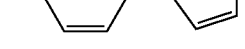 4-(3-thienyl)phenyl |

TABLE 1b

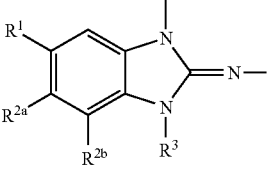

| Cpd | R¹ | R²ᵃ | R²ᵇ | R³ | R⁴ |
|---|---|---|---|---|---|
| 15 | H | Cl | H | Me |  |
| 17 | Cl | Cl | H | Me |  |
| 21 | OMe | H | H | Me | 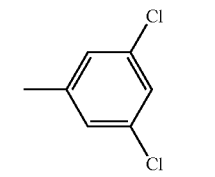 |
| 25 | Cl | Cl | H | Me | 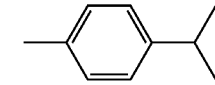 |
| 29 | $CF_3$ | H | H | Me |  |
| 30 | $CF_3$ | H | H | Me | 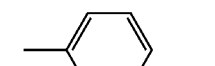 |

TABLE 1b-continued

| Cpd | R¹ | R²ᵃ | R²ᵇ | R³ | R⁴ |
|---|---|---|---|---|---|
| 89 | Cl | H | OnPr | Et | 4-OCF₃-phenyl |
| 93 | H | H | OnPr | Me | 4-OCF₃-phenyl |
| 94 | $CF_3$ | H | H | Me | 4-CF₃-phenyl | or a pharmaceutically acceptable salt or solvate thereof.

19. A pharmaceutical composition comprising a compound in accordance with claim 1 in combination with a pharmaceutically acceptable carrier.

20. A method of treating type 2 diabetes mellitus in a mammalian patient in need of such treatment comprising administering to said patient a compound in accordance with claim 1 in an amount that is effective to treat said type 2 diabetes mellitus.

* * * * *